(12) United States Patent
Balestra et al.

(10) Patent No.: US 10,858,342 B2
(45) Date of Patent: Dec. 8, 2020

(54) BICYCLIC IMIDAZOLE DERIVATIVES USEFUL FOR THE TREATMENT OF RENAL DISEASES, CARDIOVASCULAR DISEASES AND FIBROTIC DISEASES

(71) Applicant: Boehringer Ingelheim International GmbH, Ingelheim am Rhein (DE)

(72) Inventors: Michael Balestra, New Fairfield, CT (US); Jennifer Burke, Newtown, CT (US); Zhidong Chen, Ridgefield, CT (US); Derek Cogan, Boston, MA (US); John Lord, Poughkeepsie, NY (US); Daniel Richard Marshall, Norwalk, CT (US); Bryan P. McKibben, New Milford, CT (US); Kenneth M. Meyers, Seymour, CT (US); Yunlong Zhang, Valhalla, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 54 days.

(21) Appl. No.: 16/310,458

(22) PCT Filed: Jun. 21, 2017

(86) PCT No.: PCT/US2017/038440
§ 371 (c)(1),
(2) Date: Dec. 17, 2018

(87) PCT Pub. No.: WO2018/005177
PCT Pub. Date: Jan. 4, 2018

(65) Prior Publication Data
US 2020/0109131 A1 Apr. 9, 2020

Related U.S. Application Data

(60) Provisional application No. 62/355,374, filed on Jun. 28, 2016.

(51) Int. Cl.
| | | |
|---|---|---|
| C07D 403/04 | (2006.01) |
| C07D 235/26 | (2006.01) |
| C07D 401/04 | (2006.01) |
| C07D 403/06 | (2006.01) |
| C07D 403/10 | (2006.01) |
| C07D 405/04 | (2006.01) |
| C07D 405/06 | (2006.01) |
| C07D 413/04 | (2006.01) |
| C07D 417/06 | (2006.01) |
| C07D 471/04 | (2006.01) |
| C07D 491/107 | (2006.01) |
| C07D 498/04 | (2006.01) |

(52) U.S. Cl.
CPC ........ *C07D 403/04* (2013.01); *C07D 235/26* (2013.01); *C07D 401/04* (2013.01); *C07D 403/06* (2013.01); *C07D 403/10* (2013.01); *C07D 405/04* (2013.01); *C07D 405/06* (2013.01); *C07D 413/04* (2013.01); *C07D 417/06* (2013.01); *C07D 471/04* (2013.01); *C07D 491/107* (2013.01); *C07D 498/04* (2013.01)

(58) Field of Classification Search
None
See application file for complete search history.

(56) References Cited

FOREIGN PATENT DOCUMENTS

| WO | 2007100295 A1 | 9/2007 |
| WO | 2016014736 A1 | 1/2016 |

OTHER PUBLICATIONS

Sonegawa et al. "Regioselective Alkylation of 2-Alkyl-5,6,7,8-tetrahydro-3H-cycloheptimidazol-4-ones and 2-Alkyl-3H-cycloheptimidazol-4-ones" Chemical and Pharmaceutical Bulletin, 2006, vol. 54, No. 5, pp. 706-710.*
Mityanov et al. "Regioselective synthesis of 2-unsubstituted 1-aryl-4- and 1-aryl-5-acylimidazoles" Tetrahedron, 2014, vol. 70, No. 22, pp. 3545-3552.*
International Report on Patetability for PCT/US2017038440 dated Jan. 10, 2019.

* cited by examiner

*Primary Examiner* — Joseph R Kosack
(74) *Attorney, Agent, or Firm* — David L. Kershner

(57) ABSTRACT

The present invention relates to compounds of formula I: and pharmaceutically acceptable salts thereof, wherein $R^1$, $R^2$, $R^3$, $R^4$, $R^5$ and n are as defined herein. The invention also relates to pharmaceutical compositions comprising these compounds, methods of using these compounds in the treatment of various diseases and disorders, processes for preparing these compounds and intermediates useful in these processes.

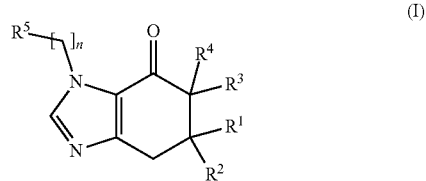

(I)

11 Claims, No Drawings

BICYCLIC IMIDAZOLE DERIVATIVES USEFUL FOR THE TREATMENT OF RENAL DISEASES, CARDIOVASCULAR DISEASES AND FIBROTIC DISEASES

FIELD OF THE INVENTION

This invention relates to heteroaryl compounds that are useful as inhibitors of aldosterone synthase (CYP11B2) and are thus useful for treating a variety of diseases that are mediated or sustained by aldosterone activity, including renal disease, diabetic nephropathy, cardiovascular diseases and fibrotic disorders. This invention also relates to pharmaceutical compositions comprising these compounds, methods of using these compounds in the treatment of various diseases and disorders, processes for preparing these compounds and intermediates useful in these processes.

BACKGROUND

Aldosterone is a steroid hormone having mineralocorticoid activity. It is produced primarily by the adrenal glomerulosa in response to angiotensin II, adrenocorticotropic hormone and increased serum potassium levels. A primary physiological role of aldosterone in the kidney is to maintain sodium and potassium balance by regulating cation exchange ($Na^+$ reabsorption and $K^+$ secretion) in the distal nephron. However, aldosterone has also been shown to be a pro-inflammatory and profibrotic hormone in blood vessels, heart and kidneys. The effects of aldosterone on gene expression are mediated via binding to the mineralocorticoid receptor (MR) and a canonical nuclear hormone receptor pathway. However, the hormone also elicits rapid, non-genomic responses, including acute regulation of the activity of tubular ion transporters, for example $Na^+/H^+$ exchangers (NHEs), $H^+$-ATPase, ENaC, and $Na^+/K^+$ ATPase (D. W. Good, 2007, Hypertension, 49, 728-739). It is likely that some of these effects are mediated by MR-independent pathways. Conversely, the MR can bind alternative ligands, including deoxycorticosterone, corticosterone, cortisol and progesterone. Thus, inhibition of aldosterone synthesis is predicted to have a pharmacodynamic profile distinct from what is observed with MR antagonists.

Aldosterone is synthesized in the zona glomerulosa of the adrenal glands, where a single enzyme, CYP11B2 (aldosterone synthase), catalyzes the 3-step conversion of 11-deoxycorticosterone (11-DOC) to aldosterone, via corticosterone and 18-hydroxycorticosterone. Adrenal aldosterone synthase activity is regulated by Angiotensin II and K+ levels and unidentified adipocyte-derived mediators. Low levels of aldosterone synthase have also been detected in the heart and CNS, though the physiological relevance is uncertain, perhaps relating to paracrine effects. Systemic aldosterone is believed to derive essentially entirely from the adrenals.

Beyond its role in regulating sodium and potassium balance, aldosterone has been shown to have pro-inflammatory and pro-fibrotic actions in multiple tissues including the kidney, blood vessels and the heart. The harmful effects of inappropriate aldosterone levels on blood pressure and cardiac, renal, cerebral and vascular function and structure, have been widely reported in the literature, including: i) increase in sodium retention through $Na^+/K^+$ ATPase pump induction in distal tubules resulting in volume expansion and high blood pressure, ii) endothelial dysfunction, iii) oxidative stress, iv) renal and cardiac hypertrophy, v) fibroblast proliferation, and, vi) excessive synthesis of extracellular matrix resulting in renal, cardiac and vascular fibrosis.

Benefits of aldosterone blockade/inhibition include reduction of kidney fibrosis and improvement of glomerular filtration rate and albuminuria in models of chronic kidney disease (CKD) and diabetic nephropathy. This is supported by pre-clinical data (for example, Fiebler et al., 2005, Circulation, 111, 3087-3094; Lea et al., 2009, Kidney International, 75, 936-945). Other benefits reported in the literature include decreased blood pressure and end-organ damage (heart, kidney, vessels) in both renin-dependent and salt-sensitive hypertension.

Although many of aldosterone's known effects are mediated through mineralocorticoid receptor (MR) activation, and much of the evidence favoring targeting this pathway comes from experiments with MR antagonists, non MR-mediated effects are reported and knockout mice for MR and aldosterone synthase exhibit different phenotypes. These observations further suggest that aldosterone synthase inhibitors may have a different profile and offer advantages compared to MR antagonists.

For example, several aldosterone actions are not inhibited by MR antagonists, including the including potentially deleterious effects on the vasculature (increased peripheral vascular resistance), the heart (effects on myocardial re-polarization) and the endocrine system (decreased insulin secretion). Furthermore, MR antagonism leads to an increase in circulating aldosterone, predicted to increase aldosterone signaling via non-MR pathways and, potentially, partially overcoming the MR blockade itself.

Current therapeutic strategies focus on slowing progression and treating conditions underlying diabetic nephropathy: control of blood glucose and control of high blood pressure. Angiotensin converting enzyme (ACE) inhibitors and angiotensin receptor blockers (ARB) have shown renal benefit in diabetic patients. To date, representatives of the ACE inhibitor class and from the ARB class have been approved for the treatment of diabetic nephropathy. These therapies represent limited benefit for the diabetic nephropathy patients.

Although the use of ACE inhibitors and ARBs represents the current standard of care for patients with diabetic nephropathy, patients progressively lose kidney function while on these medications, as seen in the IDNT (E. J. Lewis et al., 2001, N. Engl. J. Med., 345, 851-860) and RENAAL (B. M. Brenner et al., 2001, N. Engl. J. Med., 345, 861-869) studies, which reported a decrease over time in estimated glomerular filtration rate, which is an accurate measure of chronic kidney disease progression in patients treated by these conventional methods. At stage 5 chronic kidney disease, renal replacement therapy is required, in the form of either dialysis or transplant.

Aldosterone synthase inhibition may also be predicted to offer advantages as add-on therapy with ACE inhibitors and ARBs. Notably, 25-50% of patients receiving these agents experience "aldosterone breakthrough" in which aldosterone levels initially lowered by these treatments eventually return to pretreatment levels. This phenomenon would not occur with direct aldosterone synthase inhibition and could enhance efficacy in combination therapy.

There remains a high unmet medical need to treat diabetic nephropathy, to halt or regress disease progression by specifically targeting the underlying pathophysiological mechanisms associated with chronic inflammation and fibrosis, irrespective of the original cause of the disease and when co-administered with current therapies. The studies described above and in the literature provide evidence that inhibitors of aldosterone synthesis will be useful for the treatment of diabetic kidney disease including diabetic nephropathy; non-diabetic kidney disease including glomerulosclerosis, glomerulonephritis, IGA nephropathy, nephritic syndrome and focal segmental glomerulosclerosis (FSGS); cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism; adrenal hyperplasia and primary and secondary hyperaldosteronism.

BRIEF SUMMARY OF THE INVENTION

The present invention provides novel compounds that inhibit aldosterone synthase (CYP11B2) and thus are useful for treating a variety of diseases and disorders that can be alleviated by lowering levels of aldosterone including renal disease, diabetic nephropathy, cardiovascular diseases and fibrotic disorders. In a further aspect, the invention provides compounds that are selective for inhibition of aldosterone synthase compared to cortisol synthase (CYP11B1). This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In an embodiment of the invention, there are provided compounds of the formula I

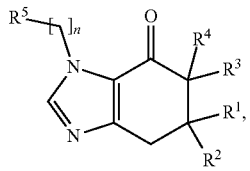

wherein:
$R^1$ and $R^2$ are independently selected from the group consisting of —H, —CO$_2$Et, —C(O)NH$_2$, —C(O)NHCH$_3$, —C(O)N(CH$_3$)$_2$, —C$_{1-3}$alkyl and —CH$_2$OH; or
$R^1$ and $R^2$, together with the carbon they are bonded to, may form a spiro ring selected from the group consisting of C$_{3-4}$cycloalkyl, tetrahydrofuran and tetrahydropyran;
$R^3$ and $R^4$ are both H, or if $R^1$ and $R^2$ are both H, $R^3$ and $R^4$ are independently selected from the group consisting of H and —CH$_3$;
$R^5$ is selected from the group consisting of
phenyl, optionally substituted with one to two groups selected from the group consisting of —CN, —C$_{1-3}$alkyl, optionally substituted with —OH, —C$_{3-6}$cycloalkyl, —Cl, —F, —OC$_{1-3}$alkyl, —C(O)N(Me)(—CH$_2$CH$_2$OH), —C(O) NH(—CH$_2$CH$_2$SO$_2$CH$_3$), —C(O)C$_{1-3}$alkyl, -N(Me)$_2$, —NHC(O)C$_{1-3}$alkyl, —C(O)OC$_{1-3}$alkyl, —SO$_2$C$_{1-3}$alkyl, —CF$_3$, 3-hydroxy-pyrrolidine-1-carbonyl and [1,2,4]triazolyl;

aryl or carbocycle selected from the group consisting of C$_{3-6}$cycloalkyl, bicycle[2.2.1]heptyl, decahydronaphthalenyl, indanyl, spiro[3.3]hept-1-yl, 6,7,8,9-tetrahydro-5H-benzocycloheptenyl and 1,2,3,4-tetrahydronaphthalenyl, wherein said aryl or carbocycle is optionally substituted with —CN, —Br, —OC$_{1-3}$alkyl and phenyl;
heterocyclyl selected from the group consisting of Obenzo[1,3]dioxolyl, 3H-benzoxazolyl, -chromanyl, 3,4-dihydro-2H-benzo[b][1,4]dioxepinyl, 2,3-dihydrobenzo[1,4]dioxinyl, 2,3-dihydrobenzofuranyl, 4H-benzo[1,4]oxazinyl, 2,3-dihydro-1H-indolyl, 1,3-dihydroisobenzofuranyl, 1,4-dihydro-2H-isoquinolinyl, 3,4-dihydro-1H-[1,8]napthyridinyl, 3,4-dihydro-2H-pyrido[3,2-b][1,4]oxazinyl, 3,4-dihydroquinolinyl, 2-oxa-spiro[3,3heptyl, piperidinyl, tetrahydrofuranyl, tetrahydropyranyl, 5,6,7,8-tetrahydroquinazolinyl, 1,2,3,4-tetrahydroquinolinyl, wherein said heterocyclyl is optionally substituted with one to two groups selected from the group consisting of —C(O)CH$_3$, —C$_{1-3}$alkyl, -oxo and —C(O)NH$_2$; and
heteroaryl selected from the group consisting of 1H-indazolyl and pyridyl, [1,2,3]-thiadiazolyl, wherein said heteroaryl is optionally substituted with one to two groups selected from the group consisting of —C$_{1-3}$alkyl, —Cl and —CN;
n is 0 or 1;
or a salt thereof.

In another embodiment, there are provided compounds of the formula I as described according to the embodiment above, and wherein
$R^1$ and $R^2$ are independently selected from the group consisting of —H, —CO$_2$Et, —C(O)NH$_2$, —C(O)NHCH$_3$, —CH$_3$ and —CH$_2$OH; or
$R^1$ and $R^2$, together with the carbon they are bonded to, may form a spiro ring selected from the group consisting of C$_{3-4}$cycloalkyl, tetrahydrofuran and tetrahydropyran;
$R^3$ and $R^4$ are both H, or if $R^1$ and $R^2$ are both H, $R^3$ and $R^4$ are independently selected from the group consisting of —H and —CH$_3$;
$R^5$ is selected from the group consisting of
phenyl, optionally substituted with one to two groups selected from the group consisting of —CN, —C$_{1-3}$alkyl, cyclopropyl, —Cl, —F, —OCH$_3$, —NHC(O)CH$_3$, —C(O) OC$_{1-2}$alkyl, —SO$_2$CH$_3$ and —CF$_3$;
aryl or carbocycle selected from the group consisting of cyclohexyl, indanyl, spiro[3.3]hept-1-yl, 6,7,8,9-tetrahydro-5H-benzocycloheptenyl and 1,2,3,4-tetrahydronaphthalenyl, wherein said aryl or carbocycle is optionally substituted with —CN, —Br and —OC$_{1-2}$alkyl;
heterocyclyl selected from the group consisting of benzo[1,3]dioxolyl, 2,3-dihydrobenzofuranyl, 4H-benzo[1,4]oxazinyl, 1,3-dihydroisobenzofuranyl, 3,4-dihydroquinolinyl and 1,2,3,4-tetrahydroquinolinyl, wherein said heterocyclyl is optionally substituted with one to two groups selected from the group consisting of —C(O)CH$_3$, —CH$_3$, -oxo and —C(O)NH$_2$; and
1H-indazolyl, optionally substituted with —CH$_3$;
n is 0 or 1;
or a salt thereof.

In another embodiment there are provided compounds of the formula I as described according to any of the embodiments above the embodiment above, and wherein
$R^3$ and $R^4$ are both —H;
or a salt thereof.

In another embodiment there are provided compounds of the formula I as described according to any of the embodiments above the embodiment above, and wherein R¹ and R² are independently selected from the group consisting of —H, —CO₂Et, —C(O)NH₂, —C(O)NHCH₃, —C(O)N(CH₃)₂, —C$_{1-3}$alkyl and —CH₂OH, provided that R¹ and R² are not both H; or R¹ and R², together with the carbon they are bonded to, may form a spiro ring selected from the group consisting of C$_{3-4}$cycloalkyl;

or a salt thereof.

In another embodiment there are provided compounds of the formula I as described according to any of the embodiments above the embodiment above, and wherein n is 0;

or a salt thereof.

In another embodiment there are provided compounds of the formula I as described according to any of the embodiments above the embodiment above, and wherein n is 1;

or a salt thereof.

In another aspect of the invention, there is provided a compound of the general formula I according to any of the embodiments above, or a pharmaceutically acceptable salt thereof for use in a therapeutic method as described hereinbefore and hereinafter Table 1 shows representative compounds of the invention which can be made by the methods described in the general synthetic schemes, the examples, and known methods in the art.

TABLE 1

| Cpd No. | Structure | Cpd Name |
|---|---|---|
| C-AAA | 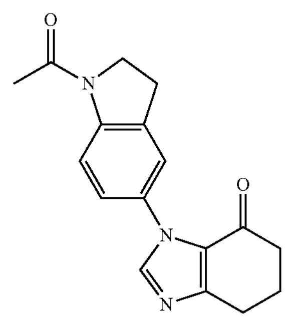 [SMILES: CC(=O)N1CCc2cc(-n3cnc4c3C(=O)CCC4)ccc21] | 3-(1-Acetyl-2,3-dihydro-1H-indol-5-yl)-3,5,6,7-tetrahydro-benzoimidazol-4-one |
| C-AAB | 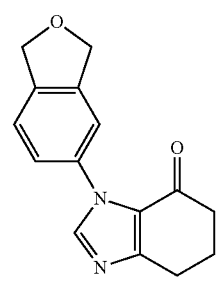 [SMILES: O=C1CCCc2ncn(-c3ccc4c(c3)COC4)c21] | 3-(1,3-Dihydro-isobenzofuran-5-yl)-3,5,6,7-tetrahydro-benzoimidazol-4-one |
| C-AAC | 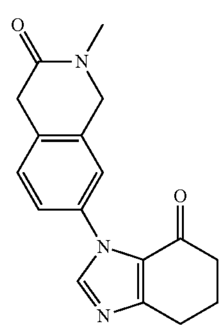 [SMILES: CN1Cc2cc(-n3cnc4c3C(=O)CCC4)ccc2CC1=O] | 2-Methyl-7-(7-oxo-4,5,6,7-tetrahydro-benzoimidazol-1-yl)-1,4-dihydro-2H-isoquinolin-3-one |

TABLE 1-continued

| Cpd No. | Structure | Cpd Name |
|---|---|---|
| C-AAD | 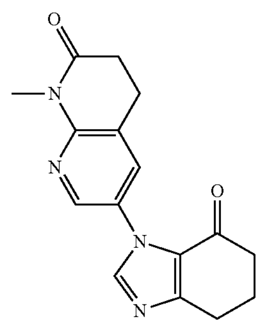 [SMILES: CN1C(=O)CCc2cc(-n3cnc4c3C(=O)CCC4)cnc21] | 1-Methyl-6-(7-oxo-4,5,6,7-tetrahydro-benzoimidazol-1-yl)-3,4-dihydro-1H-[1,8]naphthyridin-2-one |
| C-AAE | 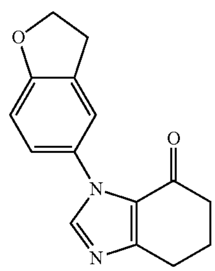 [SMILES: O=C1CCCc2ncn(-c3ccc4c(c3)CCO4)c21] | 3-(2,3-Dihydro-benzofuran-5-yl)-3,5,6,7-tetrahydro-benzoimidazol-4-one |
| C-AAF | 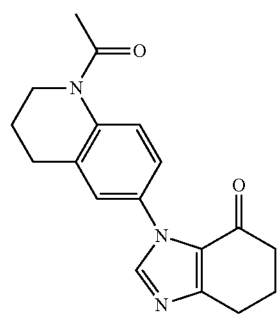 [SMILES: CC(=O)N1CCCc2cc(-n3cnc4c3C(=O)CCC4)ccc21] | 3-(1-Acetyl-1,2,3,4-tetrahydro-quinolin-6-yl)-3,5,6,7-tetrahydro-benzoimidazol-4-one |
| C-AAG | 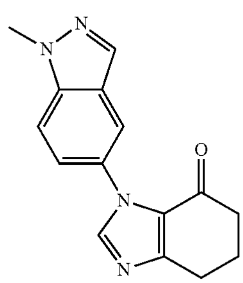 [SMILES: Cn1ncc2cc(-n3cnc4c3C(=O)CCC4)ccc21] | 3-(1-Methyl-1H-indazol-5-yl)-3,5,67,-tetrahydro-benzoimidazol-4-one |
| C-AAH | 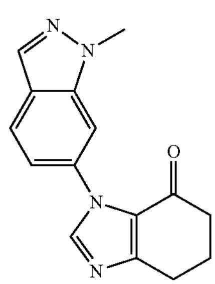 [SMILES: Cn1ncc2ccc(-n3cnc4c3C(=O)CCC4)cc21] | 3-(1-Methyl-1H-indazol-6-yl)-3,5,67,-tetrahydro-benzoimidazol-4-one |

TABLE 1-continued

| Cpd No. | Structure | Cpd Name |
|---|---|---|
| C-AAI | 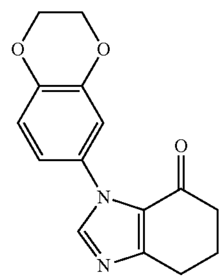 [SMILES: O=C1CCCc2ncn(-c3ccc4c(c3)OCCO4)c21] | 3-(2,3-Dihydro-benzo[1,4]dioxin-6-yl)-3,5,6,7-tetrahydro-benzoimidazol-4-one |
| C-AAJ | 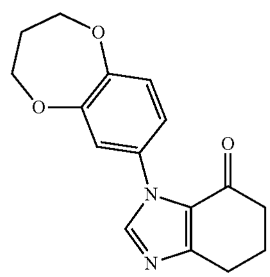 [SMILES: O=C1CCCc2ncn(-c3ccc4c(c3)OCCCO4)c21] | 3-(3,4-Dihydro-2H-benzo[b][1,4]dioxepin-7-yl)-3,5,6,7-tetrahydro-benzoimidazol-4-one |
| C-AAK | 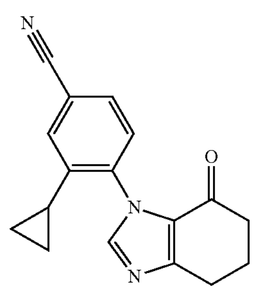 [SMILES: N#Cc1ccc(-n2cnc3c2C(=O)CCC3)c(C2CC2)c1] | 3-Cyclopropyl-4-(7-oxo-4,5,6,7-tetrahydro-benzoimidazol-1-yl)-benzonitrile |
| C-AAL | 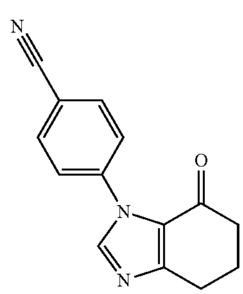 [SMILES: N#Cc1ccc(-n2cnc3c2C(=O)CCC3)cc1] | 4-(7-Oxo-4,5,6,7-tetrahydro-benzoimidazol-1-yl)-benzonitrile |
| C-AAM | 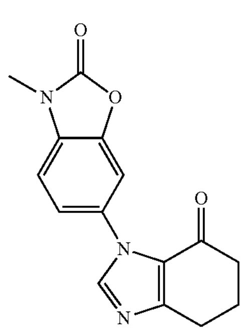 [SMILES: Cn1c(=O)oc2cc(-n3cnc4c3C(=O)CCC4)ccc21] | 3-Methyl-6-(7-oxo-4,5,6,7-tetrahydro-benzoimidazol-1-yl)-3H-benzooxazol-2-one |

TABLE 1-continued

| Cpd No. | Structure | Cpd Name |
| --- | --- | --- |
| C-AAN | 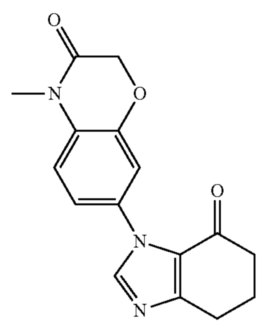 [SMILES: CN1C(=O)COc2cc(-n3cnc4c3C(=O)CCC4)ccc21] | 4-Methyl-7-(7-oxo-4,5,6,7-tetrahydro-benzoimidazol-1-yl)-4H-benzo[1,4]oxazin-3-one |
| C-AAO | 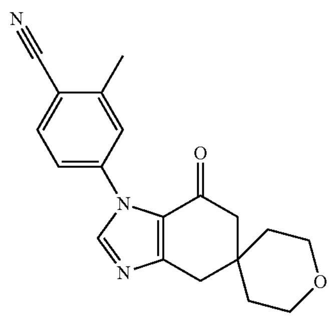 [SMILES: Cc1cc(-n2cnc3c2C(=O)CC2(CCOCC2)C3)ccc1C#N] | 2-Methyl-4-(7-oxospiro[4,6-dihydrobenzoimidazole-5,4'-tetrahydropyran]-1-yl)benzonitrile |
| C-AAP | 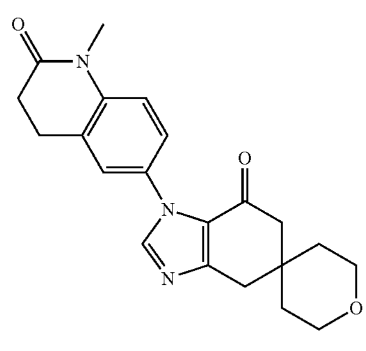 [SMILES: CN1C(=O)CCc2cc(-n3cnc4c3C(=O)CC3(CCOCC3)C4)ccc21] | 3-(1-Methyl-2-oxo-3,4-dihydroquinolin-6-yl)spiro[5,7-dihydrobenzoimidazole-6,4'-tetrahydropyran]-4-one |
| C-AAQ | 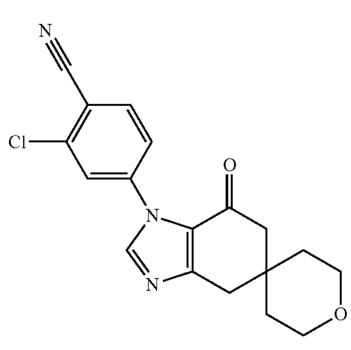 [SMILES: N#Cc1ccc(-n2cnc3c2C(=O)CC2(CCOCC2)C3)cc1Cl] | 3-(3-Chloro-4-cyano-phenyl)-6,6-3-o-tetrahydropyran-3,5,6,7-tetrahydro-benzoimidazol-4-one |

TABLE 1-continued

| Cpd No. | Structure | Cpd Name |
|---|---|---|
| C-AAR | 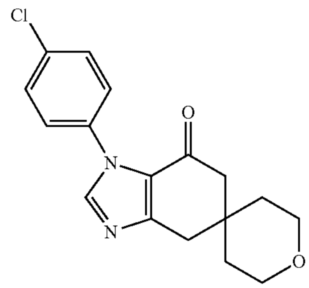 [SMILES: O=C1CC2(CCOCC2)Cc2ncn(-c3ccc(Cl)cc3)c21] | 3-(4-Chloro-phenyl)-6,6-3-o-tetrahydropyran-3,5,6,7-tetrahydro-benzoimidazol-4-one |
| C-AAS | 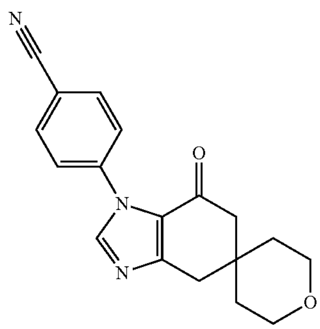 [SMILES: N#Cc1ccc(-n2cnc3c2C(=O)CC2(CCOCC2)C3)cc1] | 4-(7-Oxospiro[4,6-dihydrobenzimidazole-5,4'-tetrahydropyran]-1-yl)benzonitrile |
| C-AAT | 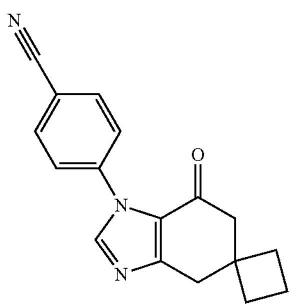 [SMILES: N#Cc1ccc(-n2cnc3c2C(=O)CC2(CCC2)C3)cc1] | 4-(7-Oxospiro[4,6-dihydrobenzimidazole-5,1'-cyclobutan]-1-yl)benzonitrile |
| C-AAU | 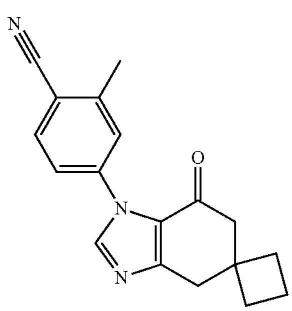 [SMILES: Cc1cc(-n2cnc3c2C(=O)CC2(CCC2)C3)ccc1C#N] | 2-Methyl-4-(7-oxospiro[4,6-dihydrobenzimidazole-5,1'-cyclobutan]-1-yl)benzonitrile |
| C-AAV | 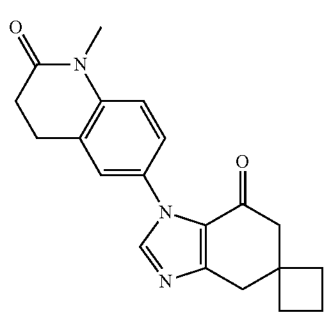 [SMILES: CN1C(=O)CCc2cc(-n3cnc4c3C(=O)CC3(CCC3)C4)ccc21] | 3-(1-Methyl-2-oxo-3,4-dihydroquinolin-6-yl)spiro[5,7-dihydrobenzimidazole-6,1'-cyclobutane]-4-one |

TABLE 1-continued

| Cpd No. | Structure | Cpd Name |
|---|---|---|
| C-AAW | 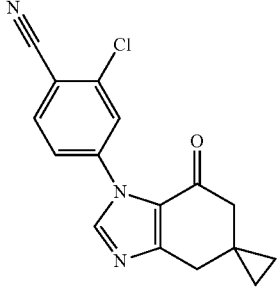 [SMILES: N#Cc1ccc(-n2cnc3c2C(=O)CC2(CC2)C3)cc1Cl] | 3-(3-Chloro-4-cyano)-6,6-spirocyclopropyl-3,5,6,7-tetrahydrobenzimidazol-4-one |
| C-AAX | 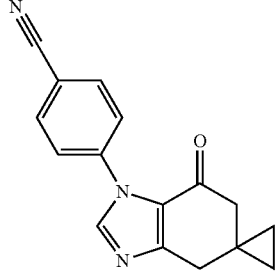 [SMILES: N#Cc1ccc(-n2cnc3c2C(=O)CC2(CC2)C3)cc1] | 3-(4-Cyanophenyl)-6,6-spirocyclpropyl-3,5,6,7-tetrahydro-benzimidazol-4-one |
| C-AAY | 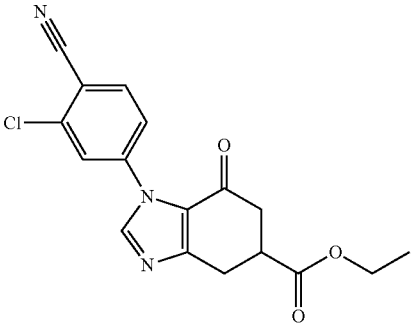 [SMILES: CCOC(=O)C1CC(=O)c2c(ncn2-c2ccc(C#N)c(Cl)c2)C1] | 1-(3-Chloro-4-cyano-phenyl)-7-oxo-4,5,6,7-tetrahydro-1H-benzoimidazole-5-carboxylic acid ethyl ester |
| C-AAZ-A | 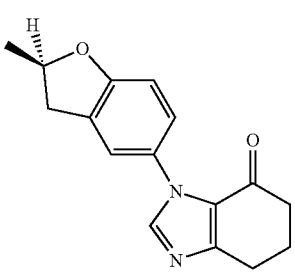 [SMILES: C[C@@H]1Cc2cc(-n3cnc4c3C(=O)CCC4)ccc2O1] | 3-(2-Methyl-2,3-dihydro-benzofuran-5-yl)-3,5,6,7-tetrahydro-benzoimidazol-4-one |
| C-AAZ-B | 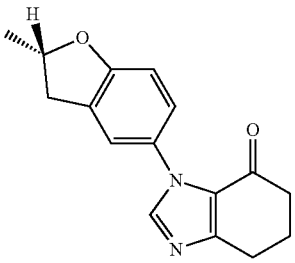 [SMILES: C[C@H]1Cc2cc(-n3cnc4c3C(=O)CCC4)ccc2O1] | 3-(2-Methyl-2,3-dihydro-benzofuran-5-yl)-3,5,6,7-tetrahydro-benzoimidazol-4-one |

TABLE 1-continued

| Cpd No. | Structure | Cpd Name |
| --- | --- | --- |
| C-ABA-A | 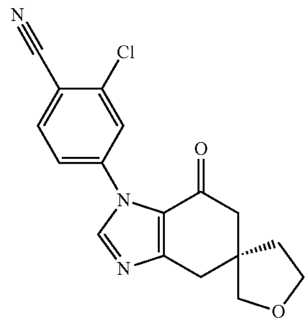 [SMILES: N#Cc1ccc(-n2cnc3c2C(=O)C[C@]2(CCOC2)C3)cc1Cl] | 3-(4-Cyanophenyl)-6,6-(3-tetrahydrofuran)-3,5,6,7-benzimidazolo-4-one |
| C-ABA-B | 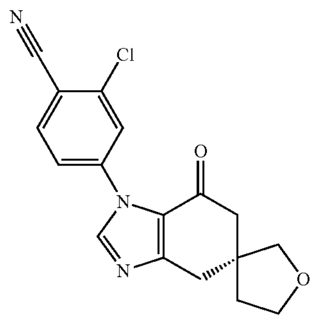 [SMILES: N#Cc1ccc(-n2cnc3c2C(=O)C[C@@]2(CCOC2)C3)cc1Cl] | 3-(4-Cyanophenyl)-6,6-(3-tetrahydrofuran)-3,5,6,7-benzimidiazolo-4-one |
| C-ABB | 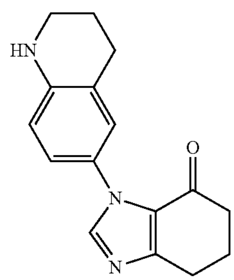 [SMILES: O=C1CCCc2ncn(-c3ccc4c(c3)CCCN4)c21] | 3-(1,2,3,4-Tetrahydro-quinolin-6-yl)-3,5,6,7-tetrahydro-benzoimidazol-4-one |
| C-ABC | 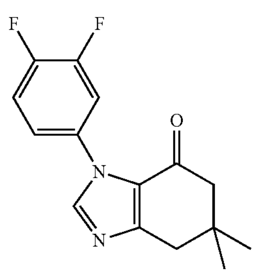 [SMILES: CC1(C)CC(=O)c2c(ncn2-c2ccc(F)c(F)c2)C1] | 3-(3,4-Difluoro-phenyl)-6,6-dimethyl-3,5,6,7-tetrahydro-benzimidazol-4-one |
| C-ABD | 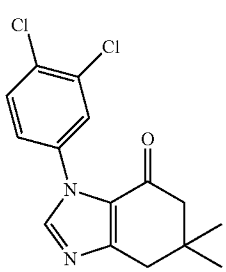 [SMILES: CC1(C)CC(=O)c2c(ncn2-c2ccc(Cl)c(Cl)c2)C1] | 3-(3,4-Dichloro-phenyl)-6,6,-dimethyl-3,5,6,7-tetrahydro-benzoimidazol-4-one |

TABLE 1-continued

| Cpd No. | Structure | Cpd Name |
|---|---|---|
| C-ABE | 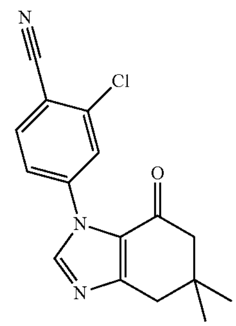 [SMILES: CC1(C)CC(=O)c2c(ncn2-c2ccc(C#N)c(Cl)c2)C1] | 2-Chloro-4-(5,5-dimethyl-7-oxo-4,5,6,7-tetrahydro-benzoimidazol-1-yl)-benzonitrile |
| C-ABF | 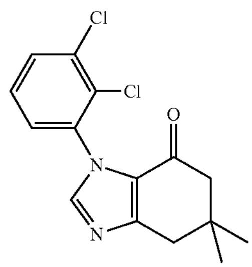 [SMILES: CC1(C)CC(=O)c2c(ncn2-c2cccc(Cl)c2Cl)C1] | 3-(2,3-Dichloro-phenyl)-6,6-dimethyl-3,5,6,7-tetrahydro-benzoimidazol-4-one |
| C-ABG | 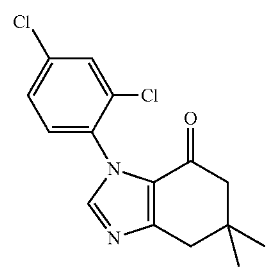 [SMILES: CC1(C)CC(=O)c2c(ncn2-c2ccc(Cl)cc2Cl)C1] | 3-(2,4-Dichloro-phenyl)-6,6-dimethyl-3,5,6,7-tetrahydro-benzoimidazol-4-one |
| C-ABH | 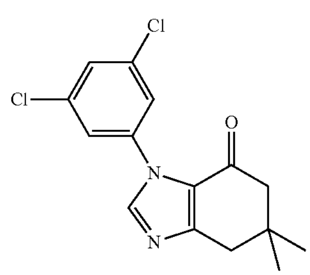 [SMILES: CC1(C)CC(=O)c2c(ncn2-c2cc(Cl)cc(Cl)c2)C1] | 3-(3,5-Dichloro-phenyl)-6,6-dimethyl-3,5,6,7-tetrahydro-benzoimidazol-4-one |
| C-ABI | 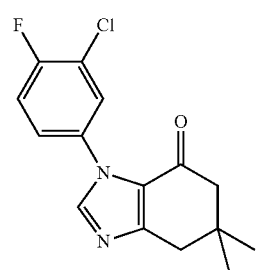 [SMILES: CC1(C)CC(=O)c2c(ncn2-c2ccc(F)c(Cl)c2)C1] | 3-(3-Chloro-4-fluoro-phenyl)-6,6-dimethyl-3,5,6,7-tetrahydro-benzoimidazol-4-one |

TABLE 1-continued

| Cpd No. | Structure | Cpd Name |
|---|---|---|
| C-ABJ | 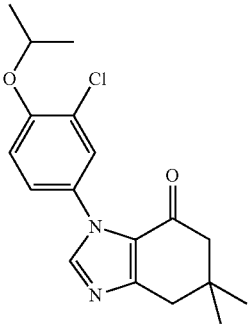 [SMILES: CC(C)Oc1ccc(-n2cnc3c2C(=O)CC(C)(C)C3)cc1Cl] | 3-(3-Chloro-4-isopropoxy-phenyl)-6,6-dimethyl-3,5,6,7-tetrahydro-benzoimidazol-4-one |
| C-ABK | 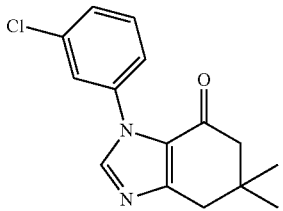 [SMILES: CC1(C)CC(=O)c2c(ncn2-c2cccc(Cl)c2)C1] | 3-(3-Chloro-phenyl)-6,6-dimethyl-3,5,6,7-tetrahydro-benzoimidazol-4-one |
| C-ABL | 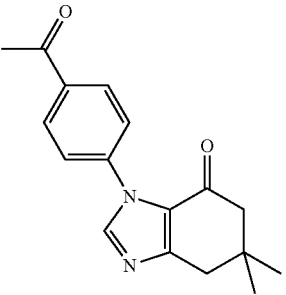 [SMILES: CC(=O)c1ccc(-n2cnc3c2C(=O)CC(C)(C)C3)cc1] | 3-(4-Acetyl-phenyl)-6,6-dimethyl-3,5,6,7-tetrahydro-benzoimidazol-4-one |
| C-ABM | 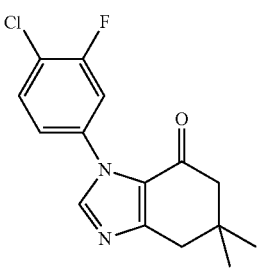 [SMILES: CC1(C)CC(=O)c2c(ncn2-c2ccc(Cl)c(F)c2)C1] | 3-(4-Chloro-3-fluoro-phenyl)-6,6-dimethyl-3,5,6,7-tetrahydro-benzoimidazol-4-one |
| C-ABN | 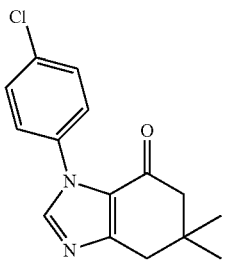 | 3-(4-Chloro-phenyl)-6,6-dimethyl-3,5,6,7-tetrahydro-benzoimidazol-4-one |

TABLE 1-continued

| Cpd No. | Structure | Cpd Name |
|---|---|---|
| C-ABO | 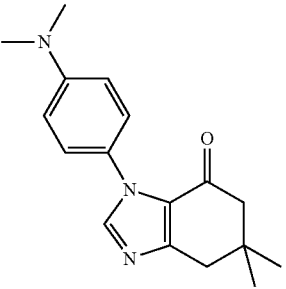 | 3-(4-Dimethylamino-phenyl)-6,6-dimethyl-3,5,6,7-tetrahydro-benzoimidazol-4-one |
| C-ABP | 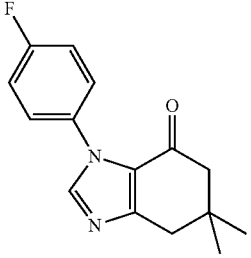 | 3-(4-Fluoro-phenyl)-6,6-dimethyl-3,5,6,7-tetrahydro-benzoimidazol-4-one |
| C-ABQ | 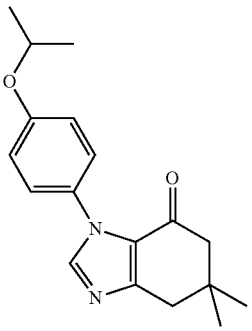 [SMILES: CC(C)Oc1ccc(-n2cnc3c2C(=O)CC(C)(C)C3)cc1] | 3-(4-Isoporopoxy-phenyl)-6,6-dimethyl-3,5,6,7-tetrahydro-benzoimidazol-4-one |
| C-ABR | 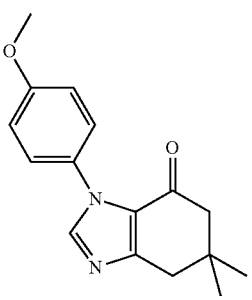 [SMILES: COc1ccc(-n2cnc3c2C(=O)CC(C)(C)C3)cc1] | 3-(4-Methoxy-phenyl)-6,6-dimethyl-3,5,6,7-tetrahydro-benzoimidazol-4-one |
| C-ABS | 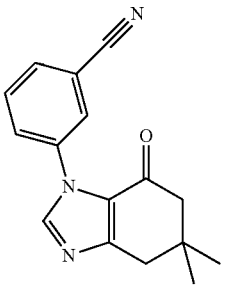 | 3-(5,5-Dimethyl-7-oxo-4,5,6,7-tetrahydro-benzoimidazol-1-yl)-benzonitrile |

TABLE 1-continued

| Cpd No. | Structure | Cpd Name |
|---|---|---|
| C-ABT | 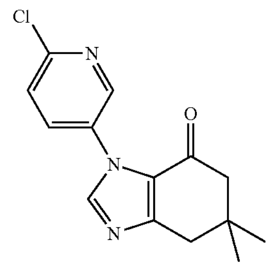 [SMILES: CC1(C)CC(=O)c2c(ncn2-c2ccc(Cl)nc2)C1] | 3-(6-Chloro-pyridin-3-yl)-6,6-dimethyl-3,5,6,7-tetrahydro-benzoimidazol-4-one |
| C-ABU | 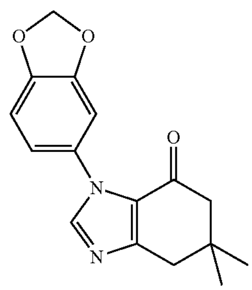 [SMILES: CC1(C)CC(=O)c2c(ncn2-c2ccc3c(c2)OCO3)C1] | 3-Benzo[1,3]dioxol-5-yl-6,6-dimethyl-3,5,6,7-tetrahydro-benzoimidazol-4-one |
| C-ABV | 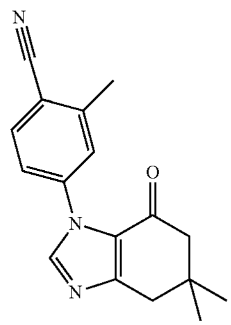 | 4-(5,5-Dimethyl-7-oxo-4,5,6,7-tetrahydro-benzoimidazol-1-yl)-2-methyl-benzonitrile |
| C-ABW | 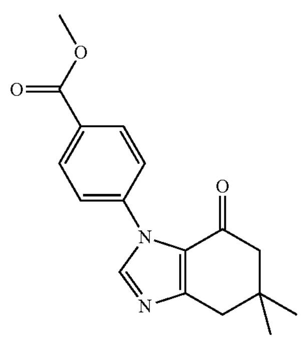 [SMILES: COC(=O)c1ccc(-n2cnc3c2C(=O)CC(C)(C)C3)cc1] | 4-(5,5-Dimethyl-7-oxo-4,5,6,7-tetrahydro-benzoimidazol-1-yl)-benzoic acid methyl ester |
| C-ABX | 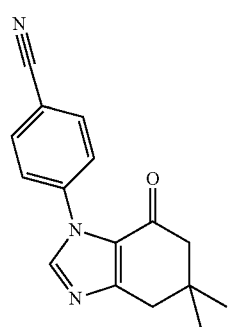 | 4-(5,5-Dimethyl-7-oxo-4,5,6,7-tetrahydro-benzoimidazol-1-yl)-benzonitrile |

TABLE 1-continued

| Cpd No. | Structure | Cpd Name |
|---|---|---|
| C-ABY | 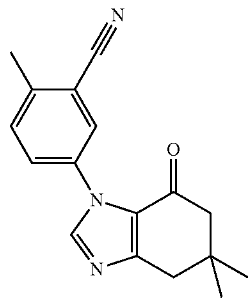 [SMILES: Cc1ccc(-n2cnc3c2C(=O)CC(C)(C)C3)cc1C#N] | 5-(5,5-Dimethyl-7-oxo-4,5,6,7-tetrahydro-benzoimidazol-1-yl)-2-methyl-benzonitrile |
| C-ABZ | 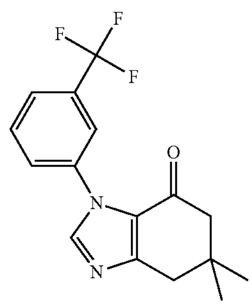 [SMILES: CC1(C)CC(=O)c2c(ncn2-c2cccc(C(F)(F)F)c2)C1] | 6,6-Dimethyl-3-(3-trifluoromethyl-phenyl)-3,5,6,7-tetrahydro-benzoimidazol-4-one |
| C-ACA | 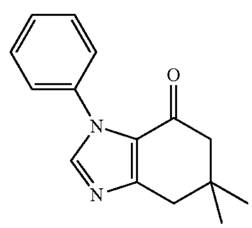 [SMILES: CC1(C)CC(=O)c2c(ncn2-c2ccccc2)C1] | 6,6-Dimethyl-3-phenyl-3,5,6,7-tetrahydro-benzoimidazol-4-one |
| C-ACB | 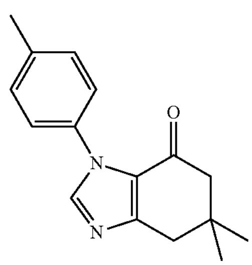 [SMILES: Cc1ccc(-n2cnc3c2C(=O)CC(C)(C)C3)cc1] | 6,6-Dimethyl-3-p-tolyl-3,5,6,7-tetrahydro-benzoimidazol-4-one |
| C-ACC | 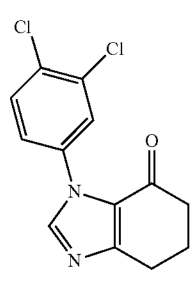 | 3-(3,4-Dichloro-phenyl)-3,5,6,7-tetrahydro-benzoimidazol-4-one |

TABLE 1-continued

| Cpd No. | Structure | Cpd Name |
|---|---|---|
| C-ACD | 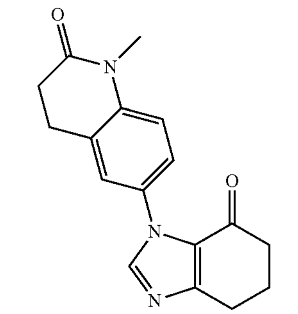 | 1-Methyl-6-(7-oxo-4,5,6,7-tetrahydro-benzoimidazol-1-yl)-3,4-dihydro-1H-quinolin-2-one |
| C-ACE | 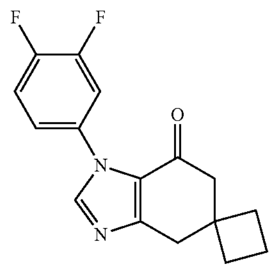 [SMILES: O=C1CC2(CCC2)Cc2ncn(-c3ccc(F)c(F)c3)c21] | 3-(3,4-Difluoro-phenyl)-6,6-spirocyclopropyl-3,5,6,7-tetrahydro-benzimidazolo-4-one |
| C-ACF | 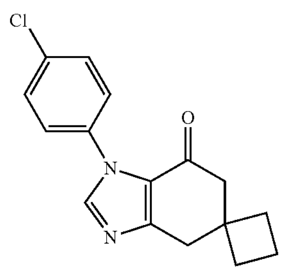 [SMILES: O=C1CC2(CCC2)Cc2ncn(-c3ccc(Cl)cc3)c21] | 3-(4-Chloroophenyl)-6,6-spirocyclopropyl-3,5,6,7-tetrahydro-benzimidazolo-4-one |
| C-ACG | 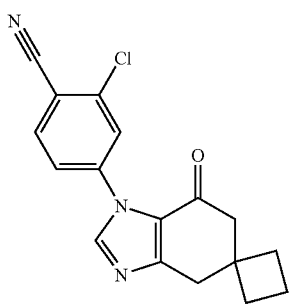 [SMILES: N#Cc1ccc(-n2cnc3c2C(=O)CC2(CCC2)C3)cc1Cl] | 3-(4-Cyano, 3-chlorophenyl)-6,6-spirocyclobutyl-3,5,6,7-benzimidazolo-4-one |
| C-ACH | 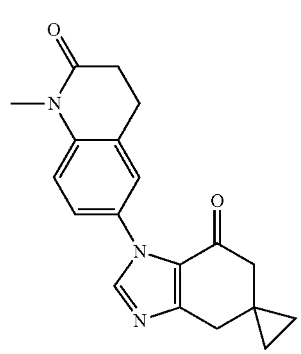 [SMILES: CN1C(=O)CCc2cc(-n3cnc4c3C(=O)CC3(CC3)C4)ccc21] | 3-(1-Methyl-2-oxo-3,4-dihydroquinolin-6-yl)spiro[5,7-dihydrobenzimidazole-6,1'-cyclopropane]-4-one |

TABLE 1-continued

| Cpd No. | Structure | Cpd Name |
| --- | --- | --- |
| C-ACI | 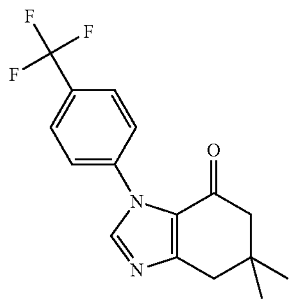 [SMILES: CC1(C)CC(=O)c2c(ncn2-c2ccc(C(F)(F)F)cc2)C1] | 6,6-Dimethyl-3-(4-trifluoromethyl-phenyl)-3,5,6,7-tetrahydro-benzoimidazol-4-one |
| C-ACJ | 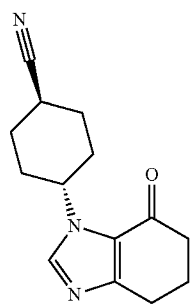 [SMILES: C[C@]1(C#N)CC[C@H](n2cnc3c2C(=O)CCC3)CC1] | trans-4-(7-Oxo-5,6-dihydro-4H-benzimidazol-1-yl)cyclohexanecarbonitrile |
| C-ACK | 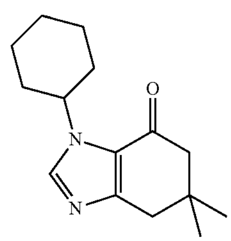 | 3-Cyclohexyl-6,6-dimethyl-3,5,6,7etrahydro-benzoimidazol-4-one |
| C-ACL | 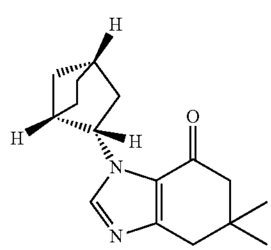 [SMILES: CC1(C)CC(=O)c2c(ncn2[C@H]2C[C@@H]3CC[C@H]2C3)C1] | 3-(1S,2S,3R)-Bicyclo[2.2.1]hept-2-1-6,6-dimethyl-3,5,6,7-tetrahydro-benzoimidazol-4-one |
| C-ACM | 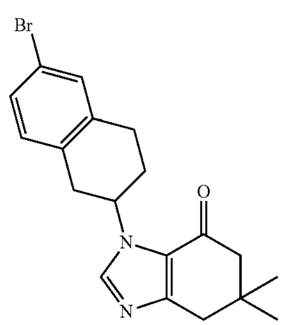 | 3-(6-Bromo-1,2,3,4-tetrahydro-naphthalen-2-yl)-6,6-dimethyl-3,5,6,7-tetrahydro-benzoimidazol-4-on |

TABLE 1-continued

| Cpd No. | Structure | Cpd Name |
|---|---|---|
| C-ACN | 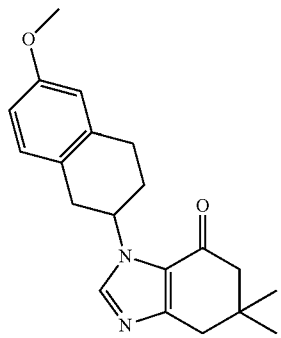 | 3-(6-Methoxy-1,2,3,4-tetrahydro-naphthalen-2-yl)-6,6-dimethyl-3,5,6,7-tetrahydro-benzoimidazol-4-one |
| C-ACO | 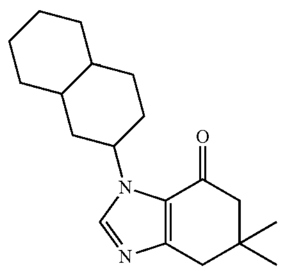 [SMILES: CC1(C)CC(=O)c2c(ncn2C2CCC3(C)CCCCC3C2)C1] | 3-(Decahydro-naphthalen-2-yl)-6,6-dimethyl-3,5,6,7-tetrahydro-benzoimdazol-4-one |
| C-ACP | 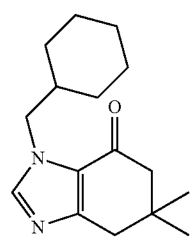 [SMILES: CC1(C)CC(=O)c2c(ncn2CC2CCCCC2)C1] | 3-Cyclohexylmethyl-6,6-dimethyl-3,5,6,7-tetrahydro-benzoimidazol-4-one |
| C-ACQ | 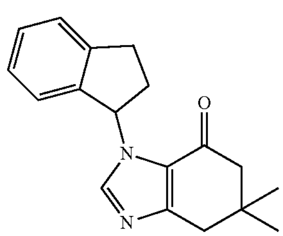 [SMILES: CC1(C)CC(=O)c2c(ncn2C2CCc3ccccc32)C1] | 3-Indan-1-yl-6,6-dimethyl-3,5,6,7-tetrahydro-benzoimidazol-4-one |
| C-ACR | 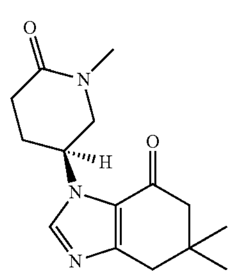 | 6,6-Dimethyl-3-((S)-1-methyl-6-oxo-piperidin-3-yl)-3,5,6,7-tetrahydrobenzoimidazol-4-one |

TABLE 1-continued

| Cpd No. | Structure | Cpd Name |
|---|---|---|
| C-ACS | 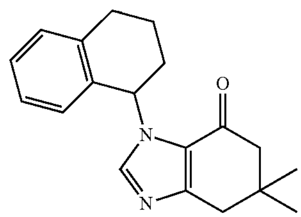 [SMILES: CC1CCC(n2cnc3c2C(=O)CC(C)(C)C3)c2ccccc21] | 6,6-Dimethyl-3-(1,2,3,4-tetrahydronaphthalen-1-yl)-3,5,6,7-tetrahydro-benzoimidazol-4-one |
| C-ACT | 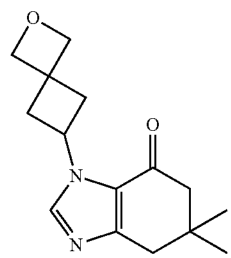 [SMILES: CC1(C)CC(=O)c2c(ncn2C2CC3(COC3)C2)C1] | 6,6-Dimethyl-3-(2-oxa-spiro[3.3]hept-6-yl)-3,5,6,7-tetrahydro-benzoimidazol-4-one |
| C-ACU | 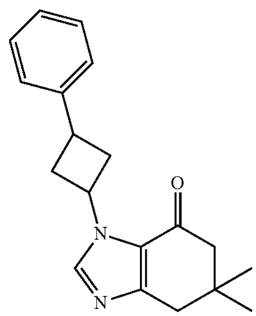 [SMILES: CC1(C)CC(=O)c2c(ncn2C2CC(c3ccccc3)C2)C1] | 6,6-Dimethyl-3-(3-phenyl-cyclobutyl)-3,5,6,7-tetrahydro-benzoimidazol-4-one |
| C-ACV | 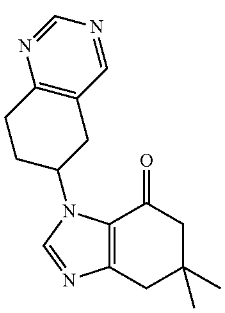 [SMILES: CC1(C)CC(=O)c2c(ncn2C2CCc3ncncc3C2)C1] | 6,6-Dimethyl-3-(5,6,7,8-tetrahydro-quinazolin-6-yl)-3,5,6,7-tetrahydro-benzoimidazol-4-one |
| C-ACW | 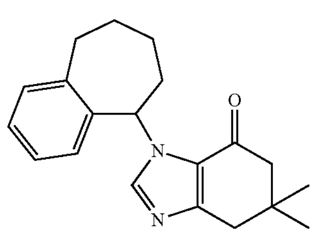 [SMILES: CC1(C)CC(=O)c2c(ncn2C2CCCCc3ccccc32)C1] | 6,6-Dimethyl-3-(6,7,8,9-tetrahydro-5H-benzocyclohepten-5-yl)-3,5,6,7-tetrahydro-benzoimidazol-4-one |

TABLE 1-continued

| Cpd No. | Structure | Cpd Name |
|---|---|---|
| C-ACX | 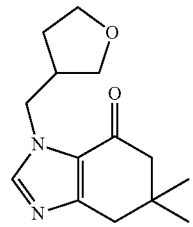 [SMILES: CC1(C)CC(=O)c2c(ncn2CC2CCOC2)C1] | 6,6-Dimethyl-3-(tetrahydro-furan-3-ylmethyl)-3,5,6,7-tetrahydro-benzoimidazol-4-one |
| C-ACY | 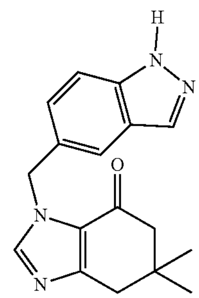 [SMILES: CC1(C)CC(=O)c2c(ncn2Cc2ccc3[nH]ncc3c2)C1] | 3-(1H-Indazol-5-ylmethyl)-6,6-dimethyl-3,5,6,7-tetrahydro-benzoimidazol-4-one |
| C-ACZ | 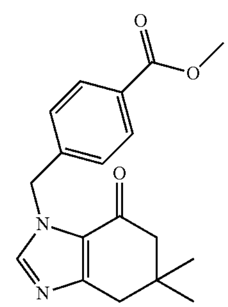 [SMILES: COC(=O)c1ccc(Cn2cnc3c2C(=O)CC(C)(C)C3)cc1] | 4-(5,5-Dimethyl-7-oxo-4,5,6,7-tetrahydro-benzoimidazol-1-ylmethyl)-benzoic acid methyl ester |
| C-ADA | 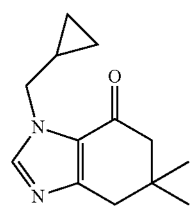 [SMILES: CC1(C)CC(=O)c2c(ncn2CC2CC2)C1] | 3-Cyclopropylmethyl-6,6-dimethyl-3,5,6,7-tetrahydro-benzoimidazol-4-one |
| C-ADB | 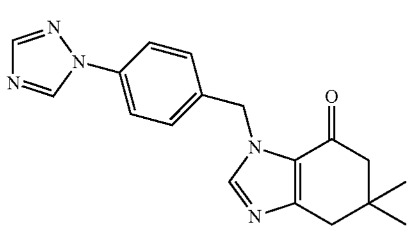 [SMILES: CC1(C)CC(=O)c2c(ncn2Cc2ccc(-n3cncn3)cc2)C1] | 6,6-Dimethyl-3-(4-[1,2,4]triazol-1-yl-benzyl)-3,5,6,7-tetrahydro-benzoimidazol-4-one |
| C-ADC | 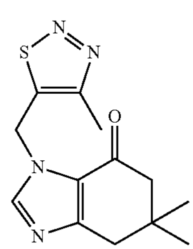 [SMILES: Cc1nnsc1Cn1cnc2c1C(=O)CC(C)(C)C2] | 6,6-Dimethyl-3-(4-methyl-[1,2,3]thiadiazol-5-ylmethyl)-3,5,6,7-tetrahydro-benzoimidazol-4-one |

TABLE 1-continued

| Cpd No. | Structure | Cpd Name |
|---|---|---|
| C-ADD | 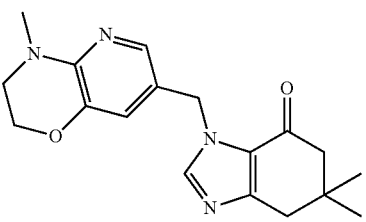 [SMILES: CN1CCOc2cc(Cn3cnc4c3C(=O)CC(C)(C)C4)cnc21] | 6,6-Dimethyl-3-(4-methyl-3,4-dihydro-2H-pyrido[3,2-b][1,4]oxazin-7-ylmethyl)-3,5,6,7-tetrahydro-benzoimidazol-4-one |
| C-ADE | 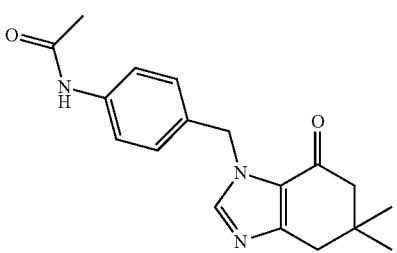 [SMILES: CC(=O)Nc1ccc(Cn2cnc3c2C(=O)CC(C)(C)C3)cc1] | N-[4-(5,5-Dimethyl-7-oxo-4,5,6,7-tetrahydro-benzoimidazol-1-ylmethyl)-phenyl]-acetamide |
| C-ADF | 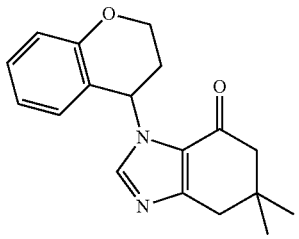 [SMILES: CC1(C)CC(=O)c2c(ncn2C2CCOc3ccccc32)C1] | 3-Chroman-4-yl-6,6-dimethyl-3,5,6,7-tetrahydro-benzoimidazol-4-one |
| C-ADG | 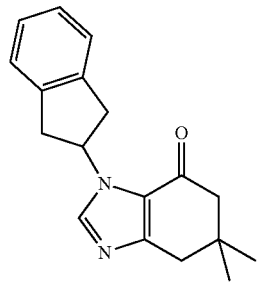 [SMILES: CC1(C)CC(=O)c2c(ncn2C2Cc3ccccc3C2)C1] | 3-Indan-4-yl-6,6-dimethyl-3,5,6,7-tetrahydro-benzoimidazol-4-one |
| C-ADH | 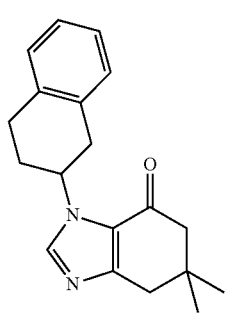 [SMILES: CC1(C)CC(=O)c2c(ncn2C2CCc3ccccc3C2)C1] | 6,6-Dimethyl-3-(1,2,3,4-tetrahydro-naphthalen-2-yl)-3,5,6,7-tetrahydro-benzoimidazol-4-one |

TABLE 1-continued

| Cpd No. | Structure | Cpd Name |
|---|---|---|
| C-ADI | 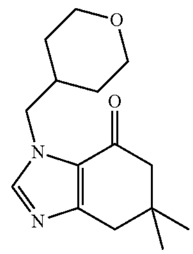 [SMILES: CC1(C)CC(=O)c2c(ncn2CC2CCOCC2)C1] | 6,6-Dimethyl-3-(tetrahydro-pyran-4-ylmethyl)-3,5,6,7-tetrahydro-benzoimidazol-4-one |
| C-ADJ | 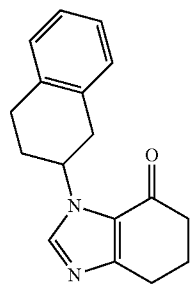 | 3-(1,2,3,4-Tetrahydro-naphthalen-2-yl)-3,5,6,7-tetrahydro-benzoimidazol-4-one |
| C-ADK | 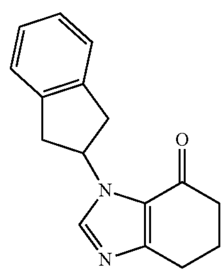 [SMILES: O=C1CCCc2ncn(C3Cc4ccccc4C3)c21] | 3-Indan-2-yl-3,5,6,7-tetrahydro-benzoimidazol-4-one |
| C-ADL | 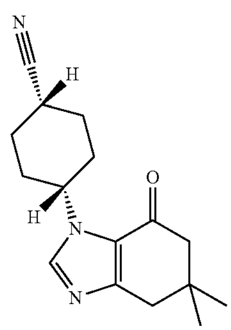 | 4-(5,5-Dimethyl-7-oxo-4,5,6,7-tetrahydro-benzoimidazol-1-yl)-cyclohexanecarbonitrile |
| C-ADM | 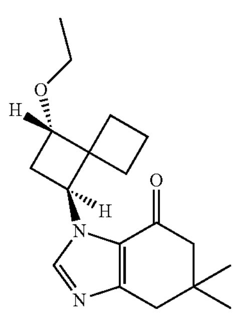 [SMILES: CCO[C@H]1C[C@H](n2cnc3c2C(=O)CC(C)(C)C3)C12CCC2] | 3-((1S,3S)-3-Ethoxy-spiro[3.3]hept-1-yl)-6,6-dimethyl-3,5,6,7-tetrahydro-benzoimidazol-4-one |

TABLE 1-continued

| Cpd No. | Structure | Cpd Name |
|---|---|---|
| C-ADN | 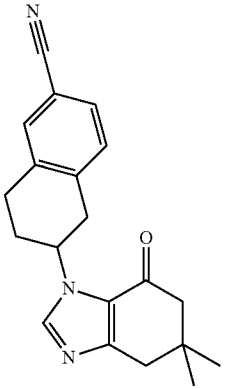 | 6-(5,5-Dimethyl-7-oxo-4,5,6,-tetrahydro-benzoimidazol-1-yl)-5,6,7,8-tetrahydro-naphthalene-2-carbonitrile |
| C-ADO | 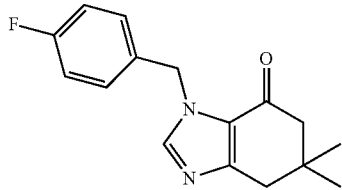 [SMILES: CC1(C)CC(=O)c2c(ncn2Cc2ccc(F)cc2)C1] | 3-(4-Fluoro-benzyl)-6,6-dimethyl-3,5,6,7-tetrahydro-benzoimidazol-4-one |
| C-ADP | 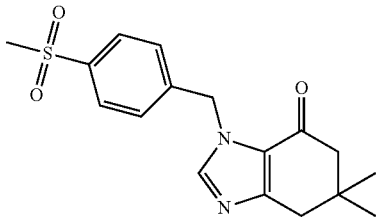 | 3-(4-Methanesulfonyl-benzyl)-6,6-dimethyl-3,5,6,7-tetrahydro-benzoimidazol-4-one |
| C-ADQ | 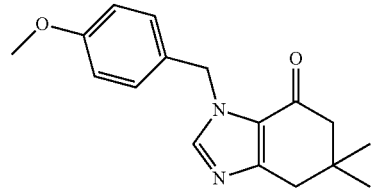 | 3-(4-Methoxy-benzyl)-6,6-dimethyl-3,5,6,7-tetrahydro-benzoimidazol-4-one |
| C-ADR | 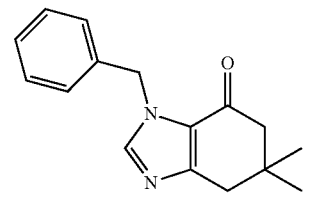 [SMILES: CC1(C)CC(=O)c2c(ncn2Cc2ccccc2)C1] | 3-Benzyl-6,6-dimethyl-3,5,6,7-tetrahydro-benzoimidazol-4-one |
| C-ADS | 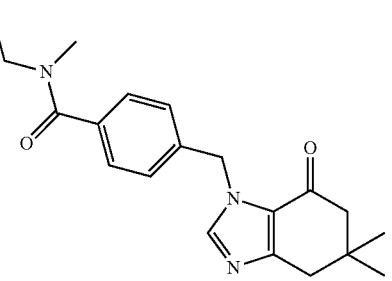 | 4-(5,5-Dimethyl-7-oxo-4,5,6,7-tetrahydro-benzoimidazol-1-ylmethyl)-N-(2-hydroxy-ethyl)-N-methyl-benzamide |

TABLE 1-continued

| Cpd No. | Structure | Cpd Name |
|---|---|---|
| C-ADT | 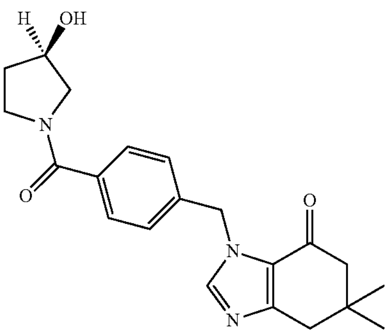 [SMILES: CC1(C)CC(=O)c2c(ncn2Cc2ccc(C(=O)N3CC[C@@H](O)C3)cc2)C1] | 3-[4-((R)-3-Hydroxy-pyrrolidine-1-carbonyl)-benzyl]-6,6-dimethyl-3,5,6,7-tetrahydro-benzoimidazol-4-one |
| C-ADU | 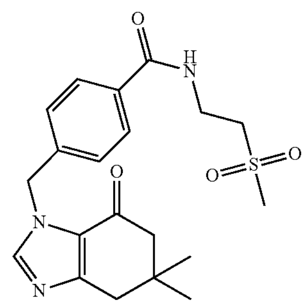 [SMILES: CC1(C)CC(=O)c2c(ncn2Cc2ccc(C(=O)NCCS(C)(=O)=O)cc2)C1] | 4-(5,5-Dimethyl-7-oxo-4,5,6,7-tetrahydro-benzoimidazol-1-ylmethyl)-N-(2-methanesulfonyl-ethyl)-benzamide |
| C-ADV | 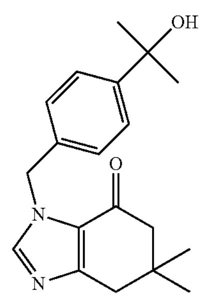 [SMILES: CC1(C)CC(=O)c2c(ncn2Cc2ccc(C(C)(C)O)cc2)C1] | 3-[4-(1-Hydroxy-1-methyl-ethyl)-benzyl]-6,6-dimethyl-3,5,6,7-tetrahydro-benzoimidazol-4-one |
| C-ADW | 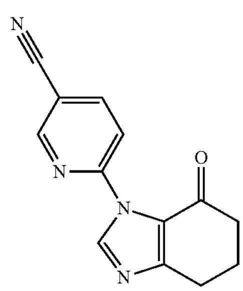 [SMILES: N#Cc1ccc(-n2cnc3c2C(=O)CCC3)nc1] | 6-(7-Oxo-4,5,6,7-tetrahydro-benzoimidazol-1-yl)-nicotinonitrile |
| C-ADX | 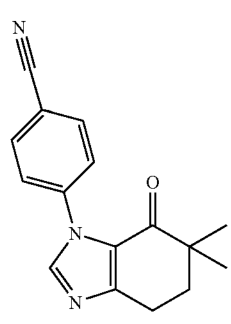 | 4-(6,6-Dimethyl-7-oxo-4,5,6,7-tetrahydro-benzoimidazol-1-yl)-benzonitrile |

TABLE 1-continued

| Cpd No. | Structure | Cpd Name |
| --- | --- | --- |
| C-ADY | 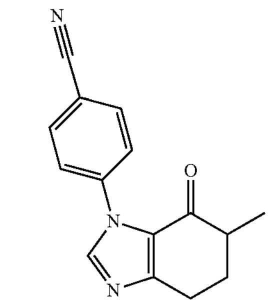 | 4-(6-Methyl-7-oxo-4,5,6,7-tetrahydro-benzoimidazol-1-yl)-benzonitrile |
| C-ADZ | 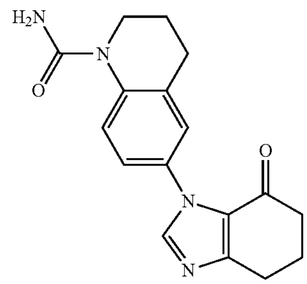 [SMILES: NC(=O)N1CCCc2cc(-n3cnc4c3C(=O)CCC4)ccc21] | 6-(7-Oxo-4,5,6,7-tetrahydro-benzoimidazol-1-yl)-3,4-dihydro-2H-quinoline-1-carboxylic acid amide |
| C-AEA | 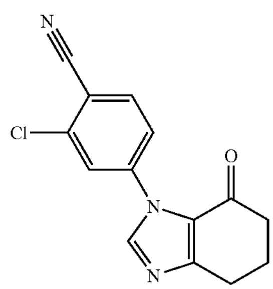 [SMILES: N#Cc1ccc(-n2cnc3c2C(=O)CCC3)cc1Cl] | 2-Chloro-4-(7-oxo-4,5,6,7-tetrahydro-benzoimidazol-1-yl)-benzonitrile |
| C-AEB-A | 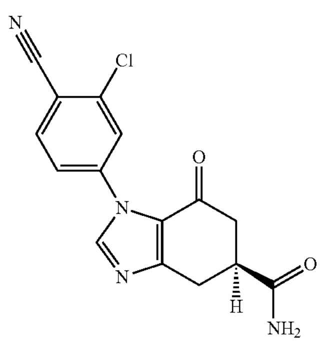 [SMILES: N#Cc1ccc(-n2cnc3c2C(=O)C[C@@H](C(N)=O)C3)cc1Cl] | (S)-1-(3-Chloro-4-cyano-phenyl)-7-oxo-4,5,6,7-tetrahydro-1H-benzoimidazole-5-carboxylic acid amide |
| C-AEB-B | 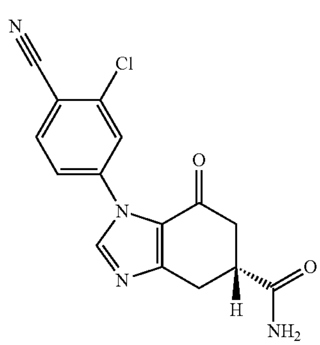 [SMILES: N#Cc1ccc(-n2cnc3c2C(=O)C[C@H](C(N)=O)C3)cc1Cl] | (R)-1-(3-Chloro-4-cyano-phenyl)-7-oxo-4,5,6,7-tetrahydro-1H-benzoimidazole-5-carboxylic acid amide |

TABLE 1-continued

| Cpd No. | Structure | Cpd Name |
|---|---|---|
| C-AED | 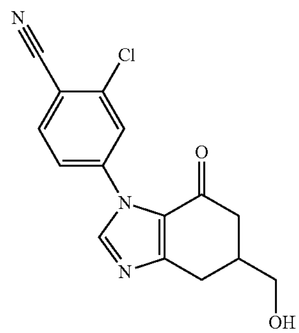 [SMILES: N#Cc1ccc(-n2cnc3c2C(=O)CC(CO)C3)cc1Cl] | 2-Chloro-4-(5-hydroxymethyl-7-oxo-4,5,6,7-tetrahydro-benzoimidazol-1-yl)-benzonitrile |
| C-AEE | 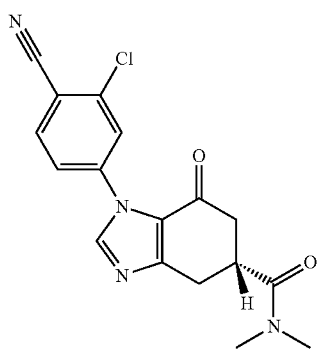 [SMILES: CN(C)C(=O)[C@H]1CC(=O)c2c(ncn2-c2ccc(C#N)c(Cl)c2)C1] | (R)-1-(3-Chloro-4-cyano-phenyl)-7-oxo-4,5,6,7-tetrahydro-1H-benzoimidazole-5-carboxylic acid dimethylamide |
| C-AEF | 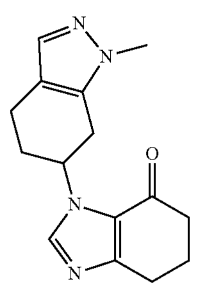 [SMILES: Cn1ncc2c1CC(n1cnc3c1C(=O)CCC3)CC2] | 3-(1-Methyl-4,5,6,7-tetrahydro-1H-indazol-6-yl)-3,5,6,7-tetrahydro-benzoimidazol-4-one |
| C-AEG | 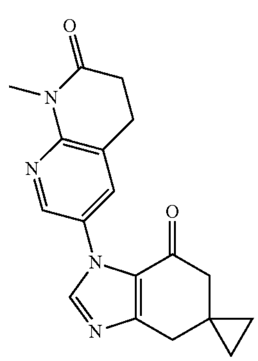 | 6-(5,5-Dimethyl-7-oxo-4,5,6,7-tetrahydro-benzimidazol-1-yl)-1-methyl-3,4-dihydro-1H-[1,8]naphthyridin-2-one |

TABLE 1-continued

| Cpd No. | Structure | Cpd Name |
|---|---|---|
| C-AEH | 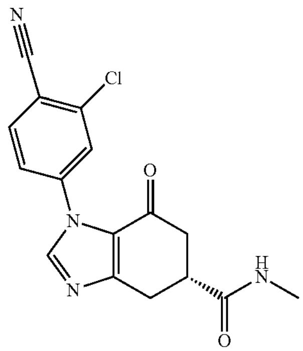 | (R)-1-(3-Chloro-4-cyano-phenyl)-7-oxo-4,5,6,7-tetrahydro-1H-benzoimidazole-5-carboxylic acid methylamide |

In one embodiment, the invention relates to the compounds depicted in Table 1 above and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds of formula (I) can exist in more than one tautomeric form. The invention includes methods for using all such tautomers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure.

All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2$—$CH_2)$—, —$(CH_2$—$CH_2$—$CH(CH_3))$—, —$(CH_2$—$CH(CH_3)$—$CH_2)$—, —$(CH(CH_3)$—$CH_2$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CHCH(CH_3)_2)$— and —$C(CH_3)(CH_2CH_3)$—.

The term "$C_{3-n}$-cycloalkyl", wherein n is an integer 4 to n, either alone or in combination with another radical denotes a cyclic, saturated, unbranched hydrocarbon radical with 3 to n C atoms.

For example the term $C_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo [2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —$CH_2CHF_2$, —$CF_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—$R_a$ may be represented as phenyl-S(O)$_m$— when $R_a$ is phenyl and where m is 0, 1 or 2.

GENERAL SYNTHETIC METHODS

The compounds of the invention may be prepared by the methods and examples presented below and methods known to those of ordinary skill in the art. The methods that are described here are intended as an illustration and for the enablement of the instant invention without restricting the scope of its subject matter, the claimed compounds, and the examples. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

Intermediates and compounds of the invention may be prepared by the general methods described below.

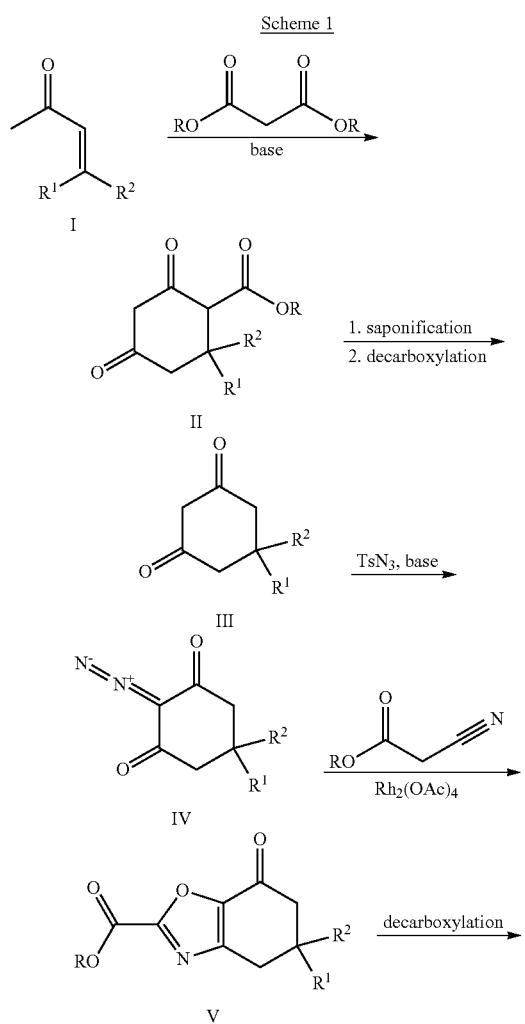

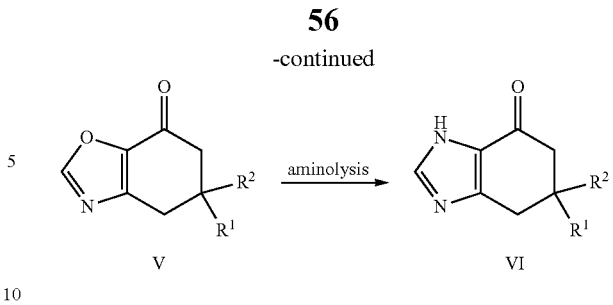

Preparation of the optionally substituted intermediate VI is prepared as described in Scheme 1. Intermediate I is reacted with a dialkyl malonate in the presence of a suitable base to provide intermediate II. Hydrolysis and decarboxylation of II provides III. Reaction of III with $TsN_3$ in the presence of a suitable base provides IV. Reaction of IV with 3-oxo-butyronitrile, in the presence of a suitable catalyst such as $Rh_2(OAc)_4$ provides V. Hydrolysis and decarboxylation provides V. The desired intermediate VI is prepared by subjecting V to aminolysis.

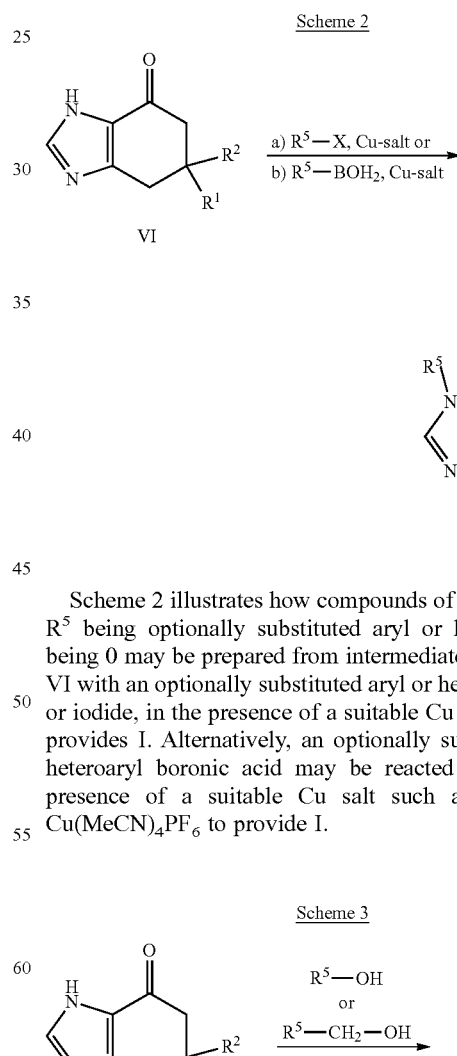

Scheme 2 illustrates how compounds of formula I having $R^5$ being optionally substituted aryl or heteroaryl and n being 0 may be prepared from intermediate VI. Reaction of VI with an optionally substituted aryl or heteroaryl bromide or iodide, in the presence of a suitable Cu salt such as CuI, provides I. Alternatively, an optionally substituted aryl or heteroaryl boronic acid may be reacted with VI in the presence of a suitable Cu salt such as $Cu(OAc)_2$ or $Cu(MeCN)_4PF_6$ to provide I.

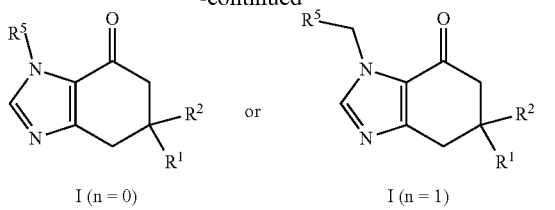

Scheme 3 illustrates how compounds of formula I having $R^5$ being optionally substituted carbocyclic or heterocyclic and n being 0 or 1 may be prepared from intermediate VI. The compounds may be prepared by reaction of VI with an optionally substituted, hydroxy carbocyclic or heterocyclic ring (n=0) or hydroxymethyl carbocyclic or heterocyclic ring (n=1) under Mitsunobu conditions. Compounds of formula I having $R^5$ being optionally substituted aryl or heteroaryl and n being 1 may be prepared by the same method, using an optionally substituted, hydroxymethyl aryl or heteroaryl compound.

Scheme 4

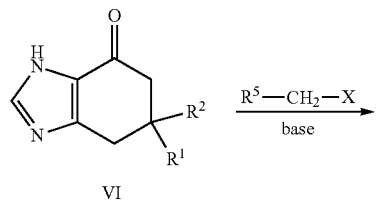

Scheme 4 illustrates an alternate method for preparing compounds having n=1. An optionally substituted halomethyl carbocycle, heterocycle, aryl or heteroaryl may be reacted with VI in the presence of a suitable base to provide I (n=1).

SYNTHETIC EXAMPLES

Final compounds are designated by compound labels corresponding to the compound labels in Table 1. Labels for intermediates begin with "I-" or "N-" for example I-AAA or N-0001. Compounds that are resolved by chiral HPLC are done so by the conditions described in the Examples below. The first to elute is designated enantiomer A, and the second to elute is enantiomer B.

Synthesis of Intermediates

Synthesis of 3-oxaspiro[5.5]undecane-8,10-dione (I-AAA)

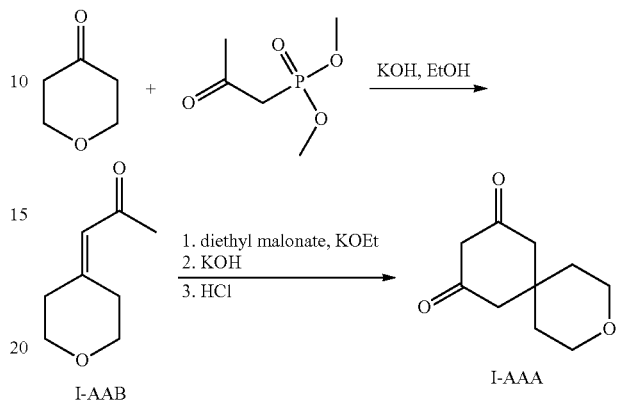

To a 0° C. mixture of 1.4 g (25 mmol) of KOH in 48 mL of $H_2O$ and 12 mL of EtOH is added 4.2 g (25 mmol) of 1-dimethoxyphosphorylpropan-2-one followed by the dropwise addition of 2 g (20 mmol) of tetrahydropyran-4-one. After stirring for 4 h, brine is added and the mixture is extracted three times with MTBE. The combined extracts are washed with brine, dried over $Na_2SO_4$ and concentrated to provide 3.1 g of 1-tetrahydropyran-4-ylidenepropan-2-one (I-AAB; 90%, with 10% EtOH).

To a mixture of 2.1 g (14 mmol) of 90% I-AAB in 16 mL of EtOH is added 2.1 mL (14 mmol) of diethyl malonate, followed by the dropwise addition of 5.1 mL (14 mmol) of 21% NaOEt in EtOH. The mixture is stirred for 2.5 h at room temperature, and heated to reflux for 1 h, cooled to room temperature and concentrated to provide a solid residue that is then stirred with 20 mL of 10 N NaOH for 2 days. The pH is adjusted to between 2 and 3 with concentrated HCl, and the mixture is warmed to 70° C. for 3 h, and then is cooled to room temperature and extracted three times with $CH_2Cl_2$. The combined extracts are washed with brine, dried ($Na_2SO_4$), filtered, and concentrated to provide 1.3 g (6.9 mmol) of I-AAA.

The general method used to prepare I-AAA is also used to prepare the following cylcohexane-1,3-diones:
- I-AAC: 3-Oxaspiro[4.5]decane-7,9-dione is prepared from tetrahydrofuran-3-one.
- I-AAD: Spiro[3.5]nonane-6,8-dione is prepared from cyclobutanone.

5,5-Dimethylcyclohexane-1,3-dione (I-AAI) and cyclohexane-1,3-dione (I-AAJ) are purchased from commercial vendors.

Synthesis of ethyl 3,5-dioxocyclohexanecarboxylate (I-AAE).

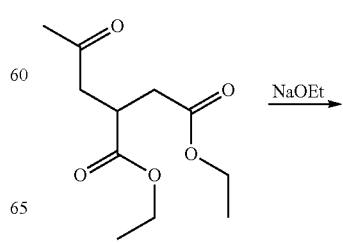

-continued

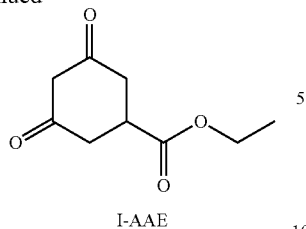

I-AAE

A mixture of 5.4 g (23 mmol) of acetonyl succinic acid diethyl ester, 80 mL of EtOH, and 7.6 g (23 mmol) of 21% NaOEt in EtOH are stirred at 70° C. for 2 hours. The reaction mixture is concentrated to provide 4.3 g (23 mmol) of I-AAE that is used without further manipulation.

Synthesis of spiro[2.5]octane-5,7-dione (I-AAF).

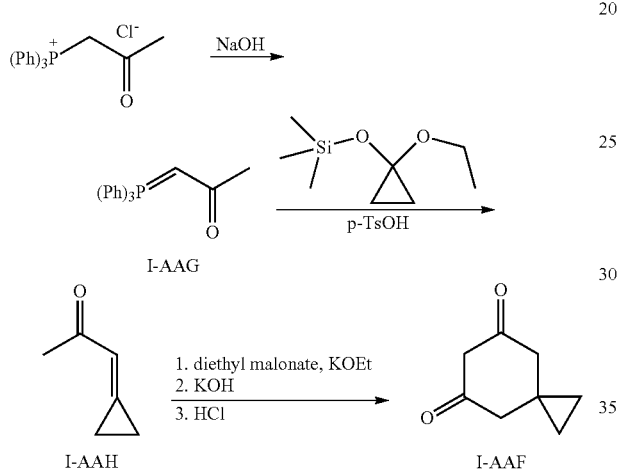

To 50 g (150 mmol) of acetonyl triphenylphosphonium chloride in 2 L of water is added 10% NaOH solution until the pH reaches 8. The mixture is filtered and filter cake is dried to provide 45 g (140 mmol) of 1-(triphenyl-$\lambda^5$-phosphanylidene)propan-2-one (I-AAG).

To a mixture of 8.2 g (47 mmol) of (1-ethoxy-cyclopropoxy)-trimethyl-silane in 22 mL of toluene is added 14 g (44 mmol) of I-AAG and 0.8 g (5 mmol) of p-TsOH. The mixture is heated at 100° C. for 12 h. The mixture is cooled, concentrated, and purified by flash chromatography (0-100% CH$_2$Cl$_2$ in hexanes to provide 2.1 g (22 mmol) of 1-cyclopropylidenepropan-2-one (I-AAH).

The general method used to prepare I-AAA is used to prepare I-AAF from I-AAH.

Synthesis of spiro[5,7-dihydro-3H-benzimidazole-6,4'-tetrahydropyran]-4-one (I-AAM).

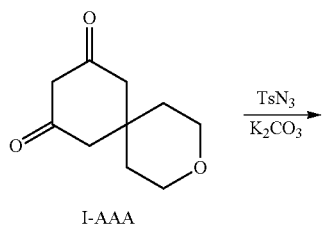

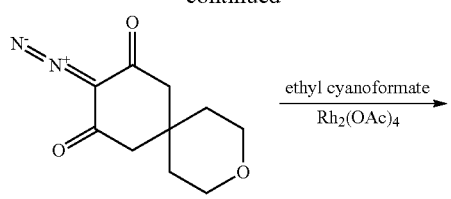

I-AAN

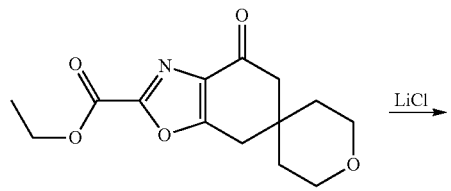

I-AAO

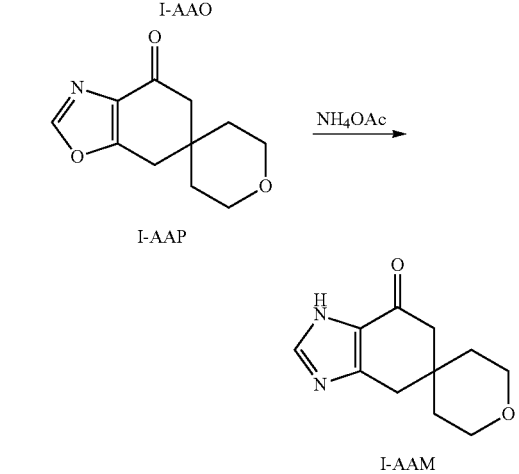

I-AAP

To a mixture of 2.7 g (14 mmol) of tolenesulfonyl azide in 15 mL of MeCN is added 2.5 g (14 mmol) I-AAA and 2.1 g (15 mmol) of K$_2$CO$_3$. The mixture is stirred for 12 h. The mixture is diluted filtered through a short pad of silica gel. The filtrate is concentrated and purified by flash chromatography (0-50% EtOAC in Heptane) to provide 2.4 g (12 mmol) of 9-diazo-3-oxaspiro[5.5]undecane-8,10-dione (I-AAN).

A mixture of 2.2 g (11 mmol) of I-AAN and 0.20 g (0.46 mmol) of Rh$_2$(OAc)$_4$ in 8.5 g of ethyl cyanoformate is heated at 60° C. for 12 h. The mixture is concentrated and purified by flash chromatography (0-60% EtOAc in heptanes) to provide 0.96 g (3.4 mmol) of ethyl 4-oxo-4,5,7,7a-tetrahydro-3aH-spiro[1,3-benzoxazole-6,4'-oxane]-2-carboxylate (I-AAO). This material is stirred in 10 mL of DMF with 0.58 g (14 mol) of LiCl for 12 h at 130° C. Then the mixture is concentrated, diluted with EtOAc, and washed with water, dried over Na$_2$SO$_4$, filtered, concentrated, and purified by flash chromatography (0-5% MeOH in CH$_2$Cl$_2$) to give 0.60 g (2.9 mmol) of 4,5,7,7a-tetrahydro-3aH-spiro[1,3-benzoxazole-6,4'-oxane]-4-one (I-AAP). A mixture of this material and 0.89 g (12 mmol) of ammonium acetate are heated to 140° C. in a microwave reactor for 15 min. Flash chromatography (0-10% MeOH in CH$_2$Cl$_2$) provides 0.23 g (1.1 mmol) of I-AAM.

The general method used to prepare I-AAM is also used to prepare the following 7-oxo-tetrahydrobenzimidazol-4-ones:

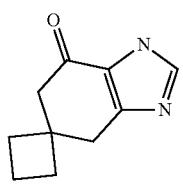 [SMILES: O=C1CC2(CCC2)Cc2nc[nH]c21]

I-AAQ: Spiro[5,7-dihydro-3H-benzimidazole-6,1'-cyclobutane]-4-one is prepared from I-AAD.

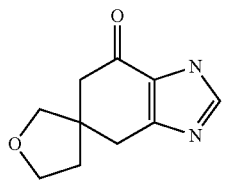 [SMILES: O=C1CC2(CCOC2)Cc2nc[nH]c21]

I-AAR: Spiro[5,7-dihydro-3H-benzimidazole-6,3'-tetrahydrofuran]-4-one is prepared from I-AAC.

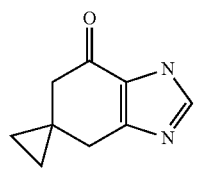 [SMILES: O=C1CC2(CC2)Cc2nc[nH]c21]

I-AAS: Spiro[5,7-dihydro-3H-benzimidazole-6,1'-cyclopropane]-4-one is prepared from I-AAF.

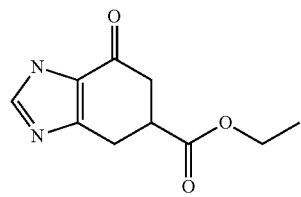

I-AAT: Ethyl 7-oxo-1,4,5,6-tetrahydrobenzimidazole-5-carboxylate is prepared from I-AAE.

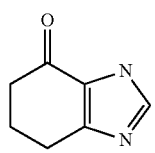

3,5,6,7-Tetrahydrobenzimidazol-4-one (I-AAK) and

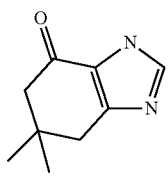

6,6-dimethyl-5,7-dihydro-3H-benzimidazol-4-one (I-AAL) are prepared from I-AAJ and I-AAI respectively via the method described by Krebs and Bondi (Helvetica Chimica Acta, 1979 , 62, 497-506).

Synthesis of (1-acetyl-3,4-dihydro-2H-quinolin-6-yl)boronic acid (N-001)

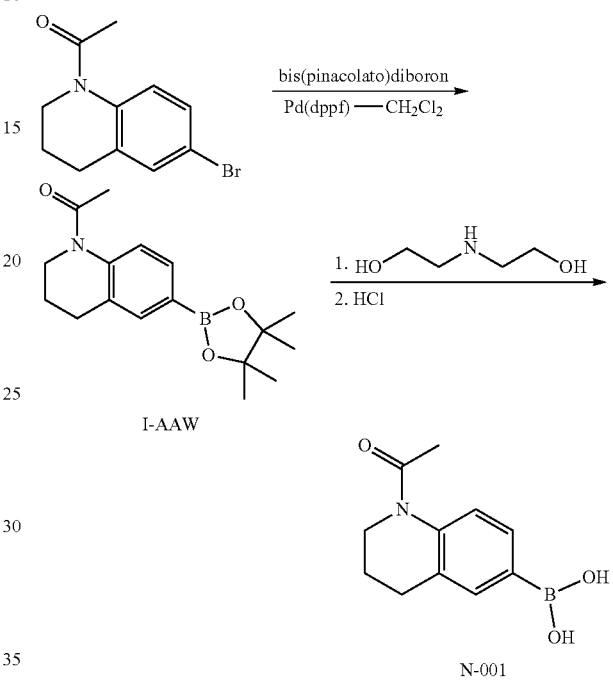

A mixture of 1.5 g (5.9 mmol) of 1-(6-bromo-3,4-dihydro-2H-quinolin-1-yl)ethanone, 2.3 g (8.9 mmol) of bis (pinacolato)diboron, 1.7 g (19 mmol) of KOAc and 0.49 g (0.59 mmol) of Pd(dppf)-$CH_2Cl_2$ in 8 ml of degasses 1,4-dioxane is heated to 110° C. with microwave irradiation for 1 h. The mixture is filtered, concentrated, and purified by flash chromatography (0-7% MeOH in $CH_2Cl_2$) to provide 1.4 g (4.5 mmol) of 1-[6-(4,4,5,5-tetramethyl-1,3,2-dioxaborolan-2-yl)-3,4-dihydro-2H-quinolin-1-yl]ethanone (I-AAW).

A mixture of 1.4 g (4.5 mmol) of I-AAW, 2.4 g (23 mmol) of diethanolamine, and 10 mL of $CH_2Cl_2$ is stirred for 36 h. The mixture is concentrated and purified by flash chromatography (0-10% MeOH in $CH_2Cl_2$) to provide 0.46 g (1.5 mmol) of 1-[6-(1,3,6,2-dioxazaborocan-2-yl)-3,4-dihydro-2H-quinolin-1-yl] ethanone (I-AAX).

I-AAX (0.22 g, 0.75 mmol) is stirred with 1 mL of 1M HCl for 2 h. A solid is generated, that is filtered and dried to provide 0.10 g (0.46 mmol) of N-001.

The general method for the synthesis of N-001 is also used to prepare the following boronic acids.

N-002: (1-methyl-2-oxo-3,4-dihydroquinolin-6-yl)boronic acid is prepared from 6-bromo-1-methyl-3,4-dihydroquinolin-2-one.

N-003: (3-methyl-2-oxo-1,3-benzoxazol-6-yl)boronic acid is prepared from 6-bromo-3-methyl-1,3-benzoxazol-2-one.

N-004: (4-methyl-3-oxo-1,4-benzoxazin-7-yl)boronic acid is prepared from 7-bromo-4-methyl-1,4-benzoxazin-3-one.

Synthesis of Final Compounds

Example 1: Synthesis of 3-(1-acetyl-2,3-dihydro-1H-indol-5-yl)-3,5,6,7-tetrahydro-benzoimidazol-4-one (C-AAA)

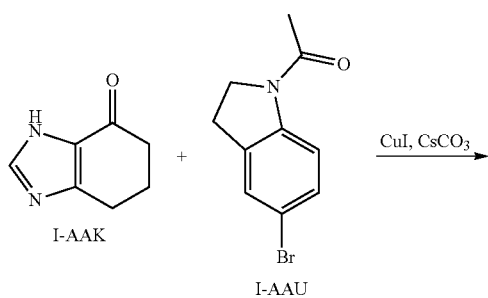

Example 2: Synthesis of 1-methyl-6-(7-oxo-4,5,6,7-tetrahydro-benzoimidazol-1-yl)-3,4-dihydro-1H-[1,8]naphthyridin-2-one (C-AAD)

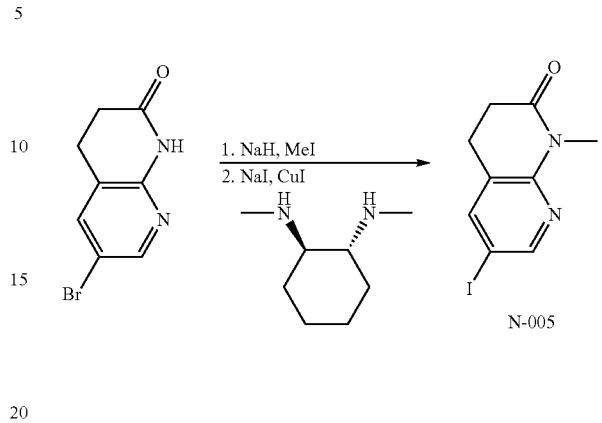

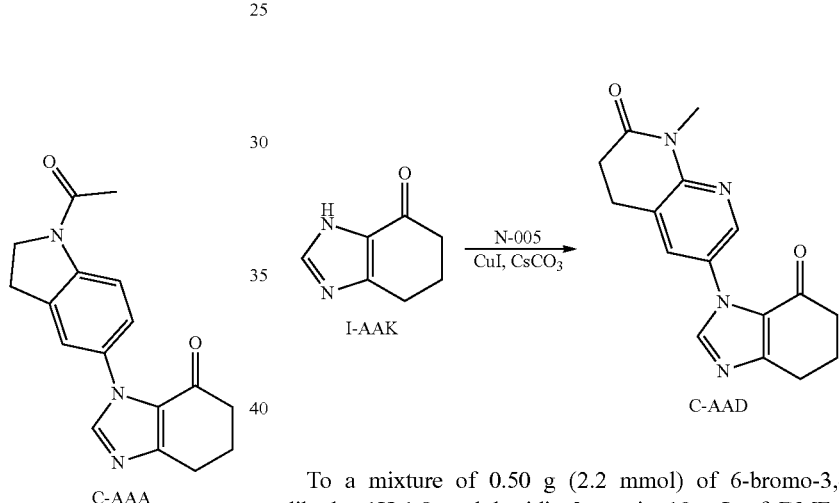

A mixture of 0.10 g (0.75 mmol) of I-AAK, 0.15 g (0.63 mmol) of 1-(5-bromo-2,3-dihydro-1H-indol-1-yl)ethan-1-one (I-AAU), 0.41 g (1.3 mmol) of $CsCO_3$ and 24 mg (0.13 mmol) of CuI in 6 mL of DMSO is heated to 120° C. for 4 days. The reaction mixture is concentrated, dissolved in EtOAc, washed with water and brine, dried with $Na_2SO_4$, filtered, concentrated, and purified by flash chromatography (0-5% MeOH in $CH_2Cl_2$). Two isomeric products are isolated, with the less polar isomer being C-AAA (7 mg, 0.02 mmol).

The general method used to prepare C-AAA is also used to prepare the following compounds with the appropriate aryl halide.

Compound C-AAB: 3-(1,3-dihydro-isobenzofuran-5-yl)-3,5,6,7-tetrahydro-benzoimidazol-4-one is prepared from I-AAK and 5-bromo-1,3-dihydroisobenzofuran.

Compound C-AAC: 2-methyl-7-(7-oxo-4,5,6,7-tetrahydro-benzoimidazol-1-yl)-1,4-dihydro-2H-isoquinolin-3-one is prepared from I-AAK and 7-bromo-2-methyl-1,4-dihydroisoquinolin-3-one.

To a mixture of 0.50 g (2.2 mmol) of 6-bromo-3,4-dihydro-1H-1,8-naphthyridin-2-one in 10 mL of DMF is added 0.13 g (3.3 mmol) of 60% NaH in mineral oil. After stirring for 30 min, 0.62 g (4.4 mmol) of MeI is added and the mixture is stirred for 18 h, concentrated, dissolved in EtOAc, washed with water and brine, dried with $Na_2SO_4$, filtered and concentrated. The residue is purified by flash chromatography (0-50% EtOAc in heptane) to provide 0.50 g (2.1 mmol) of 6-bromo-1-methyl-3,4-dihydro-1,8-naphthyridin-2-one. This material combined with 0.62 g (4.1 mmol) of NaI, 40 mg (0.21 mmol) of CuI, 5 mL of 1,4-dioxane, and 30 mg (0.21 mmol) of trans-N,N'-dimethylcyclohexane-1,2-diamine, and then stirred at 110° C. for 18 hours. The reaction mixture is concentrated, dissolved in EtOAc, washed with water, brine, dried with $Na_2SO_4$, filtered and concentrated. The residue is purified by flash chromatography (0-50% EtOAc in heptane) to provide 0.57 g (2.0 mmol) of N-005.

Compound C-AAD is then prepared from N-005 and I-AAK using the general method described for the synthesis of I-AAA.

Example 3: Synthesis of 3-(2,3-dihydro-benzofuran-5-yl)-3,5,6,7-tetrahydro-benzoimidazol-4-one (C-AAE)

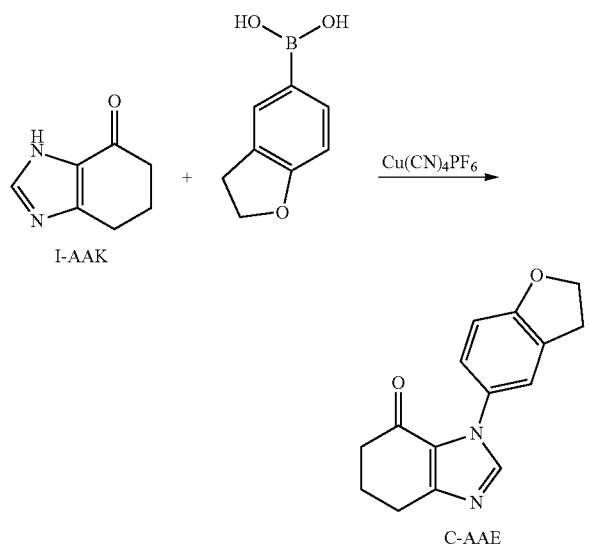

A mixture of 0.10 g (0.73 mmol) of C-AAK, 0.13 g (0.81 mmol) of 2,3-dihydro-1-benzofuran-5-ylboronic acid and the 82 mg (0.22 mmol) of Cu(CN)$_4$PF$_6$, 4 mL of MeOH is stirred for 2 days. The mixture is filtered through diatomaceous earth and the filtrate is concentrated and purified by flash chromatography first on silica (0-10% MeOH in CH$_2$Cl$_2$), then on a KPNH-silica column (0-100% EtOAc/heptane) to provide 45 mg (0.18 mmol) of C-AAE.

The general method used to prepare C-AAE is also used to prepare the following compounds with the appropriate tetrahydrobenzimidazol-4-one and aryl boronic acid.

Compound C-AAF: 3-(1-Acetyl-1,2,3,4-tetrahydro-quinolin-6-yl)-3,5,6,7-tetrahydro-benzoimidazol-4-one is prepared from I-AAK and 3,5,6,7-tetrahydro-benzoimidazol-4-one.

Compound C-AAG: 3-(1-Methyl-1H-indazol-5-yl)-3,5,6,7-tetrahydro-benzoimidazol-4-one is prepared from I-AAK and 1-methylindazole-5-boronic acid.

Compound C-AAH: 3-(1-Methyl-1H-indazol-6-yl)-3,5,6,7-tetrahydro-benzoimidazol-4-one is prepared from I-AAK and 1-methylindazole-6-boronic acid.

Compound C-AAI: 3-(2,3-Dihydro-benzo[1,4]dioxin-6-yl)-3,5,6,7-tetrahydro-benzoimidazol-4-one is prepared from I-AAK and 1,4-benzodioxane-6-boronic acid.

Compound C-AAJ: 3-(3,4-Dihydro-2H-benzo[b][1,4]dioxepin-7-yl)-3,5,6,7-tetrahydro-benzoimidazol-4-one is prepared from I-AAK and 3,4-dihydro-2H-1,5-benzodioxepin-7-boronic acid.

Compound C-AAK: 3-Cyclopropyl-4-(7-oxo-4,5,6,7-tetrahydro-benzoimidazol-1-yl)-benzonitrile is prepared from I-AAK and 2-cyclopropyl-4-cyanophenyl boronic acid.

Compound C-AAL: 4-(7-Oxo-4,5,6,7-tetrahydro-benzoimidazol-1-yl)-benzonitrile is prepared from I-AAK and 4-cyanophenyl boronic acid.

Compound C-AAM: 3-Methyl-6-(7-oxo-4,5,6,7-tetrahydro-benzoimidazol-1-yl)-3H-benzooxazol-2-one is prepared from I-AAK and (3-methyl-2-oxo-1,3-benzoxazol-6-yl)boronic acid.

Compound C-AAN: 4-Methyl-7-(7-oxo-4,5,6,7-tetrahydro-benzoimidazol-1-yl)-4H-benzo[1,4]oxazin-3-one is prepared from I-AAK and (4-methyl-3-oxo-1,4-benzoxazin-7-yl)boronic acid.

Compound C-AAO: 2-Methyl-4-(7-oxospiro[4,6-dihydrobenzimidazole-5,4'-tetrahydropyran]-1-yl)benzonitrile is prepared from I-AAM and 3-methyl-4-cyanophenyl boronic acid.

Compound C-AAP: 3-(1-Methyl-2-oxo-3,4-dihydroquinolin-6-yl)spiro[5,7-dihydrobenzimidazole-6,4'-tetrahydropyran]-4-one is prepared from I-AAM and (1-methyl-2-oxo-3,4-dihydroquinolin-6-yl)boronic acid.

Compound C-AAQ: 3-(3-Chloro-4-cyano-phenyl)-6,6-3-o-tetrahydropyran-3,5,6,7-tetrahydro-benzoimidazol-4-one is prepared from I-AAM and 3-chloro-4-cyanophenylboronic acid.

Compound C-AAR: 3-(4-Chloro-phenyl)-6,6-3-o-tetrahydropyran-3,5,6,7-tetrahydro-benzoimidazol-4-one is prepared from I-AAM and 4-chlorophenyl boronic acid.

Compound C-AAS: 4-(7-Oxospiro[4,6-dihydrobenzimidazole-5,4'-tetrahydropyran]-1-yl)benzonitrile is prepared from I-AAM and 4-cyanophenyl boronic acid.

Compound C-AAT: 1N-4-cyanophenyl-5-spirocycbutyl-tetrahydrobenimidazo-7-one is prepared from I-AAQ and 4-cyanophenyl boronic acid.

Compound C-AAU: 2-Methyl-4-(7-oxospiro[4,6-dihydrobenzimidazole-5,1'-cyclobutane]-1-yl)benzonitrile is prepared from I-AAQ and 4-cyano-3-methylphenyl boronic acid.

Compound C-AAV: 3-(1-Methyl-2-oxo-3,4-dihydroquinolin-6-yl)spiro[5,7-dihydrobenzimidazole-6,1'-cyclobutane]-4-one is prepared from I-AAQ and and (1-methyl-2-oxo-3,4-dihydroquinolin-6-yl)boronic acid.

Compound C-AAW: 3-(3-Chloro-4-cyano)-6,6-spirocyclopropyl-3,5,6.7-tetrahydrobenzimidazol-4-one is prepared from I-AAS and 4-cyano-3-methylphenyl boronic acid.

Compound C-AAX: 3-(4-Cyanophenyl)-6,6-spirocyclpropyl-3,5,6,7-tetrahydro-benzimidiazol-4-one is prepared from I-AAS and 4-cyanophenyl boronic acid.

Compound C-AAY: 1-(3-Chloro-4-cyano-phenyl)-7-oxo-4,5,6,7-tetrahydro-1H-benzoimidazole-5-carboxylic acid ethyl ester is prepared from I-AAT and 4-cyano-3-chlorophenyl boronic acid.

Compound C-AAZ: Racemic 3-(2-methyl-2,3-dihydrobenzofuran-5-yl)-3,5,6,7-tetrahydro-benzoimidazol-4-one is prepared from I-AAK and (2-methyl-2,3-dihydrobenzofuran-6-yl)boronic acid. Chiral resolution (LUX 5 u Cellulose 3 Analytical 15%(1:1:1MeOH:EtOH:iPA):CO2, 40 C, 200 bar) delivers C-AAZ-A enantiomer A and C-AAZ-B enantiomer B.

Compound C-ABA: Racemic 3-(4-cyanophenyl)-6,6-(3-tetrahydrofuran)-3,5,6,7-benzimidiazolo-4-one is prepared from I-AAR and 4-cyano-3-chlorophenyl boronic acid. Chiral resolution (AD-RH 5 um 21×250 mm 35%(1:1:1MeOH:EtOH:iPA):CO2 (no base), 125gr/min, 35 C, 120 bar) delivers C-ABA-A enantiomer A and C-ABA-B enantiomer B.

Compound C-ABB: tert-Butyl 6-(7-oxo-5,6-dihydro-4H-benzimidazol-1-yl)-3,4-dihydro-2H-quinoline-1-carboxylate (I-AAV) is prepared from I-AAK and (1-tert-butoxycarbonyl-3,4-dihydro-2H-quinolin-6-yl)boronic acid. A mixture of I-AAV (62 mg, 0.17 mmol), 2 mL Example 4: Synthesis of 3-(3,4-difluoro-phenyl)-6,6-dimethyl-3,5,6,7-tetrahydro-benzoimidazol-4-one (C-ABC)

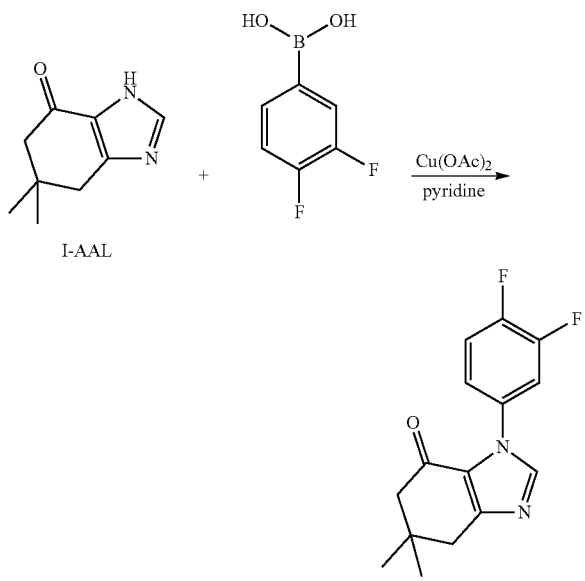

A mixture of 0.10 g (0.61 mmol) of I-AAL, 96 mg (0.61 mmol) of 3,4-diflurophenylboronic acid, 0.22 g (1.2 mmol) of Cu(OAc)$_2$, and 0.10 mL (1.2 mmol) of pyridine are stirred at 40° C. for 12 h. The mixture is filtered through a pad of diatomaceous earth and the filtrate is concentrated and purified on a Biotage KP-NH amine-functionalized silica column eluted with 5-50% EtOAc in heptane to provide 15 mg (0.05 mmol) of C-ABC.

The general method used to prepare C-ABC is also used to prepare the following compounds with the appropriate tetrahydrobenzimidazol-4-one and aryl boronic acid.

Compound C-ABD: 3-(3,4-Dichloro-phenyl)-6,6-dimethyl-3,5,6,7-tetrahydro-benzoimidazol-4-one is prepared from I-AAL and 3,4-dichlorophenylboronic acid.

Compound C-ABE: 2-Chloro-4-(5,5-dimethyl-7-oxo-4,5,6,7-tetrahydro-benzoimidazol-1-yl)-benzonitrile is prepared from I-AAL and 3-chloro-4-cyanophenylboronic acid.

Compound C-ABF: 3-(2,3-Dichloro-phenyl)-6,6-dimethyl-3,5,6,7-tetrahydro-benzoimidazol-4-one is prepared from I-AAL and 2,3-dichlorophenylboronic acid.

Compound C-ABG: 3-(2,4-Dichloro-phenyl)-6,6-dimethyl-3,5,6,7-tetrahydro-benzoimidazol-4-one is prepared from I-AAL and 2,4-dichlorophenylboronic acid.

Compound C-ABH: 3-(3,5-Dichloro-phenyl)-6,6-dimethyl-3,5,6,7-tetrahydro-benzoimidazol-4-one is prepared from I-AAL and 3,5-dichlorophenylboronic acid.

Compound C-ABI: 3-(3-Chloro-4-fluoro-phenyl)-6,6-dimethyl-3,5,6,7-tetrahydro-benzoimidazol-4-one is prepared from I-AAL and 3-chloro-4-fluorophenylboronic acid.

Compound C-ABJ: 3-(3-Chloro-4-isopropoxy-phenyl)-6,6-dimethyl-3,5,6,7-tetrahydro-benzoimidazol-4-one is prepared from I-AAL and 3-chloro-4-isopropoxyphenyl boronic acid.

Compound C-ABK: 3-(3-Chloro-phenyl)-6,6-dimethyl-3,5,6,7-tetrahydro-benzoimidazol-4-one is prepared from I-AAL and 3-chlorophenylboronic acid.

Compound C-ABL: 3-(4-Acetyl-phenyl)-6,6-dimethyl-3,5,6,7-tetrahydro-benzoimidazol-4-one is prepared from I-AAL and 4-acetylphenylboronic acid.

Compound C-ABM: 3-(4-Chloro-3-fluoro-phenyl)-6,6-dimethyl-3,5,6,7-tetrahydro-benzoimidazol-4-one is prepared from I-AAL and 4-chloro-3-fluorophenylboronic acid.

Compound C-ABN: 3-(4-Chloro-phenyl)-6,6-dimethyl-3,5,6,7-tetrahydro-benzoimidazol-4-one is prepared from I-AAL and 4-chlorophenylboronic acid.

Compound C-ABO: 3-(4-Dimethylamino-phenyl)-6,6-dimethyl-3,5,6,7-tetrahydro-benzoimidazol-4-one is prepared from I-AAL and 4-dimethylphenylboronic acid.

Compound C-ABP: 3-(4-Fluoro-phenyl)-6,6-dimethyl-3,5,6,7-tetrahydro-benzoimidazol-4-one is prepared from I-AAL and 4-fluorophenylboronic acid.

Compound C-ABQ: 3-(4-Isopropoxy-phenyl)-6,6-dimethyl-3,5,6,7-tetrahydro-benzoimidazol-4-one is prepared from I-AAL and 4-isopropoxyphenylboronic acid.

Compound C-ABR: 3-(4-Methoxy-phenyl)-6,6-dimethyl-3,5,6,7-tetrahydro-benzoimidazol-4-one is prepared from I-AAL and 4-methoxyphenylboronic acid.

Compound C-ABS: 3-(5,5-Dimethyl-7-oxo-4,5,6,7-tetrahydro-benzoimidazol-1-yl)-benzonitrile is prepared from I-AAL and 4-cyanophenylboronic acid.

Compound C-ABT: 3-(6-Chloro-pyridin-3-yl)-6,6-dimethyl-3,5,6,7-tetrahydro-benzoimidazol-4-one is prepared from I-AAL and 4-chloro-pyridin-3-yl boronic acid.

Compound C-ABU: 3-Benzo[1,3]dioxol-5-yl-6,6-dimethyl-3,5,6,7-tetrahydro-benzoimidazol-4-one is prepared from I-AAL and 1,3-benzodioxol-5-ylboronic acid.

Compound C-ABV: 4-(5,5-Dimethyl-7-oxo-4,5,6,7-tetrahydro-benzoimidazol-1-yl)-2-methyl-benzonitrile is prepared from I-AAL and 4-cyano-3-methylphenylboronic acid.

Compound C-ABW: 4-(5,5-Dimethyl-7-oxo-4,5,6,7-tetrahydro-benzoimidazol-1-yl)-benzoic acid methyl ester is prepared from I-AAL and (4-methoxycarbonyl-phenyl)boronic acid.

Compound C-ABX: 4-(5,5-Dimethyl-7-oxo-4,5,6,7-tetrahydro-benzoimidazol-1-yl)-benzonitrile is prepared from I-AAL and 4-cyanophenyl boronic acid.

Compound C-ABY: 5-(5,5-Dimethyl-7-oxo-4,5,6,7-tetrahydro-benzoimidazol-1-yl)-2-methyl-benzonitrile is prepared from I-AAL and 3-cyano-4-methylphenyl boronic acid.

Compound C-ABZ: 6,6-Dimethyl-3-(3-trifluoromethyl-phenyl)-3,5,6,7-tetrahydro-benzoimidazol-4-one is prepared from I-AAL and 3-trifluoromethylphenyl boronic acid.

Compound C-ACA: 6,6-Dimethyl-3-phenyl-3,5,6,7-tetrahydro-benzoimidazol-4-one is prepared from I-AAL and phenylboronic acid.

Compound C-ACB: 6,6-Dimethyl-3-p-tolyl-3,5,6,7-tetrahydro-benzoimidazol-4-one is prepared from I-AAL and 4-methylphenylboronic acid.

Compound C-ACC: 3-(3,4-Dichloro-phenyl)-3,5,6,7-tetrahydro-benzoimidazol-4-one is prepared from I-AAK and 3,4-dichlorophenylboronic acid.

Compound C-ACD: 1-Methyl-6-(7-oxo-4,5,6,7-tetrahydro-benzoimidazol-1-yl)-3,4-dihydro-1H-quinolin- 2-one is prepared from I-AAK and (1-methyl-2-oxo-3,4-dihydroquinolin-6-yl)boronic acid (N-002).

Compound C-ACE: 3-(3,4-difluoro-phenyl)-6,6-spirocyclopropyl-3,5,6,7-tetrahydro-benzimidiazolo-4-one is prepared from I-AAQ and 3,4-difluorophenylboronic acid.

Compound C-ACF: 3-(4-chloroophenyl)-6,6-spirocyclopropyl-3,5,6,7-tetrahydro-benzimidiazolo-4-one is prepared from I-AAQ and 4-chlorophenylboronic acid.

Compound C-ACG: 3-(4-cyano, 3-chlorophenyl)-6,6-spirocyclobutyl-3,5,6,7-benzimidiazolo-4-one is prepared from I-AAQ and 3-chloro-4-cyanophenylboronic acid.

Compound C-ACH: 3-(1-methyl-2-oxo-3,4-dihydroquinolin-6-yl)spiro[5,7-dihydrobenzimidazole-6,1'-cyclopropane]-4-one is prepared from I-AAS and (1-methyl-2-oxo-3,4-dihydroquinolin-6-yl)boronic acid (N-002).

Compound C-ACI: 6,6-Dimethyl-3-(4-trifluoromethylphenyl)-3,5,6,7-tetrahydro-benzoimidazol-4-one is prepared from I-AAL and 4-trifluoromethylphenyl boronic acid.

Example 5: Synthesis of trans-4-(7-oxo-5,6-dihydro-4H-benzimidazol-1-yl)cyclohexanecarbonitrile (C-ACJ)

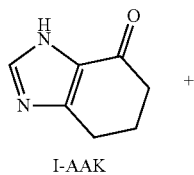

I-AAK

+

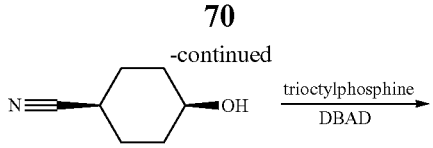

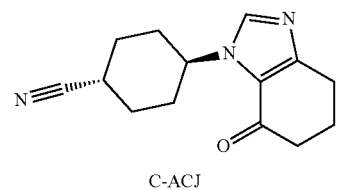

C-ACJ

To a mixture of 0.27 g (2.0 mmol) of I-AAK, 0.69 g (3.0 mmol) of di-tert-butylazodicarboxylate (DBAD) and 0.35 g (2.8 mmol) of cis-4-cyanocyclohexanol in 5 mL of THF is added 1.5 mL (3.0 mmol) of 90% trioctylphosphine. The mixture is stirred for 72 h, concentrated, and purified first by flash chromatography (0-100% EtOAc in heptanes then 0-10% MeOH in $CH_2Cl_2$) then by preparative TLC (100% EtOAc) and again with preparative TLC (2.5% MeOH in $CH_2Cl_2$) to give 0.11 g (0.44 mmol) of C-ACJ.

Compounds below are prepared using the general method described for the synthesis of C-ACJ using the indicated imidazole, diazodicarboxylate reagent, alcohol, and phosphine.

| Compound | Imidazole | Diazodicarboxylate | Alcohol | phosphine |
|---|---|---|---|---|
| C-ACK | I-AAL | Piperidinediazodicarboxylate | cyclohexanol | trioctylphosphine |
| C-ACL | I-AAL | DBAD | (1R,2R,4S)-norbornan-2-ol | trioctylphosphine |
| C-ACM | I-AAL | DBAD | 6-bromotetralin-2-ol | trioctylphosphine |
| C-CAN | I-AAL | DBAD | 6-methoxytetralin-2-ol | trioctylphosphine |
| C-ACO | I-AAL | DBAD | Decalin-2-ol | trioctylphosphine |
| C-ACP | I-AAL | DBAD | cyclohexylmethanol | trioctylphosphine |
| C-ACQ | I-AAL | DBAD | Indan-1-ol | trioctylphosphine |
| C-ACR | I-AAL | DBAD | (5S)-5-hydroxy-1-methyl-piperidin-2-one | trioctylphosphine |
| C-ACS | I-AAL | DBAD | Tetralin-1ol | trioctylphosphine |
| C-ACT | I-AAL | DBAD | 6-oxaspiro[3.3]heptan-2-ol | trioctylphosphine |
| C-ACU | I-AAL | DBAD | 3-phenylcyclobutanol | trioctylphosphine |
| C-ACV | I-AAL | DBAD | 5,6,7,8-tetrahydroquinazolin-6-ol | trioctylphosphine |
| C-ACW | I-AAL | DBAD | 6,7,8,9-tetrahydro-5H-benzo[7]annulen-5-ol | trioctylphosphine |
| C-ACX | I-AAL | DBAD | tetrahydrofuran-3-ylmethanol | trioctylphosphine |
| C-ACY | I-AAL | DBAD | 5-hydroxymethyl-1H-indazole | $P(Ph)_3$ |
| C-ACZ | I-AAL | DBAD | methyl 4-(hydroxymethyl)benzoate | $P(Ph)_3$ |
| C-ADA | I-AAL | DBAD | Cyclopropylmethanol | $P(Ph)_3$ |
| C-ADB | I-AAL | DBAD | [4-(1,2,4-triazol-1-yl)phenyl]methanol | $P(Ph)_3$ |
| C-ADC | I-AAL | DBAD | (4-methylthiadiazol-5-yl)methanol | $P(Ph)_3$ |
| C-ADD | I-AAL | DBAD | (4-methyl-2,3-dihydropyrido[3,2-b][1,4]oxazin-7-yl)methanol | $P(Ph)_3$ |

| Compound | Imidazole | Diazodi-carboxylate | Alcohol | phosphine |
|---|---|---|---|---|
| C-ADE | I-AAL | DBAD | N-[4-(hydroxy-methyl)phenyl]acetamide | P(Ph)$_3$ |
| C-ADF | I-AAL | Dibenzyl diazodi-carboxylate | Chroman-2-ol | P(Ph)$_3$ |
| C-ADG | I-AAL | Dibenzyl diazodi-carboxylate | Indan-2-ol | P(Ph)$_3$ |
| C-ADH | I-AAL | Dibenzyl diazodi-carboxylate | Tetralin-2-ol | P(Ph)$_3$ |
| C-ADI | I-AAL | Dibenzyl diazodi-carboxylate | tetrahydropyran-4-ylmethanol | P(Ph)$_3$ |
| C-ADJ | I-AAM | Dibenzyl diazodi-carboxylate | Tetralin-2-ol | P(Ph)$_3$ |
| C-ADK | I-AAM | Dibenzyl diazodi-carboxylate | Indan-2-ol | P(Ph)$_3$ |

Compound C-ADL: A cis/trans mixture of 4-(5,5-dimethyl-7-oxo-4,5,6,7-tetrahydro-benzoimidazol-1-yl)-cyclohexanecarbonitrile is prepared from I-AAL, DBAD, cis/trans-hydroxycyclohexanecarbonitrile, and trioctylphosphine using the general procedure described for the synthesis of compound C-ACJ. The trans-isomer (C-ADL) was then isolated after chromatography (5% to 10% iPrOH (10 mM NH$_3$) in supercritical CO$_2$ for 7 min plus 3 min wash at 90g/min. Column at 40° C., ABPR at 120 bar, MBPR at 40 psi, and collection using a mass spectrum detector to detect molecular weight.

Compound C-ADM: A cis/trans mixture of 3-(3-Ethoxy-spiro[3.3]hept-1-yl)-6,6-dimethyl-3,5,6,7-tetrahydro-benzoimidazol-4-one is prepared from I-AAL, DBAD, cis/trans-7-ethoxyspiro[3.3]heptan-5-ol, and trioctylphosphine using the general procedure described for the synthesis of compound C-ACJ. The trans-isomer (C-ADM) is then isolated after chromatography (LUX 5u Cellulose 2 Prep:9% MeOH in supercritical CO2 for 13 min at 15g/min. Column at 40C, ABPR at 120 and collection on DAD).

Example 6: Synthesis of 6-(5,5-dimethyl-7-oxo-4,5,6,7-tetrahydro-benzoimidazol-1-yl)-5,6,7,8-tetrahydro-naphthalene-2-carbonitrile (C-ADN)

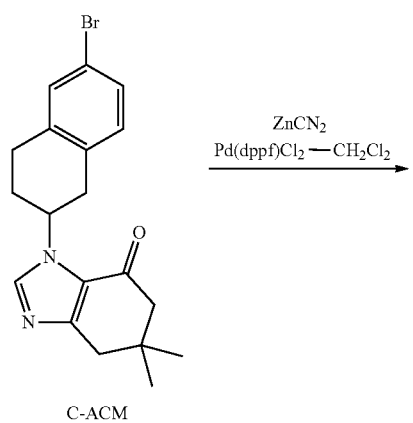

C-ACM

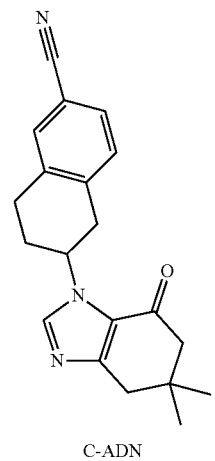

C-ADN

To a mixture of C-ACM (0.23 g; 0.62 mmol) and ZnCN$_2$ (72 mg; 0.62 mmol) in degassed DMF (5 mL) is added Pd(dppf)Cl$_2$·CH$_2$Cl$_2$ (50 mg; 0.062 mmol). The reaction mixture is heated to 160° C. for 30 min in a microwave reactor, and then is purified by preparative HPLC (10-80% MeCN in water) to provide 50 mg (0.16 mmol) of C-ADN.

Example 7: Synthesis of 3-(4-fluoro-benzyl)-6,6-dimethyl-3,5,6,7-tetrahydro-benzoimidazol-4-one (C-ADO)

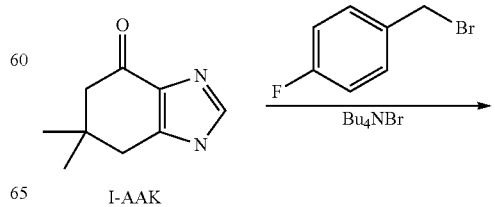

I-AAK

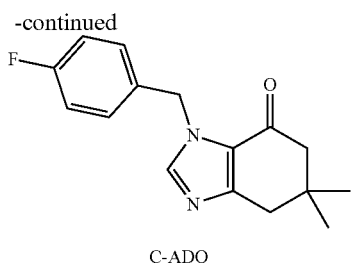

C-ADO

A mixture of 0.10 g (0.61 mmol) of I-AAK, 80 μL (0.67 mmol) of 1-(bromomethyl)-4-fluoro-benzene, 0.16 g (4.0 mmol) of NaOH, 79 mg (0.24 mmol) of Bu₄NBr, 1.2 mL of water and 2 mL of toluene is stirred for 2 h. Saturated NH₄Cl solution is added and the mixture is extracted twice with toluene. The combined extracts are concentrated and purified via preparative HPLC (5%-80% MeCN in water) to provide 0.13 g (0.46 mmol) of C-ADO.

The following compounds are prepared using the general method described for the synthesis of Compound C-ADO.

Compound C-ADP: 3-(4-Methanesulfonyl-benzyl)-6,6-dimethyl-3,5,6,7-tetrahydro-benzoimidazol-4-one is prepared from I-AAK and 1-(bromomethyl)-4-methylsulfonyl-benzene.

Compound C-ADQ: 3-(4-Methoxy-benzyl)-6,6-dimethyl-3,5,6,7-tetrahydro-benzoimidazol-4-one is prepared from I-AAK and 1-(bromomethyl)-4-methoxy-benzene.

Compound C-ADR: 3-Benzyl-6,6-dimethyl-3,5,6,7-tetrahydro-benzoimidazol-4-one is prepared from I-AAK and benzyl bromide.

Example 8: Synhthesis of 4-(5,5-dimethyl-7-oxo-4,5,6,7-tetrahydro-benzoimidazol-1-ylmethyl)-N-(2-hydroxy-ethyl)-N-methyl-benzamide (C-ADS)

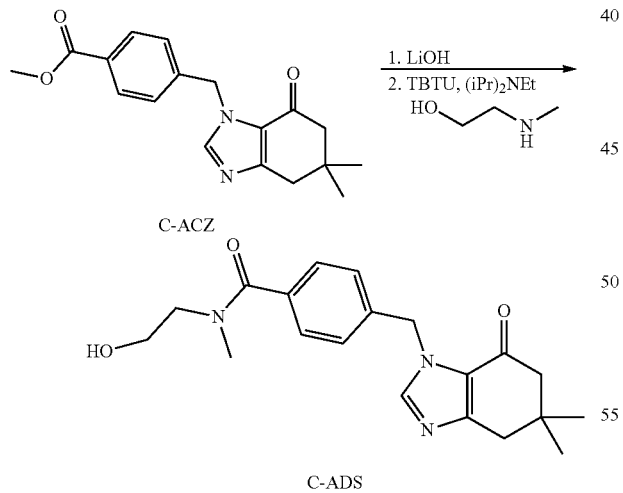

A mixture of C-ACZ (0.46 g, 1.5 mmol) 15 mL of THF, 5 mL of MeOH and 4.4 mL of 1N LiOH is stirred for 1 h, and then 5.5 mL of 1N HCl is added. The mixture is partially concentrated and extracted three times with 25 mL of EtOAc. The combined extracts are dried over Na₂SO₄, filtered and concentrated to provide 0.39 g (1.3 mmol) of 4-[(5,5-dimethyl-7-oxo-4,6-dihydrobenzimidazol-1-yl) methyl]benzoic acid (I-AAY).

A mixture of 0.20 mL (1.2 mmol) of (iPr)₂NEt, 0.12 g (0.39 mmol) of I-AAY, 35 mg (0.46 mmol) of 2-(methylamino)ethanol, and 2 mL of DMF is treated with 0.15 g (0.46 mmol) of TBTU. After stirring overnight, the reaction is purified by preparative HPLC (5%-80% MeCN in water) to provide 64 mg (0.18 mmol) of C-ADS.

The following compounds are prepared using the general method described for the synthesis of Compound C-ADS.

Compound C-ADT: 3-[4-((R)-3-Hydroxy-pyrrolidine-1-carbonyl)-benzyl]-6,6-dimethyl-3,5,6,7-tetrahydro-benzoimidazol-4-one is prepared from I-AAY and (R)-3-hydroxypyrrolidine.

Compound C-ADU: 4-(5,5-Dimethyl-7-oxo-4,5,6,7-tetrahydro-benzoimidazol-1-ylmethyl)-N-(2-methanesulfonyl-ethyl)-benzamide is prepared from I-AAY and 2-methylsulfonylethanamine hydrochloride.

Example 9: Synthesis of 3-[4-(1-hydroxy-1-methyl-ethyl)-benzyl]-6,6-dimethyl-3,5,6,7-tetrahydro-benzoimidazol-4-one (C-ADV)

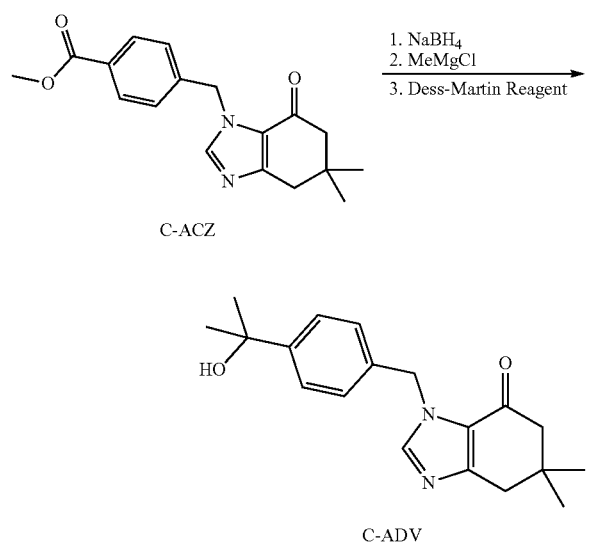

A mixture of 0.17 g (0.55 mmol) of C-ACZ, 3 mL of THF and 3 mL of MeOH is treated with 63 mg (1.8 mmol) of NaBH₄. The mixture is stirred for 12 h, and then 63 mg (1.8 mmol) of NaBH₄ is added. The mixture is stirred for 2 h, concentrated, mixed with 25 mL of acetone and concentrated again. The resulting residue is combined with 1 mL of THF and cooled to 0° C. A 3 M solution of MeMgCl is added slowly (0.6 mL; 1.8 mmol). After 30 min, saturated Na₂CO₃ and saturated NH₄Cl (5 mL each) are added, followed by 5 mL of EtOAc. The organic layer is washed with sat NH₄Cl (5 mL) and water (5 mL), dried over Na₂SO₄, concentrated, and purified by preparative HPLC (5%-80% MeCN in water) to provide 32 mg (mmol) of 3-[[4-(1-hydroxy-1-methyl-ethyl)phenyl]methyl]-6,6-dimethyl-5,7-dihydro-4H-benzimidazol-4-ol. This material is combined with 5 mL of CH₂Cl₂ and 65 mg (0.15 mmol) of Dess-Martin periodinane. After 1 h, the mixture is filtered, concentrated, and purified by preparative HPLC (5%-80% MeCN in water) to provide 4 mg (0.01 mmol) of C-ADV.

Example 10: Synthesis of 6-(7-oxo-4,5,6,7-tetra-hydro-benzoimidazol-1-yl)-nicotinonitrile (C-ADW)

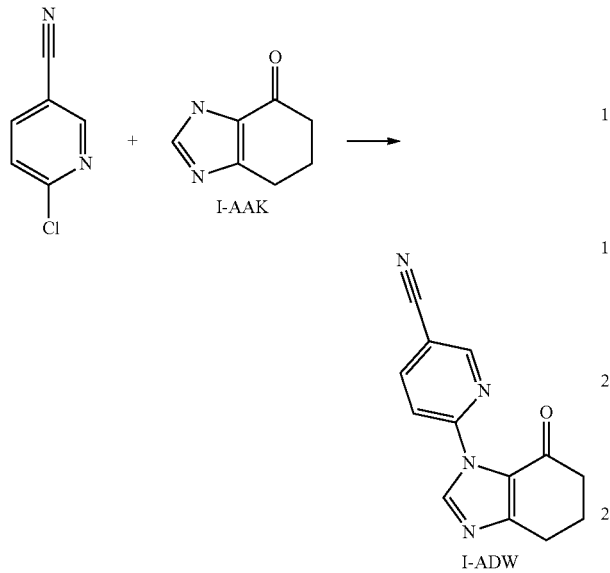

A mixture of 0.10 g (0.72 mmol) 6-chloro-3-pyridine-carbonitrile, 0.15 g (1.0 mmol) of I-AAK, 0.47 g (1.4 mmol) of CsCO$_3$, and 4 mL of DMF is stirred at 100° C. for 18 h. The mixture is concentrated, dissolved in EtOAc, washed with water and brine, dried with Na$_2$SO$_4$, filtered, concentrated, and purified first by flash chromatography (0-5% MeOH/CH$_2$Cl$_2$), and then by preparative TLC (5% MeOH in CH$_2$Cl$_2$) to afford 14 mg (0.06 mmol) of C-ADW.

Example 11: Synthesis of 3-(1-Methyl-4,5,6,7-tetra-hydro-1H-indazol-6-yl)-3,5,6,7-tetrahydro-benzo-imidazol-4-one (C-AEF)

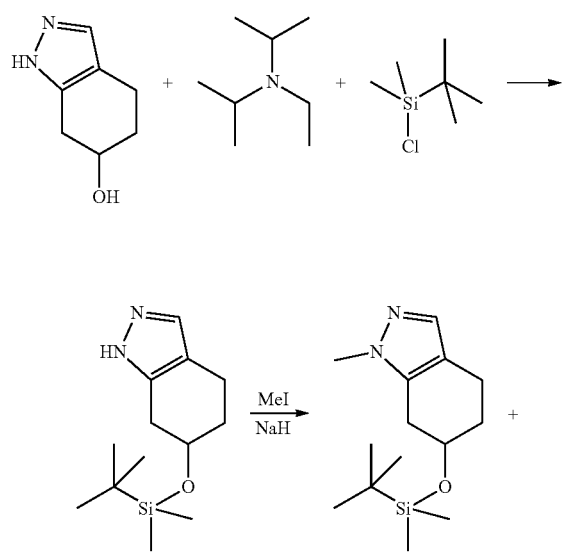

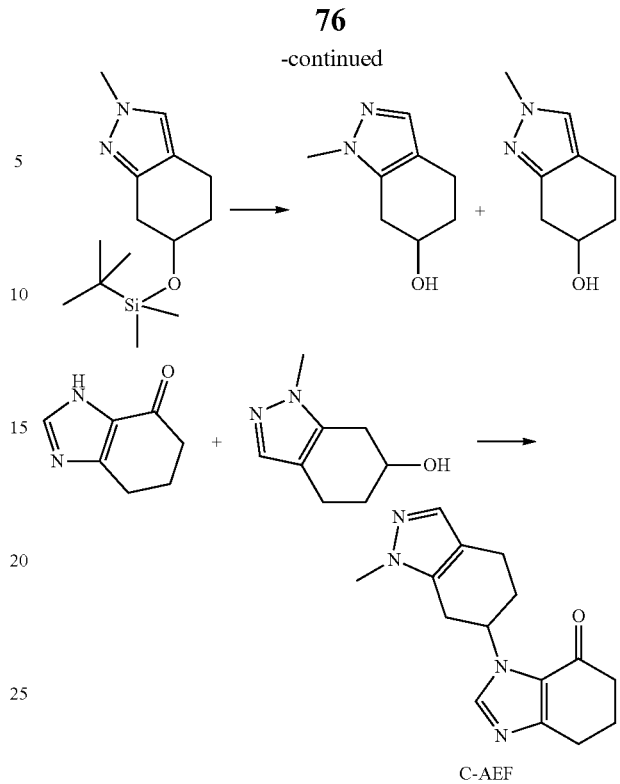

To a mixture of 2.50 g (18.1 mmol) 4,5,6,7-tetrahydro-1H-indazol-6-ol in 20 mL of DCM is added 6.68 mL (36.2 mmol) di-isopropylethyl amine and 3.55 g (23.5 mmol) t-butyl dimethylsilyl chloride. The mixture becomes heterogenous with stirring overnight. The mixture is diluted with 150 mL EtOAc, quenched with 2×20 mL of sat. NH$_4$Cl. The organic phase is dried with MgSO$_4$, filtered and concentrated. $^1$H NMR indicates the desired material. The crude 6-(tert-butyl-dimethyl-silanyloxy)-4,5,6,7-tetrahydro-1H-indazole is carried on without purification.

To a solution of 4.57 g (18.1 mmol) of 6-(tert-Butyl-dimethyl-silanyloxy)-4,5,6,7-tetrahydro-1H-indazole in 20 mL of DMF is added 1.30 g (32.5 mmol, 60 wt %) NaH in one portion. The mixture stirs for 30 min. To this is added 1.34 mL (21.7 mmol) of MeI in one portion. The mixture is allowed to warm to RT and stirs for 24 h. The mixture is quenched with 20 mL of sat. NH$_4$Cl and diluted with 500 mL EtOAc. The organic phase is washed with 4×100 mL of H$_2$O and 1×200 mL of brine. The organic phase is dried with MgSO$_4$, filtered and concentrated. The crude mixture of 6-(tert-butyl-dimethyl-silanyloxy)-1-methyl-4,5,6,7-tetra-hydro-1H-indazole and 6-(tert-Butyl-dimethyl-silanyloxy)-2-methyl-4,5,6,7-tetrahydro-2H-indazole is contaminated with DMF but carried on. Analysis of the aqueous phase has methylated desilylated material. This material is concentrated and set aside.

To 2.40 g (9.01 mml) of a mixture of 6-(tert-Butyl-dimethyl-silanyloxy)-1-methyl-4,5,6,7-tetrahydro-1H-indazole and 6-(tert-Butyl-dimethyl-silanyloxy)-2-methyl-4,5,6,7-tetrahydro-2H-indazole in 20 mL of THF is added 9.00 mL (9.00 mmol) 1M TBAF in THF. The mixture is stirred at RT for 4 h. LC-MS analysis indicated the desired alcohols (2 regioisomers). The mixture is concentrated and 100 mL of H$_2$O is added. The aq. phase is extracted 2×100 mL of Et$_2$O. LC-MS analysis indicates the desired material remains in the aqueous phase. The mixture is concentrated and combined with aqueous fraction from the methylation reaction. This material is filtered through 300 g of C-18 SiO$_2$ (0-100% H20/MeOH). The fractions containing product were concentrated and submitted for MS-triggered purification (Sunfire C18 5 uM OBD 30×150 mm, 1-10% CAN/H2O[0.1% TFA], 65 mL/min, 9 min run+8 min wash) to give 0.56 g of regioisomer 1-methyl-4,5,6,7-tetrahydro-1H-indazol-6-ol and 0.60 g of regioisomer 2-methyl-4,5,6,7-tetrahydro-2H-indazol-6-ol.

To 3,5,6,7-tetrahydrobenzimidazol-4-one, di-t-butylazodicarboxylate (DBAD) and alcohol in 5 mL of THF was added the phosphine. The mixture stirred for 36 h at RT. LC-MS analysis indicated poor converion. The mixture was heated at 50° C. for 72 h. LC-MS analysis indicated small amounts of desired coupling. The mixture was concentrated and partitioned between 20 mL of hexanes/MeOH. Extract 1×20 mL of MeOH. The MeOH extracts were combined and concentrated. The material was applied to a prep-plate (2 mm) and eluted 1×5% MeOH/CH$_2$Cl$_2$ w/scraping of the UV active band to give impure band.

The impure mixture is re-applied to a SiO$_2$ prep-plate chromatography to give 11.2 mg of desired product (C-AEF).

Example 12: Synthesis of 1-(3-chloro-4-cyano-phenyl)-7-oxo-4,5,6,7-tetrahydro-1H-benzoimidazole-5-carboxylic acid amide (C-AEB-A and C-AEB-B)

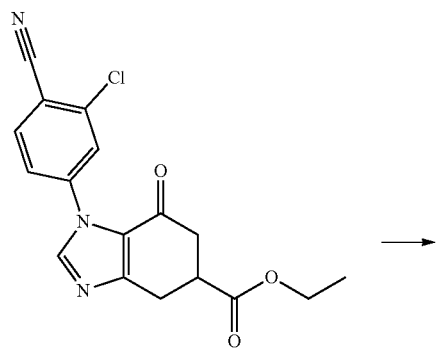

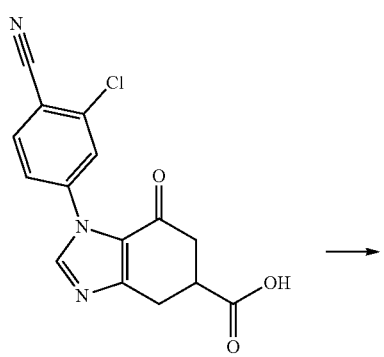

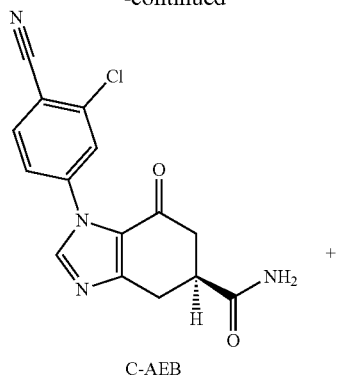

C-AEB

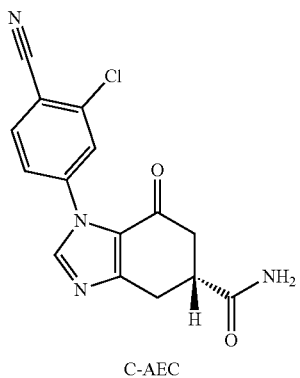

C-AEC

To a vial containing 100 mg (0.29 mmol) C-AAY in 1 mL of THF/1 ml of MeOH/0.5 mL of water, is added 13.5 mg (0.33 mmol) LiOH. The reaction mixture is stirred at room temperature for 2 hours. To the reaction mixture is added 1N HCl until pH=7. The reaction mixture is concentrated to afford crude 1-(3-chloro-4-cyano-phenyl)-7-oxo-4,5,6,7-tetrahydro-1H-benzoimidazole-5-carboxylic acid, and carried on without purification.

To a stirred solution of 130 mg (0.41 mmol) of the above carboxylic acid, 285 mg (0.62 mmol) HATU, 106 mg (0.82 mmol) di-isopropylethyl amine in 3 mL of DMF is added 2.0 mL of hydroxyamine. The reaction mixture is stirred at room temperature for 18 hours. The reaction mixture is concentrated. The residue is diluted with EtOAc, washed with water, and brine. The organic phase is dried Na$_2$SO$_4$ and concentrated. The crude amide is purified by column chromatography (0-5% MeOH/CH$_2$Cl$_2$) to afford 73.0 mg of racemic 1-(3-chloro-4-cyano-phenyl)-7-oxo-4,5,6,7-tetrahydro-1H-benzoimidazole-5-carboxylic acid amide. The racemate amide is resolved by (Lux 5u Cellulose 13 cm, 35% (1:1:1MeOH:EtOH:iPA):CO$_2$, 120 gr/min, 120 bar, 40° C.) to give 12.0 mg of the first-eluting enantiomer, 1-(3-chloro-4-cyano-phenyl)-7-oxo-4,5,6,7-tetrahydro-1H-benzoimidazole-5-carboxylic acid amide (C-AEB-A) and 14.0 mg of second-eluting enantiomer (C-AEB-B).

Example 13: (R)-1-(3-chloro-4-cyano-phenyl)-7-oxo-4,5,6,7-tetrahydro-1H-benzoimidazole-5-carboxylic acid dimethylamide (C-AEE)

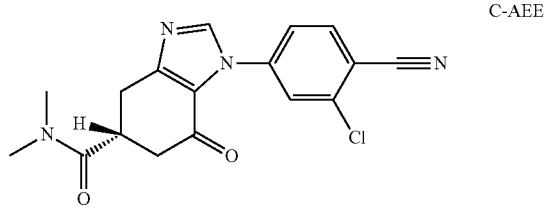 [SMILES: CN(C)C(=O)[C@H]1CC(=O)c2c(ncn2-c2ccc(C#N)c(Cl)c2)C1]

C-AEE

To a vial 92 mg (0.3 mmol) of 1-(3-chloro-4-cyano-phenyl)-7-oxo-4,5,6,7-tetrahydro-1H-benzoimidazole-5-carboxylic acid in 2 mL of DMF is added 166 mg (0.4 mmol) HATU, 75 mg (0.6 mmol) di-isopropylethyl amine and 0.44 mL (0.9 mmol) of a 2.0 M dimethylamine solution in THF. The reaction mixture was stirred at room temperature for 18 hours. The reaction mixture is concentrated. The residue is diluted with EtOAc, washed with water, brine then dried under anhydrous $Na_2SO_4$. The solution is filtered and concentrated. The residue is purified by column chromatography (0-5% $MeOH/CH_2Cl_2$) to afford 58 mg of racemic 1-(3-chloro-4-cyano-phenyl)-7-oxo-4,5,6,7-tetrahydro-1H-benzoimidazole-5-carboxylic acid dimethylamide as light brown solid. The racemic amide is resolved by (LUX Amylose-2, 21×250 mm) 25%(60:40MeOH:iPA):CO2, 80 gr/min, 120 bar, 40 C) to give 12.0 of first-eluting enantiomer of 1-(3-chloro-4-cyano-phenyl)-7-oxo-4,5,6,7-tetrahydro-1H-benzoimidazole-5-carboxylic acid dimethylamide and 14.0 mg of second-eluting enantiomer (C-AEE).

Example 14: (R)-1-(3-Chloro-4-cyano-phenyl)-7-oxo-4,5,6,7-tetrahydro-1H-benzoimidazole-5-carboxylic acid methylamide (C-AEH)

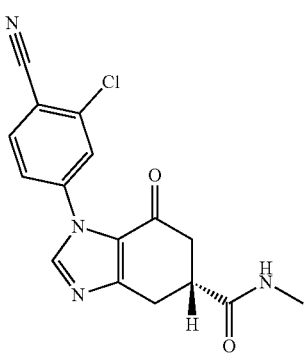

C-AEH

To a vial 126 mg (0.4 mmol) of 1-(3-chloro-4-cyano-phenyl)-7-oxo-4,5,6,7-tetrahydro-1H-benzoimidazole-5-carboxylic acid in 10 mL of DMF is added 212 mg (0.55 mmol) HATU, 0.37 mL (2.00 mmol) di-isopropylethyl amine and methyl amine hydrochloride. The mixture is stirred for 16 h. LC-MS indicates the desired product. The mixture is concentrated, diluted with 100 mL EtOAc and quenched with 50 mL of sat. $NH_4Cl$. The organic phase is washed with 4×80 mL of $H_2O$ and 1×20 mL of brine. The organic phase is dried with $MgSO_4$, filtered and concentrated. The crude material is applied to a $SiO_2$ column and purified (125 g, 0-100% EtOAc/heptanes) to give 70 mg of racemic amide. The racemic amide is resolved by (LUX Amylose-2, 21×250mm) 40%(1:1:1MeOH:EtOH:iPA):$CO_2$, 60 gr/min, 130bar, 40° C. to give 26 mg of the distomer of 1-(3-Chloro-4-cyano-phenyl)-7-oxo-4,5,6,7-tetrahydro-1H- benzoimidazole-5-carboxylic acid methylamide (first eluting enantiomer) and 28 mg of eutomer (C-AEH) (second eluting enantiomer).

Example 15: 2-Chloro-4-(5-hydroxymethyl-7-oxo-4,5,6,7-tetrahydro-benzoimidazol-1-yl)-benzonitrile (C-AED)

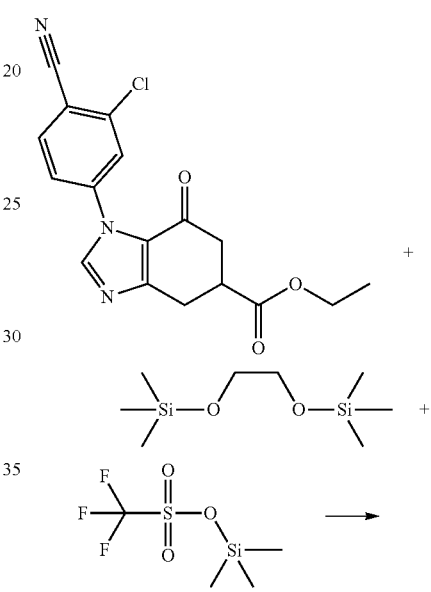

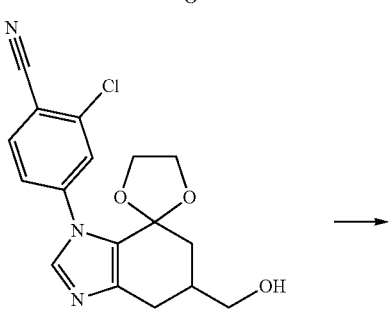

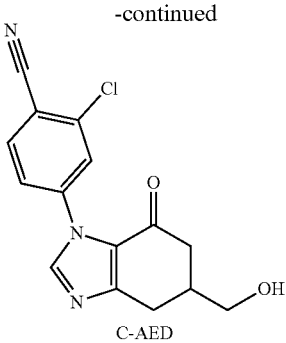

C-AED

To a vial of 155 mg (0.45 mmol) of C-AAY in 2 mL of CH$_2$Cl$_2$ at −78° C., is added 800 mg, (3.88 mmol) of 1,2-bis(trimethylsiloxy)ethane and 160 mg (0.72 mmol) of trimethylsilyl trifluoromethanesulfonate. The reaction mixture is warmed up and stirred at room temperature for 24 hours. The reaction mixture is washed with sat, NaHCO$_3$ and concentrated to give 155 mg crude 1-(3-chloro-4-cyano-phenyl)-7-spirodioxolane-4,5,6,7-tetrahydro-1H-benzoimidazole-5-carboxylic acid ethyl ester.

To a vial of 155 mg (0.4 mmol) crude 1-(3-chloro-4-cyano-phenyl)-7-spirodioxolane-4,5,6,7-tetrahydro-1H-benzoimidazole-5-carboxylic acid ethyl ester in 0.5 mL of MeOH and 0.5 mL of THF, is added LiBH$_4$ drop-wise. The reaction mixture is stirred at room temperature for 3 hours. The reaction mixture is diluted with EtOAc, washed with 1N HCl/water, brine, dried under anhydrous Na$_2$SO$_4$. The solution is filtered and concentrated to afford 100 mg of crude 2-chloro-4-(5-hydroxymethyl-7-dioxolane-4,5,6,7-tetrahydro-benzoimidazol-1-yl)-benzonitrile.

To a vial of 90 mg (0.23 mmol) of crude 2-chloro-4-(5-hydroxymethyl-7-dioxolane-4,5,6,7-tetrahydro-benzoimidazol-1-yl)-benzonitrile in 3 mL of THF/1 mL of water, was added 1 mL of 1N HCl. The reaction mixture is stirred at room temperature for 2 hours. The reaction mixture is diluted with EtOAc, washed with sat. NaHCO$_3$, brine, dried under anhydrous Na$_2$SO$_4$. The solution is filtered and concentrated. The residue is purified by column chromatography (0-5% MeOH/CH$_2$Cl$_2$) to afford 15 mg of 2-Chloro-4-(5-hydroxymethyl-7-oxo-4,5,6,7-tetrahydro-benzoimidazol-1-yl)-benzonitrile (C-AED) as an off-white solid.

Example 16: 6-(7-oxo-4,5,6,7-tetrahydro-benzoimidazol-1-yl)-3,4-dihydro-2H-quinoline-1-carboxylic acid amide (C-ADZ)

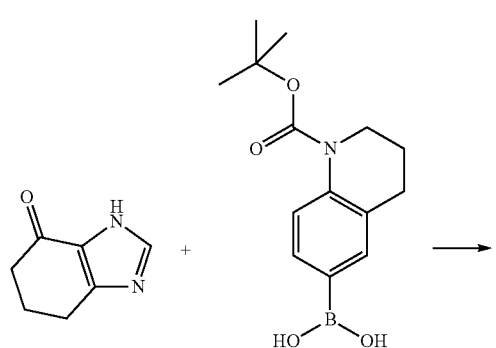

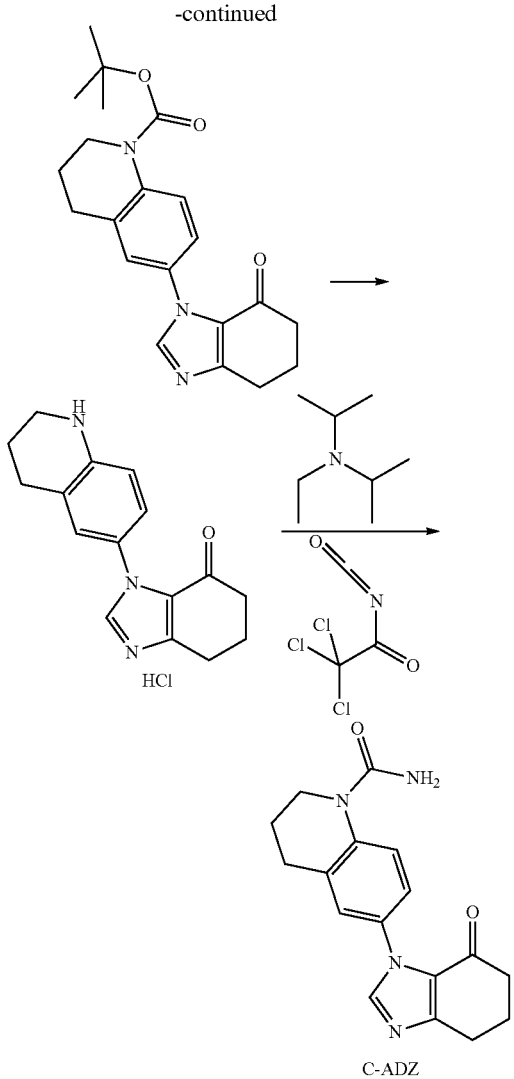

C-ADZ

The boronic acid,3,5,6,7-tetrahydrobenzimidazol-4-one and Cu salt were combined in a vial and dissolved into 4 mL of MeOH. The mixture was rigorously stirred open to the air for 72 h. LC-MS analysis indicated the desired product. The mixture was filtered through diatomaceous earth and concentrated. Applied to a SiO2 column and purified (0-10% MeOH/CH$_2$Cl$_2$) to give impure fractions containing the desired mass. Repeat SiO$_2$ purification 0-100% EtOac/Hepatanes. Applied concentrated products to a SiO$_2$ prep plates.to give 63.3 mg of the desired intermediate.

To 62 mg (0.17 mmol) of 6-(7-oxo-4,5,6,7-tetrahydro-benzoimidazol-1-yl)-3,4-dihydro-2H-quinoline-1-carboxylic acid tert-butyl ester in 2 mL of CH$_2$Cl$_2$ is added 1.0 mL (1.00 mmol) of a 1M solution of HCl in dioxane. The mixture is stirred for 72 h and turned heterogeneous. The mixture is concentrated to give crude 3-(1,2,3,4-tetrahydro-quinolin-6-yl)-3,5,6,7-tetrahydro-benzoimidazol-4-one as an HCl salt.

60 mg (0.20 mmol) of 3-(1,2,3,4-tetrahydro-quinolin-6-yl)-3,5,6,7-tetrahydro-benzoimidazol-4-one HCl salt is suspended in DCM. To this is added 0.07 mL (0.40 mmol) of di-isopropylethyl amine and 0.04 mL (0.3 mmol) of trichloroacetyl isocyanate. The mixture is stirred at RT for 1 h. 1 mL of 1N KOH in MeOH is added and stirred overnight. The mixture is directly purified via the Gilson Prep HPLC system (5%-70% CH$_3$CN/H$_2$O). Concentration and freebasing the pure fraction gave 20.7 mg of 6-(7-oxo-4,5,6,7-tetrahydro-benzoimidazol-1-yl)-3,4-dihydro-2H-quinoline-1-carboxylic acid amide (C-ADZ).

Example 17: 6-(5,5-dimethyl-7-oxo-4,5,6,7-tetrahydro-benzoimidazol-1-yl)-1-methyl-3,4-dihydro-1H-[1,8]naphthyridin-2-one (C-AEG)

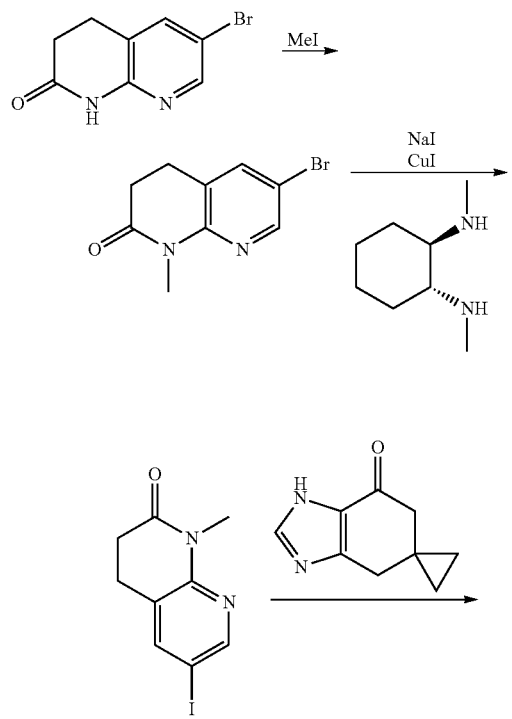

To a round bottom flask is added 500 mg (2.20 mmol) of 6-bromo-3,4-dihydro-1H-[1,8]naphthyridin-2-one in 10 mL of DMF, followed by the addition of 132 mg (3.30 mmol, 60 wt %) NaH. The reaction mixture is stirred at room temperature for 30 minutes, followed by the addition of 625 mg (4.40 mmol) MeI. The reaction mixture is stirred at room temperature for 18 hours. The reaction mixture is concentrated and the residue is dissolved in EtOAc, washed with water, brine, dried under anhydrous Na$_2$SO$_4$. The solution is filtered and concentrated. The residue is purified by column chromatography (0-50% EtOAc/heptane) to afford 503 mg of 6-bromo-1-methyl-3,4-dihydro-1H-[1,8]naphthyridin-2-one as a white solid.

To a vial is added 503 mg (2.09 mmol) of 6-bromo-1-methyl-3,4-dihydro-1H-[1,8]naphthyridin-2-one, 625 mg (4.17 mmol) sodium iodide and 39.7 mg (0.21 mmol) copper(I) iodide. To this is added mL of 1,4-dioxane, followed by the addition of 29.7 mg (0.21 mmol) of trans-N,N'-dimethylcyclohexane-1,2-diamine. The reaction mixture is stirred at 110° C. for 18 hours. The reaction mixture is concentrated. The residue is dissolved in EtOAc, washed with water, brine, dried under anhydrous Na$_2$SO$_4$. The solution is filtered and concentrated. The residue is purified by column chromatography (0-50% EtOAc/heptane) to afford 570 mg of 6-iodo-1-methyl-3,4-dihydro-1H-[1,8]naphthyridin-2-one as an off-white solid product.

To a vial of 369 mg (1.28 mmol) 6-Iodo-1-methyl-3,4-dihydro-1H-[1,8]naphthyridin-2-one, 208 mg (1.28 mmol) of 6,6-spirocyclopropyl-3,5,6,7-tetrahydro-benzoimidazol-4-one, 836 mg (2.57 mmol) of cesium carbonate, 49 mg (0.26 mmol) CuI and 38 mg (0.26 mmol) 8-hydroxyquinoline is added 7 mL of DMSO. The vial is sealed and the reaction mixture is stirred at 130° C. for 18 hours. An additional 20 mol % CuI and hydroxy quinoline is added. The mixture is heated at 150° C. for 8 h. The mixture is cooled to RT and stirred for 18 h. The reaction mixture is filtered and partitioned between 50 mL of EtOAc and H$_2$O. The organic phase is washed with 3×20 mL water and 1×50 mL of brine. The organic phase is dried with MgSO$_4$, filtered and concentrated. The residue is applied to a SiO$_2$ prep plate (2mm) and eluted with 2.5% MeOH/CH$_2$Cl$_2$ to give two bands which were impure. The impure bands are combined and purified via prep plate SiO$_2$ purification (50% acetone/hexanes) to give 19.7 mg of 6-(5,5-dimethyl-7-oxo-4,5,6,7-tetrahydro-benzoimidazol-1-yl)-1-methyl-3,4-dihydro-1H-[1,8]naphthyridin-2-one (C-AEG).

Example 18: 2-Chloro-4-(7-oxo-4,5,6,7-tetrahydro-benzoimidazol-1-yl)-benzonitrile (C-AEA)

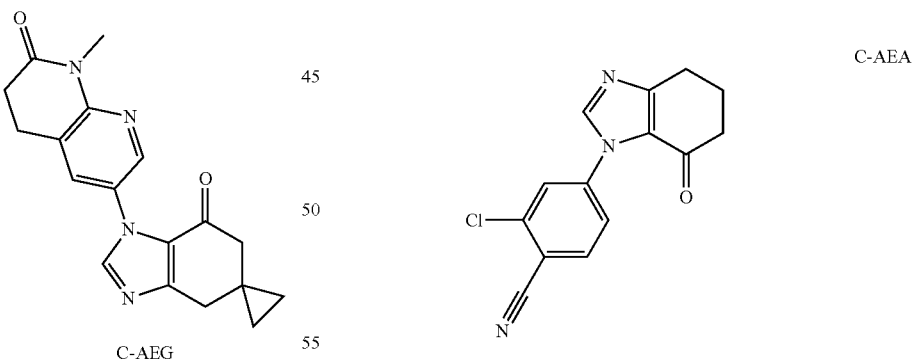

To a vial was added imidazole, 3-chloro-4-cyanophenylboronic acid and tetrakis(acetonitrile)copper(I)hexafluorophosphate in 15 mL of MeOH. The reaction mixture was stirred at room temperature open to air for 80 hours. The reaction mixture was filtered. The solvent was concentrated. The reside was loaded to a column. The column was eluted with 0-10% MeOH/CH$_2$Cl$_2$. The product fractions were collected to give a mixture of regioisomers. The mixture was applied to a SiO$_2$ prep-plate (1mm) and eluted w/100% EtOAc (2×) to give 61.1 mg C-AEA and 15.9 mg of coupled products.

Examples 19: Synthesis of 4-(6,6-dimethyl-7-oxo-4,5,6,7-tetrahydro-benzoimidazol-1-yl)-benzonitrile (C-ADX) and 4-(6-methyl-7-oxo-4,5,6,7-tetrahydro-benzoimidazol-1-yl)-benzonitrile (C-ADY)

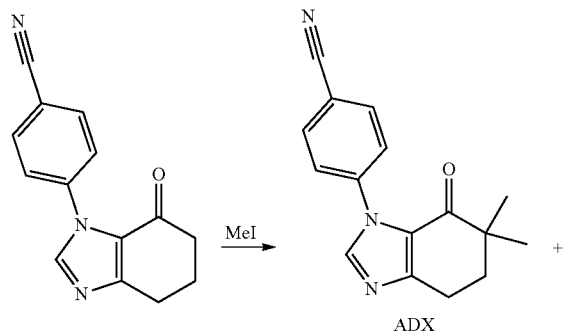

to warm over 2 h. LC-MS indicates multiple peaks in which mono and di-methylated species were identified. The mixture is quenched with 20 mL of sat. $NH_4Cl$, diluted with 50 mL EtOAc, washed with 2×20 mL of $H_2O$ and 1×20 mL of brine. The organic phase is dried with $MgSO_4$, filtered and concentrated. The crude mixture was applied to a $SiO_2$ column and purified (40 g, 0-100% EtOAc/heptanes) to give 16.8 mg of 4-(6,6-dimethyl-7-oxo-4,5,6,7-tetrahydro-benzoimidazol-1-yl)-benzonitrile (C-ADX) and 20 mg of 4-(6-methyl-7-oxo-4,5,6,7-tetrahydro-benzoimidazol-1-yl)-benzonitrile (C-ADY).

LCMS data are measured using the methods set forth in Table 2. Data for compounds in Table 1 are shown in Table 3. Compounds that were separated into their enantiomers are shown by separate entries for enantiomer A and enantiomer B. The first to elute is designated enantiomer A, for example C-AAZ-A, and the second to elute is enantiomer B, for example C-AAZ-B.

TABLE 2

LC/MS Methods

| Method | Mobile Phase A | Mobile Phase B | Gradient | Flow (mL/min.) | Column |
|---|---|---|---|---|---|
| A | 95% Water 5% MeCN + 0.05% Formic Acid | MeCN + 0.05% Formic Acid | 90% A to 100% B in 1.19 min. hold at 100% B to 1.70 min. | 0.8 | BEH 2.1 × 50 mm C18, 1.7 μm particle diameter |
| B | 100% Water + 0.1% Formic Acid | MeCN + 0.1% Formic Acid | 95% A to 95% B in 1.0 min. hold at 95% B for 0.3 min | 0.8 | BEH 2.5 × 50 mm C18, 1.7 μm particle diameter |
| C | 100% Water + 0.1% Formic Acid | MeCN + 0.1% Formic Acid | 90% A to 99% B in 1.5 min hold at 99% B for 1 min | 0.5 | Thermo Scientific, Aquasil C18, 50 × 2.1 mm, 5 μm |
| D | 95% Water 5% Acetonitrile 2.5 mM Ammonium Bicarbonate | MeCN | 95% A to 95% B in 1.19 min. hold at 95% B to 1.70 min | 0.8 | BEH 2.1 × 50 mm C18, 1.7 μm particle diameter |

-continued

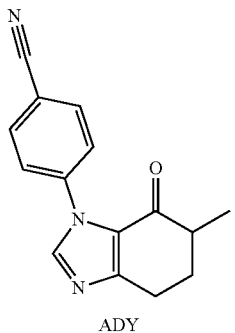

ADY

To a flask containing 231 mg (0.97 mmol) 4-(7-oxo-4,5,6,7-tetrahydro-benzoimidazol-1-yl)-benzonitrile (C-AAL) in 5 mL of dry THF at −78° C. is added 2.42 mL (2.42 mmol) LHMDS dropwise. The mixture is stirred for 30 min. To this is added 0.12 mL (1.95 mmol) MeI. The mixture is allowed

TABLE 3

LC/MS Data

| Cpd No. | $(M + H)^+$ | HPLC method | HPLC Retention Time (min) |
|---|---|---|---|
| C-AAA | 296.0 | A | 0.51 |
| C-AAB | 255.0 | A | 0.51 |
| C-AAC | 296.1 | A | 0.45 |
| C-AAD | 297.0 | A | 0.7 |
| C-AAE | 255 | B | 0.56 |
| C-AAF | 310.0 | A | 0.55 |
| C-AAG | 267 | B | 0.52 |
| C-AAH | 267 | B | 0.54 |
| C-AAI | 271.3 | A | 0.58 |
| C-AAJ | 285 | A | 0.64 |
| C-AAK | 278.0 | A | 0.69 |
| C-AAL | 238.1 | C | 0.925 |
| C-AAM | 283.9 | B | 0.56 |
| C-AAN | 298.1 | B | 0.57 |

TABLE 3-continued

LC/MS Data

| Cpd No. | (M + H)+ | HPLC method | HPLC Retention Time (min) |
|---|---|---|---|
| C-AAO | 322.1 | A | 0.62 |
| C-AAP | 366.1 | A | 0.56 |
| C-AAQ | 343.2 | A | 0.67 |
| C-AAR | 317.6 | A | 0.7 |
| C-AAS | 308.1 | A | 0.54 |
| C-AAT | 278.2 | A | 0.76 |
| C-AAU | 292.1 | A | 0.79 |
| C-AAV | 336 | A | 0.72 |
| C-AAW | 298.5 | A | 0.78 |
| C-AAX | 264.2 | A | 0.62 |
| C-AAY | 345.2 | A | 0.77 |
| C-AAZ-A | 269.0 | A | 0.64 |
| C-AAZ-B | 269.0 | A | 0.64 |
| C-ABA-A | 329.2 | A | 0.64 |
| C-ABA-B | 329.2 | A | 0.64 |
| C-ABB | 268.1 | A | 0.51 |
| C-ABC | 277 | C | 2.87 |
| C-ABD | 309.6 | C | 3.06 |
| C-ABE | 300 | C | 2.98 |
| C-ABF | 311 | C | 2.99 |
| C-ABG |  | C | 3.01 |
| C-ABH | 311 | C | 3.09 |
| C-ABI | 292.8 | C | 2.96 |
| C-ABJ | 332.9 | C | 3.09 |
| C-ABK | 275.1 | C | 2.93 |
| C-ABL | 282.9 | C | 2.78 |
| C-ABM | 292.9 | C | 2.99 |
| C-ABN | 275.1 | C | 2.94 |
| C-ABO | 283.9 | C | 2.83 |
| C-ABP | 258.7 | C | 2.84 |
| C-ABQ | 299.9 | C | 2.98 |
| C-ABR | 270.9 | C | 2.8 |
| C-ABS | 265.7 | C | 2.89 |
| C-ABT | 275.9 | C | 2.81 |
| C-ABU | 285.4 | C | 2.82 |
| C-ABV | 279.8 | C | 2.89 |
| C-ABW | 298.8 | C | 2.86 |
| C-ABX | 265.7 | C | 2.83 |
| C-ABY | 279 | C | 2.84 |
| C-ABZ | 308.7 | C | 2.95 |
| C-ACA | 240.9 | C | 2.8 |
| C-ACB | 255.6 | A | 0.81 |
| C-ACC | 280 | C | 3.08 |
| C-ACD | 296.2 | A | 0.52 |
| C-ACE | 289 | A | 0.87 |
| C-ACF | 288.2 | A | 0.88 |
| C-ACG | 312.6 | A | 0.86 |
| C-ACH | 322.2 | A | 0.64 |
| C-ACI | 308.7 | C |  |
| C-ACJ | 244.1 | A | 0.4 |
| C-ACK | 246.9 | A | 0.68 |
| C-ACL | 259.1 | D | 0.9 |
| C-ACM | 374.1 | A | 1 |
| C-ACN | 325.1 | D | 0.9 |
| C-ACO | 301.2 | D | 1.15 |
| C-ACP | 261.1 | D | 1 |
| C-ACQ | 281.1 | D | 0.9 |
| C-ACR | 276.1 | D | 0.5 |
| C-ACS | 295.1 | D | 1 |
| C-ACT | 261.1 | D | 0.6 |
| C-ACU | 295.7 | D | 0.99 |
| C-ACV | 297.4 | C | 1.35 |
| C-ACW | 309.1 | D | 1 |
| C-ACX | 249.4 | A | 0.54 |
| C-ACY | 295.2 | D | 0.7 |
| C-ACZ | 313.1 | C | 3.15 |
| C-ADA | 219.1 | D | 0.7 |
| C-ADB | 322.2 | A | 0.57 |
| C-ADC | 277.2 | D | 0.7 |
| C-ADD | 327.1 | D | 0.7 |
| C-ADE | 412.2 | D | 0.6 |
| C-ADF | 297.1 | A | 0.61 |
| C-ADG | 282.4 | C | 2.02 |
| C-ADH | 295.1 | C | 2.11 |
| C-ADI | 263.5 | A | 0.64 |
| C-ADJ | 267.2 | C | 2.06 |
| C-ADK | 253.2 | A | 0.77 |
| C-ADL | 272.4 | A | 0.57 |
| C-ADM | 303.7 | D | 0.95 |
| C-ADN | 320 | A | 0.78 |
| C-ADO | 273.2 | C | 2.94 |
| C-ADP | 333.2 | C | 2.72 |
| C-ADQ | 285.2 | C | 2.9 |
| C-ADR | 255 | C | 2.79 |
| C-ADS | 356.2 | A | 0.52 |
| C-ADT | 368.9 | A | 0.51 |
| C-ADU | 404.4 | C | 2.7 |
| C-ADV | 313.2 | A | 0.68 |
| C-ADW | 239.0 | A | 0.69 |
| C-ADX | 266.5 | A | 0.72 |
| C-ADY | 252.4 | A | 0.68 |
| C-ADZ | 311.2 | A | 0.46 |
| C-AEA | 272.5 | A | 0.59 |
| C-AEB-A | 315.5 | A | 0.58 |
| C-AEB-B | 315.5 | A | 0.58 |
| C-AED | 303.2 | A | 0.54 |
| C-AEE | 344.2 | A | 0.57 |
| C-AEF | 271.1 | B | 0.46 |
| C-AEG | 323.1 | A | 0.72 |
| C-AEH | 329.4 | A | 0.55 |

ASSESSMENT OF BIOLOGICAL ACTIVITY

Preparation of Cynomolgus Adrenal Mitochondria

The aldosterone synthase and cortisol synthase inhibition assays employ cynomolgus adrenal gland mitochondria as the source of aldosterone synthase (CYP11B2) and cortisol synthase (CYP11B1). Mitochondria are prepared from frozen cynomolgus monkey adrenal glands according to Method A described in by J. D. McGarry et al. (Biochem. J., 1983, 214, 21-28), with a final resuspension in the AT buffer described in R. Yamaguchi et al. (Cell Death and Differentiation, 2007, 14, 616-624), frozen as aliquots in liquid nitrogen and stored at −80° C. until use. One unit of CYP11B2 and CYP11B1 activity in these preparations is defined as the amount of enzyme that generates 1 pmol of product in one hour under the conditions described.

Inhibition of Aldosterone Synthase

The compounds of the invention may be evaluated for aldosterone synthase inhibition by the following assay:

Assays are performed in 96-well format in a final volume of 60 microL/well, containing 100 mM potassium phosphate, pH 7.4, 1% (v/v) DMSO, and additionally, 2 µM of corticosterone and 50 units of CYP11B2 activity. Reactions are started by the addition of NADPH to 1 mM and allowed to proceed for 90 minutes at 37° C. Reactions are terminated by the addition of 60 µL of MeCN containing an internal standard for mass spectrometry. One hundred microliters are then transferred to a glass filter plate and centrifuged at 570×g for 5 minutes and the filtrate is collected. Reaction product aldosterone is quantified by mass spectrometry. To determine the assay blank value (0% activity), NADPH is omitted from some reactions.

Dose dependent inhibition is quantified by the inclusion of compound at various concentrations. Maximum activity (100%) is defined by reactions containing NADPH, but without compound. Activities at each concentration are expressed as a percentage of the maximum activity (y-axis) and plotted against concentration of compound (x-axis) and the concentration corresponding to 50% activity ($IC_{50}$) determined using the XLFit curve-fitting program using a 4-parameter logistic model.

Inhibition of Cortisol Synthesis

Assays are performed as for aldosterone synthase except for the use of 150 units of CYP11B1, 11-deoxycortisol as substrate and cortisol measured as product.

Representative compounds of the present invention were tested for activity in the above assays. Preferred compounds have an $IC_{50}$<1,000 nM and more preferred compounds have an $IC_{50}$<100 nM in the aldosterone synthase inhibition assay. Preferred compounds have at least 100-fold selectivity for aldosterone synthase inhibition over cortisol synthase (CYP11B1) inhibition. As examples, data for representative compounds from Table 1 are shown in Table 4. Data for individual enantiomers are indicated by separate entries for enantiomers A and B

TABLE 4

Aldosterone Synthase and Cortisol Synthase Inhibition

| Cpd No. | Aldosterone Inhibition $IC_{50}$ (nM) | Cortisol Inhibition $IC_{50}$ (μM) | Selectivity |
|---|---|---|---|
| C-AAA | 510 | >30000 | 59 |
| C-AAB | 85 | 23000 | 270 |
| C-AAC | 720 | >30000 | 42 |
| C-AAD | 150 | >30000 | 200 |
| C-AAE | 11 | 9400 | 890 |
| C-AAF | 37 | 10000 | 270 |
| C-AAG | 100 | >30000 | 300 |
| C-AAH | 48 | >30000 | 630 |
| C-AAI | 160 | >30000 | 180 |
| C-AAJ | 440 | >30000 | 67 |
| C-AAK | 34 | 17000 | 500 |
| C-AAL | 19 | 4600 | 250 |
| C-AAM | 120 | >30000 | 240 |
| C-AAN | 84 | >30000 | 360 |
| C-AAO | 77 | 2300 | 30 |
| C-AAP | 460 | >30000 | 65 |
| C-AAQ | 44 | 2900 | 66 |
| C-AAR | 69 | 5000 | 73 |
| C-AAS | 240 | 14000 | 61 |
| C-AAT | 3.8 | 480 | 130 |
| C-AAU | 10 | 51 | 5.0 |
| C-AAV | 47 | 14000 | 300 |
| C-AAW | 5.0 | 220 | 43 |
| C-AAX | 8.5 | 1900 | 230 |
| C-AAY | 7.3 | 5100 | 690 |
| C-AAZ-A | 300 | >30000 | 100 |
| C-AAZ-B | 70 | >30000 | 430 |
| C-ABA-A | 16 | 1000 | 63 |
| C-ABA-B | 16 | 850 | 53 |
| C-ABB | 250 | >30000 | 120 |
| C-ABC | 10 | 650 | 63 |
| C-ABD | 3.1 | 370 | 120 |
| C-ABE | 1.3 | 110 | 79 |
| C-ABF | 3.8 | 610 | 160 |
| C-ABG | 4.2 | 500 | 120 |
| C-ABH | 22 | 5200 | 240 |
| C-ABI | 4.8 | 910 | 190 |
| C-ABJ | 75 | 95000 | 1300 |
| C-ABK | 19 | 7000 | 370 |
| C-ABL | 59 | 8800 | 150 |
| C-ABM | 4.7 | 770 | 160 |
| C-ABN | 15 | 1000 | 67 |
| C-ABO | 130 | 35000 | 270 |
| C-ABP | 21 | 1100 | 52 |
| C-ABQ | 280 | >100000 | 360 |
| C-ABR | 130 | 21000 | 150 |
| C-ABS | 250 | 10000 | 39 |

TABLE 4-continued

Aldosterone Synthase and Cortisol Synthase Inhibition

| Cpd No. | Aldosterone Inhibition $IC_{50}$ (nM) | Cortisol Inhibition $IC_{50}$ (μM) | Selectivity |
|---|---|---|---|
| C-ABT | 230 | 6900 | 30 |
| C-ABU | 34 | 4200 | 120 |
| C-ABV | 6.6 | 130 | 20 |
| C-ABW | 310 | 7500 | 24 |
| C-ABX | 17 | 1300 | 80 |
| C-ABY | 130 | 7300 | 56 |
| C-ABZ | 73 | 27000 | 370 |
| C-ACA | 250 | 12000 | 46 |
| C-ACB | 22 | 4400 | 200 |
| C-ACC | 5.5 | 1000 | 190 |
| C-ACD | 60 | 55000 | 920 |
| C-ACE | 20 | 630 | 32 |
| C-ACF | 10 | 590 | 57 |
| C-ACG | 12 | 93 | 7.5 |
| C-ACH | 16 | 4900 | 300 |
| C-ACI | 62 | 18000 | 290 |
| C-ACJ | 30 | 13000 | 440 |
| C-ACK | 260 | 6100 | 24 |
| C-ACL | 180 | 16000 | 87 |
| C-ACM | 53 | >30000 | 570 |
| C-ACN | 24 | 11000 | 460 |
| C-ACO | 420 | 14000 | 34 |
| C-ACP | 24 | 5900 | 240 |
| C-ACQ | 220 | >30000 | 130 |
| C-ACR | 785 | >30000 | 38 |
| C-ACS | 93 | 26000 | 280 |
| C-ACT | 780 | >30000 | 38 |
| C-ACU | 110 | 9400 | 85 |
| C-ACV | 860 | >30000 | 35 |
| C-ACW | 24 | 7200 | 300 |
| C-ACX | 870 | >30000 | 35 |
| C-ACY | 110 | 1700 | 15 |
| C-ACZ | 34 | 1400 | 41 |
| C-ADA | 530 | 12000 | 23 |
| C-ADB | 540 | 7400 | 14 |
| C-ADC | 250 | 45000 | 180 |
| C-ADD | 540 | 11000 | 20 |
| C-ADE | 58 | 1900 | 33 |
| C-ADF | | | |
| C-ADG | 47 | 61000 | 1300 |
| C-ADH | 10 | 29000 | 2900 |
| C-ADI | 470 | 19000 | 41 |
| C-ADJ | 2.8 | 1200 | 420 |
| C-ADK | 21 | 8400 | 400 |
| C-ADL | 22 | 7900 | 360 |
| C-ADM | 72 | >30000 | 420 |
| C-ADN | 190 | >30000 | 160 |
| C-ADO | 56 | 5400 | 96 |
| C-ADP | 92 | 1600 | 17 |
| C-ADQ | 96 | 2100 | 22 |
| C-ADR | 97 | 9400 | 97 |
| C-ADS | 290 | 43000 | 150 |
| C-ADT | 290 | 29000 | 100 |
| C-ADU | 210 | 6200 | 30 |
| C-ADV | 25 | 35 | 1.4 |
| C-ADW | 290 | 25000 | 85 |
| C-ADX | 14 | 2140 | 153 |
| C-ADY | 24 | 3640 | 152 |
| C-ADZ | 99 | >30000 | 300 |
| C-AEA | 8.7 | 1100 | 130 |
| C-AEB-A | 590 | >30000 | 51 |
| C-AEB-B | 32 | >30000 | 940 |
| C-AED | 18 | 8600 | 470 |
| C-AEE | 190 | >30000 | 150 |
| C-AEF | 190 | >30000 | 160 |
| C-AEG | 670 | 8900 | 13 |
| C-AEH | 57 | >30000 | 526 |

METHODS OF THERAPEUTIC USE

In accordance with the invention, there are provided novel methods of using the compounds of formula (I). The compounds disclosed herein effectively inhibit aldosterone synthase. The inhibition of aldosterone synthase is an attractive means for preventing and treating a variety of diseases or conditions that can be alleviated by lowering levels of aldosterone. Thus, the compounds are useful for the treatment of diseases and conditions as described in the Background section, including the following conditions and diseases:

Diabetic kidney disease including dieabetic nephropathy;
Non-diabetic kidney disease including glomerulosclerosis, glomerulonephritis, IGA nephropathy, nephritic syndrome and focal segmental glomerulosclerosis (FSGS);
Cardiovascular diseases including hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism;
Adrenal hyperplasia and primary and secondary hyperaldosteronism.

These disorders have been well characterized in man, but also exist with a similar etiology in other mammals, and can be treated by pharmaceutical compositions of the present invention.

Accordingly, a compound of formula I according to any of the embodiments described herein or a pharmaceutically acceptable salt thereof may be used for the preparation of a medicament for treating a disease or disorder mediated by aldosterone synthase, including diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N .G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:
1. A compound of formula I

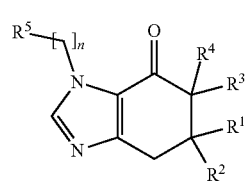

wherein:
$R^1$ and $R^2$ are each independently selected from the group consisting of —H, —CO$_2$Et, —C(O)NH$_2$, —C(O)NHCH$_3$, —C(O)N(CH$_3$)$_2$, —C$_{1-3}$alkyl and —CH$_2$OH; or
$R^1$ and $R^2$, together with the carbon they are bonded to, may form a spiro ring selected from the group consisting of C$_{3-4}$cycloalkyl, tetrahydrofuran and tetrahydropyran;
$R^3$ and $R^4$ are both —H, or if $R^1$ and $R^2$ are both —H, $R^3$ and $R^4$ are independently selected from the group consisting of —H and —CH$_3$;
$R^5$ is selected from the group consisting of
phenyl substituted with one to two groups selected from the group consisting of —CN, —C$_{1-3}$alkyl optionally substituted with —OH, —C$_{3-6}$cycloalkyl, —Cl, —F, —C(O)N(Me)(—CH$_2$CH$_2$OH), —C(O)NH(—CH$_2$CH$_2$SO$_2$CH$_3$), —C(O)C$_{1-3}$alkyl, —N(Me)$_2$, —NHC(O)C$_{1-3}$alkyl,
—SO$_2$Cl$_{1-3}$alkyl, —CF$_3$, 3-hydroxy-pyrrolidine-1-carbonyl and [1,2,4]triazolyl;
aryl or carbocycle selected from the group consisting of C$_{3-6}$cycloalkyl, bicycle[2.2.1]heptyl, decahydronaphthalenyl, indanyl, spiro[3.3]hept-1-yl, 6,7,8,9-tetrahydro-5H-benzocycloheptenyl and 1,2,3,4-tetrahydronaphthalenyl, wherein said aryl or carbocycle is optionally substituted with —CN, —Br, —OC$_{1-3}$alkyl and phenyl;
heterocyclyl selected from the group consisting of benzo[1,3]dioxolyl, 3H-benzoxazolyl, -chromanyl, 3,4-dihydro-2H-benzol[b][1,4]dioxepinyl, 2,3-dihydrobenzo[1,4]dioxinyl, 2,3-dihydrobenzofuranyl, 4H-benzo[1,4]oxazinyl, 2,3-dihydro- 1H-indolyl, 1,3-dihydroisobenzofuranyl, 1,4-dihydro-2H-isoquinolinyl, 3,4-dihydro-1H-[1,8]napthyridinyl, 3,4-dihydro-2H-pyrido[3,2-b][1,4]oxazinyl, 3,4-dihydroquinolinyl, 2-oxa-spiro[3,3heptyl, piperidinyl, tetrahydrofuranyl, tetrahydropyranyl, 5,6,7,8-tetrahydroquinazolinyl, 1,2,3,4-tetrahydroquinolinyl, wherein said heterocyclyl is optionally substituted with one to two groups selected from the group consisting of—C(O)CH$_3$, —C$_{1-3}$alkyl, -oxo and —C(O)NH$_2$; and
heteroaryl selected from the group consisting of 1H-indazolyl and pyridyl, [1,2,3]-thiadiazolyl, wherein said heteroaryl is optionally substituted with one to two groups selected from the group consisting of —C$_{1-3}$alkyl, —Cl and —CN;
n is 0 or 1;
or a salt thereof.

2. The compound of formula I according to claim 1, wherein:
R$^1$ and R$^2$ are independently selected from the group consisting of —H, —CO$_2$Et, —C(O)NH$_2$, —C(O)NHCH$_3$, —CH$_3$ and —CH$_2$OH; or
R$^1$ and R$^2$, together with the carbon they are bonded to, may form a spiro ring selected from the group consisting of C$_{3-4}$cycloalkyl, tetrahydrofuran and tetrahydropyran;
R$^3$ and R$^4$ are both —H, or if R$^1$ and R$^2$ are both —H, R$^3$ and R$^4$ are independently selected from the group consisting of —H and —CH$_3$;
R$^5$ is selected from the group consisting of
phenyl, substituted with one to two groups selected from the group consisting of —CN, —C$_{1-3}$alkyl, cyclopropyl, —Cl, —F, —NHC(O)CH$_3$, —SO$_2$CH$_3$ and —CF$_3$;
aryl or carbocycle selected from the group consisting of cyclohexyl, indanyl, spiro[3.3]hept-1-yl, 6,7,8,9-tetrahydro-5H-benzocycloheptenyl and 1,2,3,4-tetrahydronaphthalenyl, wherein said aryl or carbocycle is optionally substituted with —CN, —Br and —OC$_{1-2}$alkyl;
heterocyclyl selected from the group consisting of benzo[1,3]dioxolyl, 2,3-dihydrobenzofuranyl, 4H-benzo[1,4]oxazinyl, 1,3-dihydroisobenzofuranyl, 3,4-dihydroquinolinyl and 1,2,3,4-tetrahydroquinolinyl, wherein said heterocyclyl is optionally substituted with one to two groups selected from the group consisting of —C(O)CH$_3$, —CH$_3$, —oxo and —C(O)NH$_2$; and
1H-indazolyl, optionally substituted with —CH3;
n is 0 or 1;
or a salt thereof.

3. The compound of formula I according to claim 1, wherein
R$^3$ and R$^4$ are both —H;
or a salt thereof.

4. The compound of formula I according to claim 1, wherein
R$^1$ and R$^2$ are independently selected from the group consisting of —H, —CO$_2$Et, —C(O)NH$_2$, —C(O)NHCH$_3$, —C(O)N(CH$_3$)$_2$, —C$_{1-3}$alkyl and —CH$_2$OH, provided that R$^1$ and R$^2$ are not both —H; or
R$^1$ and R$^2$, together with the carbon they are bonded to, may form a spiro ring selected from the group consisting of C$_{1-4}$cycloalkyl;
or a salt thereof.

5. The compound of formula I according to claim 1, wherein
n is 0;
or a salt thereof.

6. The compound of formula I according to claim 1, wherein
n is 1;
or a salt thereof.

7. The compound according to claim 1 selected from the group consisting of

| Cpd No. | Structure |
|---|---|
| C-AAA | 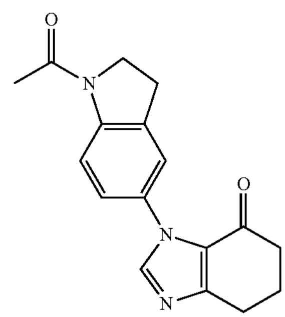 [SMILES: CC(=O)N1CCc2cc(-n3cnc4c3C(=O)CCC4)ccc21] |
| C-AAB | 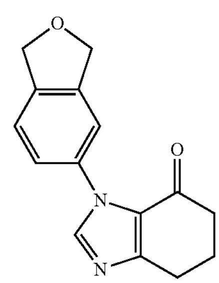 [SMILES: O=C1CCCc2ncn(-c3ccc4c(c3)COC4)c21] |
| C-AAC | 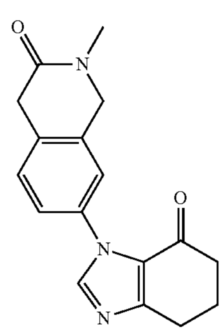 [SMILES: CN1Cc2cc(-n3cnc4c3C(=O)CCC4)ccc2CC1=O] |

| Cpd No. | Structure |
|---|---|
| C-AAD | 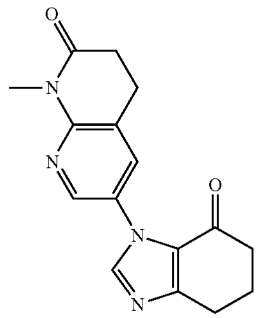 [SMILES: CN1C(=O)CCc2cc(-n3cnc4c3C(=O)CCC4)cnc21] |
| C-AAE | 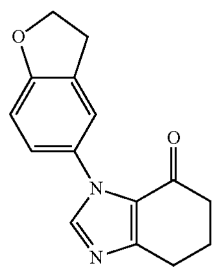 [SMILES: O=C1CCCc2ncn(-c3ccc4c(c3)CCO4)c21] |
| C-AAF | 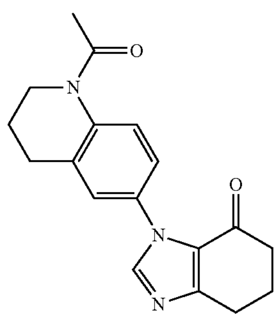 [SMILES: CC(=O)N1CCCc2cc(-n3cnc4c3C(=O)CCC4)ccc21] |
| C-AAG | 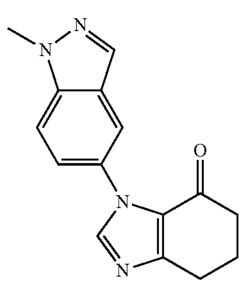 [SMILES: Cn1ncc2cc(-n3cnc4c3C(=O)CCC4)ccc21] |
| C-AAH | 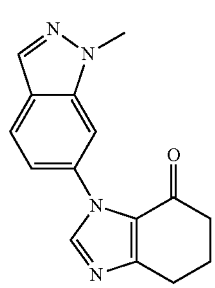 [SMILES: Cn1ncc2ccc(-n3cnc4c3C(=O)CCC4)cc21] |
| C-AAI | 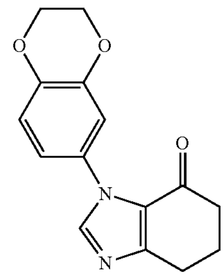 [SMILES: O=C1CCCc2ncn(-c3ccc4c(c3)OCCO4)c21] |
| C-AAJ | 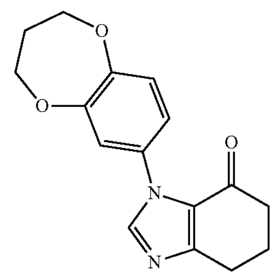 [SMILES: O=C1CCCc2ncn(-c3ccc4c(c3)OCCCO4)c21] |
| C-AAK | 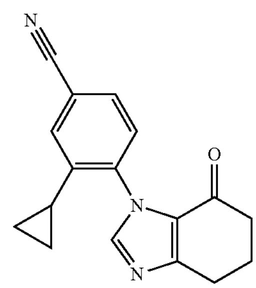 [SMILES: N#Cc1ccc(-n2cnc3c2C(=O)CCC3)c(C2CC2)c1] |
| C-AAL | 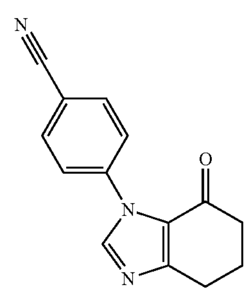 [SMILES: N#Cc1ccc(-n2cnc3c2C(=O)CCC3)cc1] |
| C-AAM | 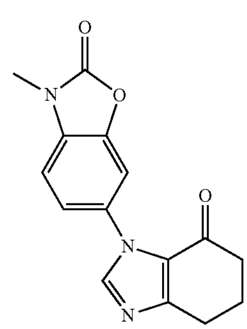 [SMILES: Cn1c(=O)oc2cc(-n3cnc4c3C(=O)CCC4)ccc21] |

| Cpd No. | Structure |
|---|---|
| C-AAN | 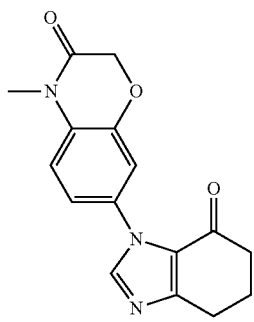 [SMILES: CN1C(=O)COc2cc(-n3cnc4c3C(=O)CCC4)ccc21] |
| C-AAO | 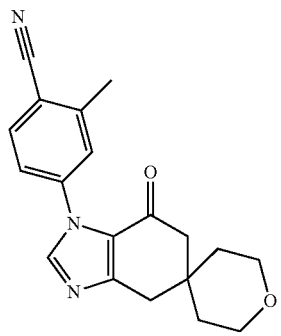 [SMILES: Cc1cc(-n2cnc3c2C(=O)CC2(CCOCC2)C3)ccc1C#N] |
| C-AAP | 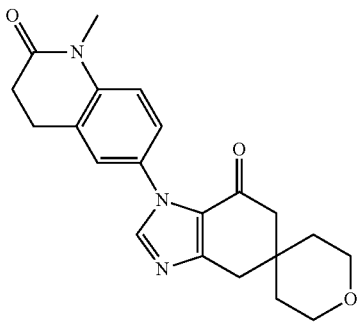 [SMILES: CN1C(=O)CCc2cc(-n3cnc4c3C(=O)CC3(CCOCC3)C4)ccc21] |
| C-AAQ | 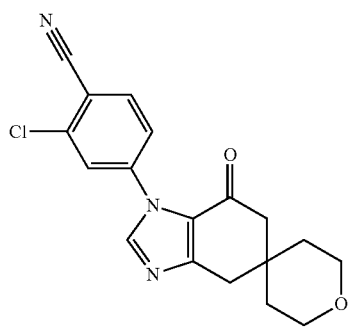 [SMILES: N#Cc1ccc(-n2cnc3c2C(=O)CC2(CCOCC2)C3)cc1Cl] |
| Cpd No. | Structure |
|---|---|
| C-AAR | 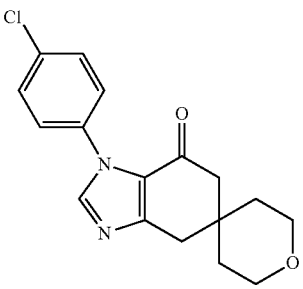 [SMILES: O=C1CC2(CCOCC2)Cc2ncn(-c3ccc(Cl)cc3)c21] |
| C-AAS | 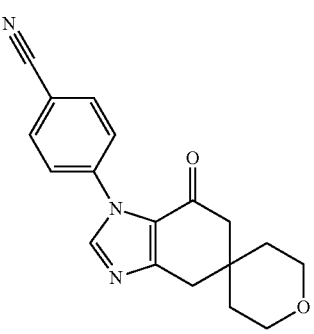 [SMILES: N#Cc1ccc(-n2cnc3c2C(=O)CC2(CCOCC2)C3)cc1] |
| C-AAT | 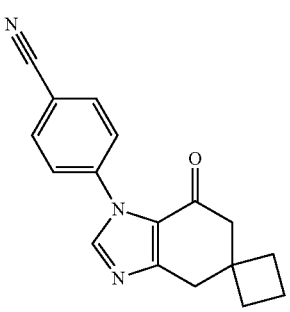 |
| C-AAU | 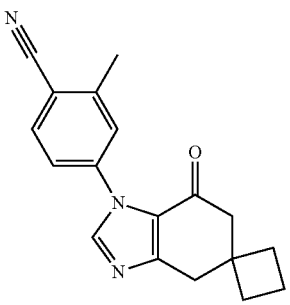 [SMILES: Cc1cc(-n2cnc3c2C(=O)CC2(CCC2)C3)ccc1C#N] |
| C-AAV | 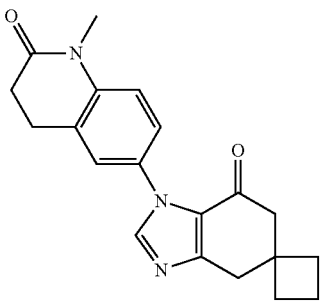 [SMILES: CN1C(=O)CCc2cc(-n3cnc4c3C(=O)CC3(CCC3)C4)ccc21] |

-continued
| Cpd No. | Structure |
|---|---|
| C-AAW | 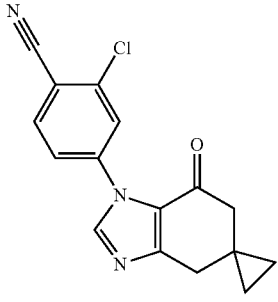 [SMILES: N#Cc1ccc(-n2cnc3c2C(=O)CC2(CC2)C3)cc1Cl] |
| C-AAX | 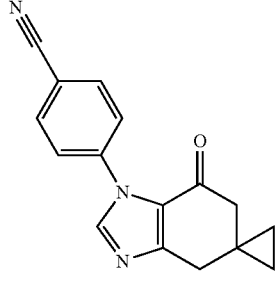 [SMILES: N#Cc1ccc(-n2cnc3c2C(=O)CC2(CC2)C3)cc1] |
| C-AAY | 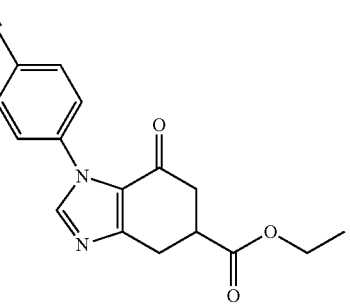 |
| C-AAZ-A | 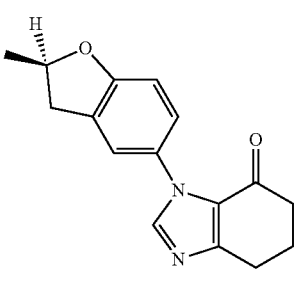 [SMILES: C[C@@H]1Cc2cc(-n3cnc4c3C(=O)CCC4)ccc2O1] |
| C-AAZ-B | 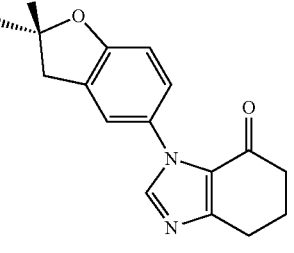 |
-continued
| Cpd No. | Structure |
|---|---|
| C-ABA-A | 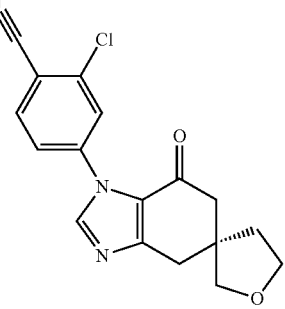 |
| C-ABA-B | 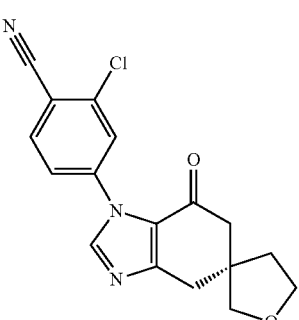 |
| C-ABB | 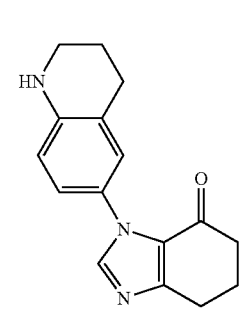 [SMILES: O=C1CCCc2ncn(-c3ccc4c(c3)CCCN4)c21] |
| C-ABC | 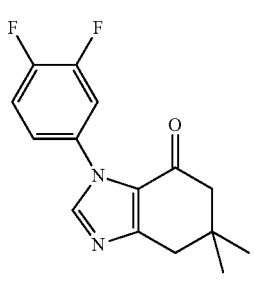 |
| C-ABD | 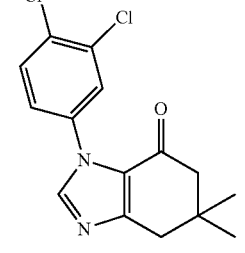 |

| Cpd No. | Structure |
|---|---|
| C-ABE | 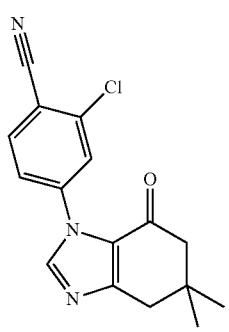 [SMILES: CC1(C)CC(=O)c2c(ncn2-c2ccc(C#N)c(Cl)c2)C1] |
| C-ABF | 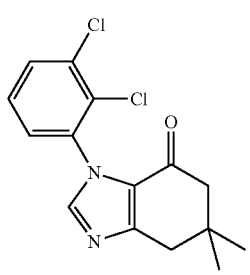 [SMILES: CC1(C)CC(=O)c2c(ncn2-c2cccc(Cl)c2Cl)C1] |
| C-ABG | 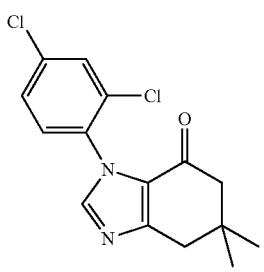 [SMILES: CC1(C)CC(=O)c2c(ncn2-c2ccc(Cl)cc2Cl)C1] |
| C-ABH | 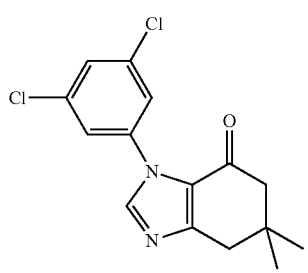 [SMILES: CC1(C)CC(=O)c2c(ncn2-c2cc(Cl)cc(Cl)c2)C1] |
| C-ABI | 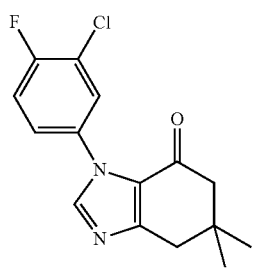 |
| Cpd No. | Structure |
|---|---|
| C-ABK | 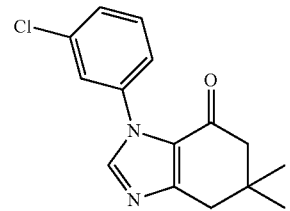 [SMILES: CC1(C)CC(=O)c2c(ncn2-c2cccc(Cl)c2)C1] |
| C-ABL | 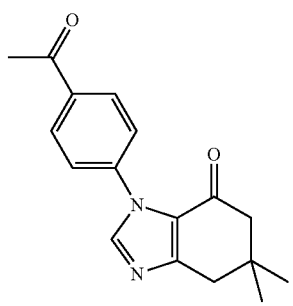 [SMILES: CC(=O)c1ccc(-n2cnc3c2C(=O)CC(C)(C)C3)cc1] |
| C-ABM | 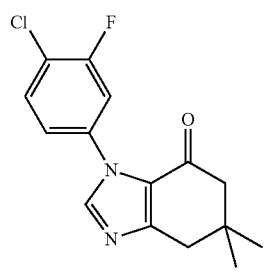 [SMILES: CC1(C)CC(=O)c2c(ncn2-c2ccc(Cl)c(F)c2)C1] |
| C-ABN | 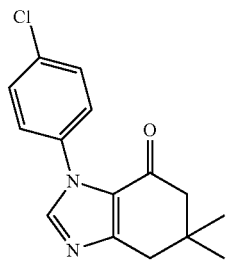 |
| C-ABO | 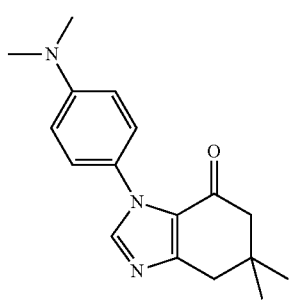 |

| Cpd No. | Structure |
|---|---|
| C-ABP | 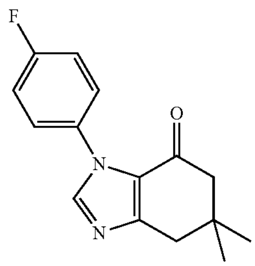 [SMILES: CC1(C)CC(=O)c2c(ncn2-c2ccc(F)cc2)C1] |
| C-ABS | 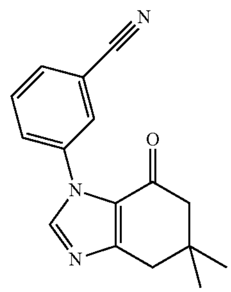 |
| C-ABT | 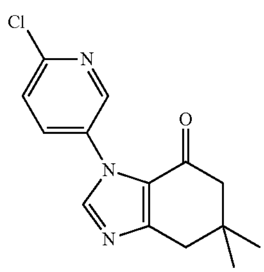 [SMILES: CC1(C)CC(=O)c2c(ncn2-c2ccc(Cl)nc2)C1] |
| C-ABU | 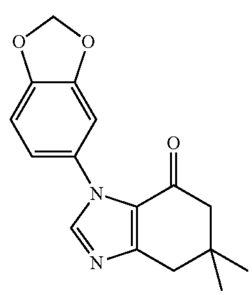 [SMILES: CC1(C)CC(=O)c2c(ncn2-c2ccc3c(c2)OCO3)C1] |
| C-ABV | 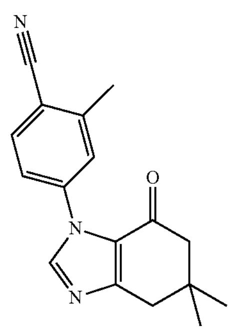 [SMILES: Cc1cc(-n2cnc3c2C(=O)CC(C)(C)C3)ccc1C#N] |
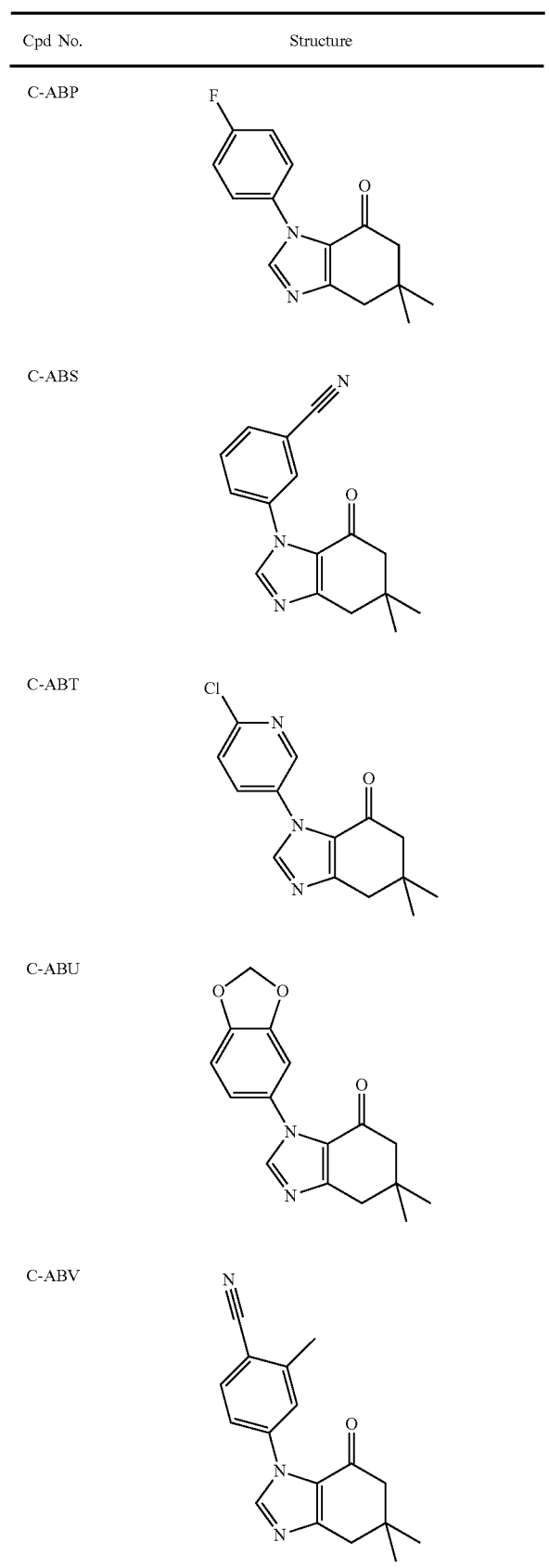
| Cpd No. | Structure |
|---|---|
| C-ABX | 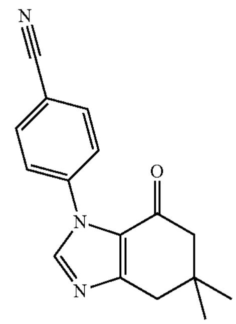 [SMILES: CC1(C)CC(=O)c2c(ncn2-c2ccc(C#N)cc2)C1] |
| C-ABY | 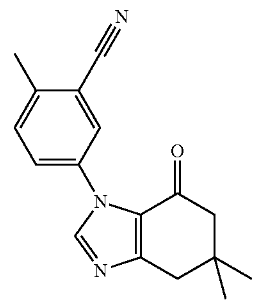 [SMILES: Cc1ccc(-n2cnc3c2C(=O)CC(C)(C)C3)cc1C#N] |
| C-ABZ | 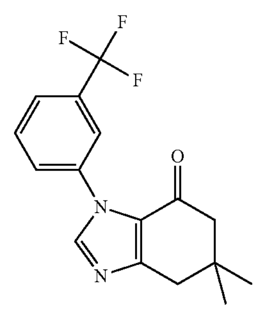 [SMILES: CC1(C)CC(=O)c2c(ncn2-c2cccc(C(F)(F)F)c2)C1] |
| C-ACB | 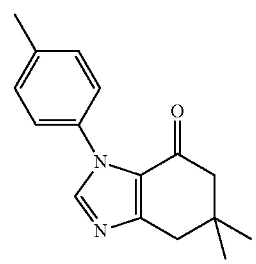 [SMILES: Cc1ccc(-n2cnc3c2C(=O)CC(C)(C)C3)cc1] |
| C-ACC | 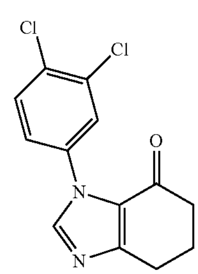 [SMILES: O=C1CCCc2ncn(-c3ccc(Cl)c(Cl)c3)c21] |
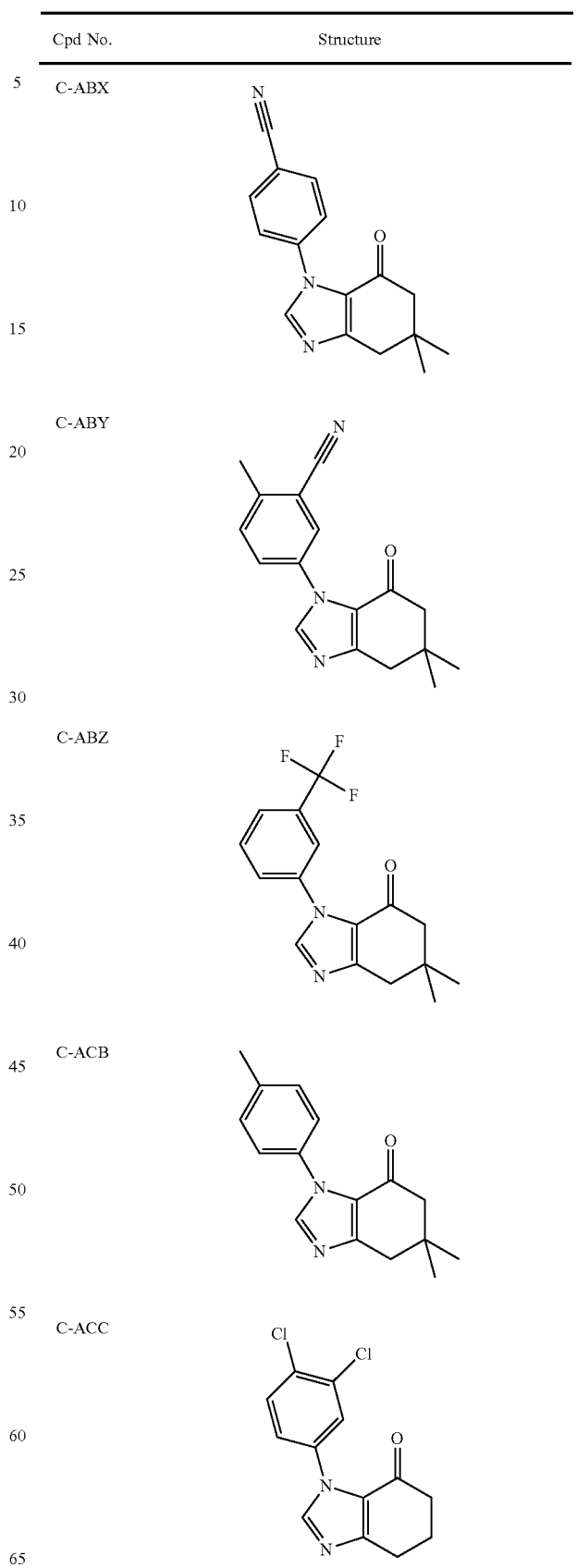

| Cpd No. | Structure |
|---|---|
| C-ACD | 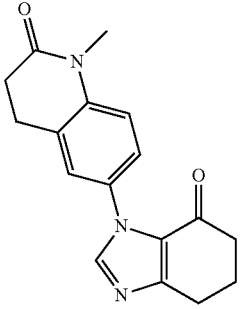 |
| C-ACE | 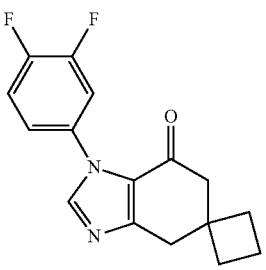 [SMILES: O=C1CC2(CCC2)Cc2ncn(-c3ccc(F)c(F)c3)c21] |
| C-ACF | 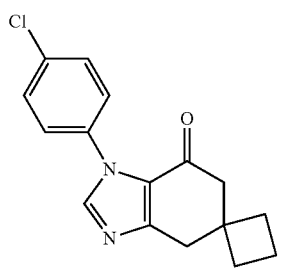 [SMILES: O=C1CC2(CCC2)Cc2ncn(-c3ccc(Cl)cc3)c21] |
| C-ACG | 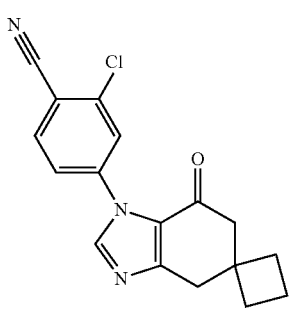 |
| C-ACH | 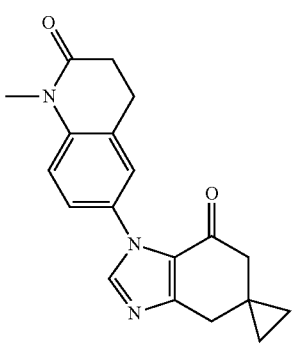 [SMILES: CN1C(=O)CCc2cc(-n3cnc4c3C(=O)CC3(CC3)C4)ccc21] |
| C-ACI | 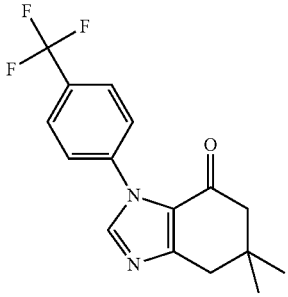 [SMILES: CC1(C)CC(=O)c2c(ncn2-c2ccc(C(F)(F)F)cc2)C1] |
| C-ACJ | 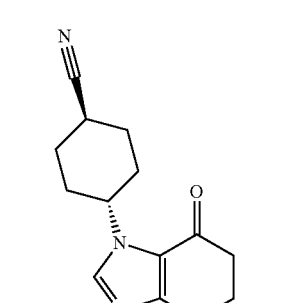 |
| C-ACK | 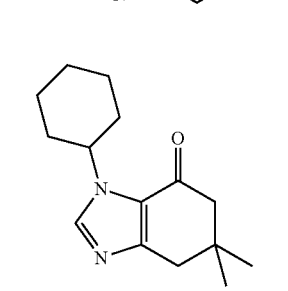 |
| C-ACL | 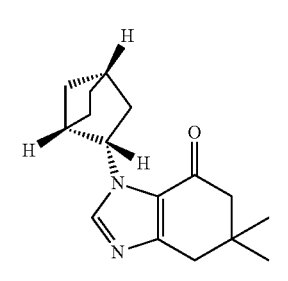 [SMILES: CC1(C)CC(=O)c2c(ncn2[C@H]2C[C@@H]3CC[C@H]2C3)C1] |
| C-ACM | 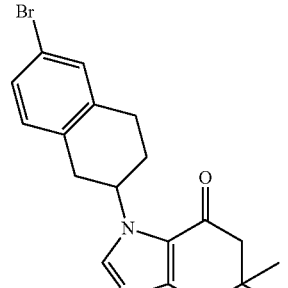 |

| Cpd No. | Structure |
|---|---|
| C-ACN | (6-methoxy-tetrahydronaphthalen-2-yl) substituted 6,6-dimethyl-tetrahydrobenzimidazol-4(5H)-one |
| C-ACO | decahydronaphthalen-2-yl substituted 6,6-dimethyl-tetrahydrobenzimidazol-4(5H)-one |
| C-ACP | cyclohexylmethyl substituted 6,6-dimethyl-tetrahydrobenzimidazol-4(5H)-one |
| C-ACQ | indan-1-yl substituted 6,6-dimethyl-tetrahydrobenzimidazol-4(5H)-one |
| C-ACR | (1-methyl-2-oxo-piperidin-5-yl) substituted 6,6-dimethyl-tetrahydrobenzimidazol-4(5H)-one |
| C-ACS | (1,2,3,4-tetrahydronaphthalen-1-yl) substituted 6,6-dimethyl-tetrahydrobenzimidazol-4(5H)-one |
| C-ACT | (2-oxaspiro[3.3]heptan-6-yl) substituted 6,6-dimethyl-tetrahydrobenzimidazol-4(5H)-one |
| C-ACU | (3-phenylcyclobutyl) substituted 6,6-dimethyl-tetrahydrobenzimidazol-4(5H)-one |
| C-ACV | (5,6,7,8-tetrahydroquinazolin-6-yl) substituted 6,6-dimethyl-tetrahydrobenzimidazol-4(5H)-one |
| C-ACW | (6,7,8,9-tetrahydro-5H-benzo[7]annulen-9-yl) substituted 6,6-dimethyl-tetrahydrobenzimidazol-4(5H)-one |

| Cpd No. | Structure |
|---|---|
| C-ACX | 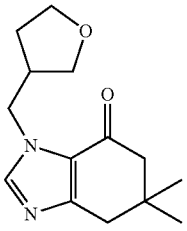 [SMILES: CC1(C)CC(=O)c2c(ncn2CC2CCOC2)C1] |
| C-ACY | 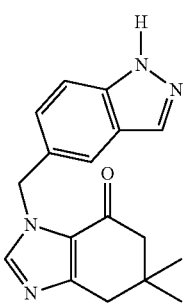 [SMILES: CC1(C)CC(=O)c2c(ncn2Cc2ccc3[nH]ncc3c2)C1] |
| C-ADA | 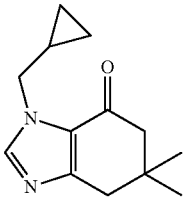 [SMILES: CC1(C)CC(=O)c2c(ncn2CC2CC2)C1] |
| C-ADB | 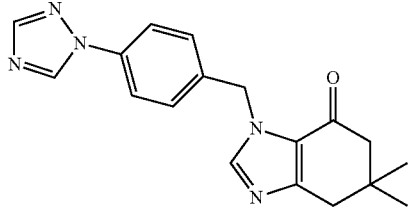 |
| C-ADC | 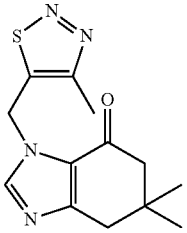 |
| C-ADD | 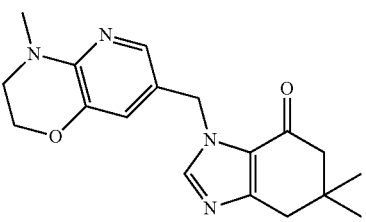 [SMILES: CN1CCOc2cc(Cn3cnc4c3C(=O)CC(C)(C)C4)cnc21] |
| Cpd No. | Structure |
|---|---|
| C-ADE | 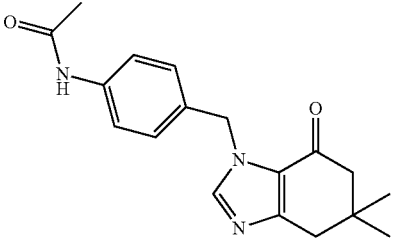 [SMILES: CC(=O)Nc1ccc(Cn2cnc3c2C(=O)CC(C)(C)C3)cc1] |
| C-ADF | 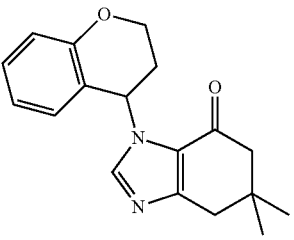 [SMILES: CC1(C)CC(=O)c2c(ncn2C2CCOc3ccccc32)C1] |
| C-ADG | 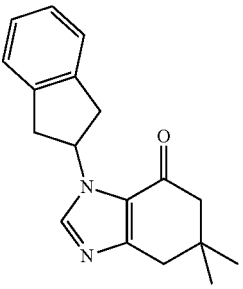 [SMILES: CC1(C)CC(=O)c2c(ncn2C2Cc3ccccc3C2)C1] |
| C-ADH | 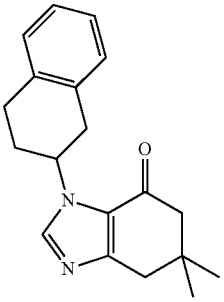 |
| C-ADI | 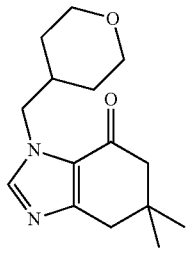 |

| Cpd No. | Structure |
|---|---|
| C-ADJ | 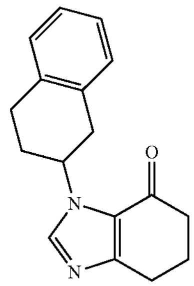 [SMILES: O=C1CCCc2ncn(C3CCc4ccccc4C3)c21] |
| C-ADK | 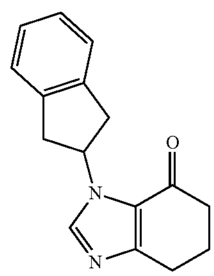 [SMILES: O=C1CCCc2ncn(C3Cc4ccccc4C3)c21] |
| C-ADL | 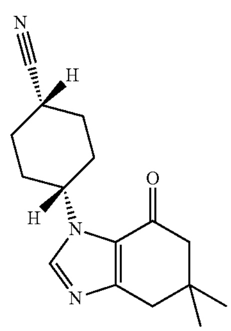 [SMILES: CC1(C)CC(=O)c2c(ncn2[C@H]2CC[C@@H](C#N)CC2)C1] |
| C-ADM | 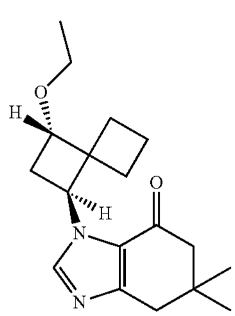 [SMILES: CCO[C@H]1C[C@H](n2cnc3c2C(=O)CC(C)(C)C3)C12CCC2] |
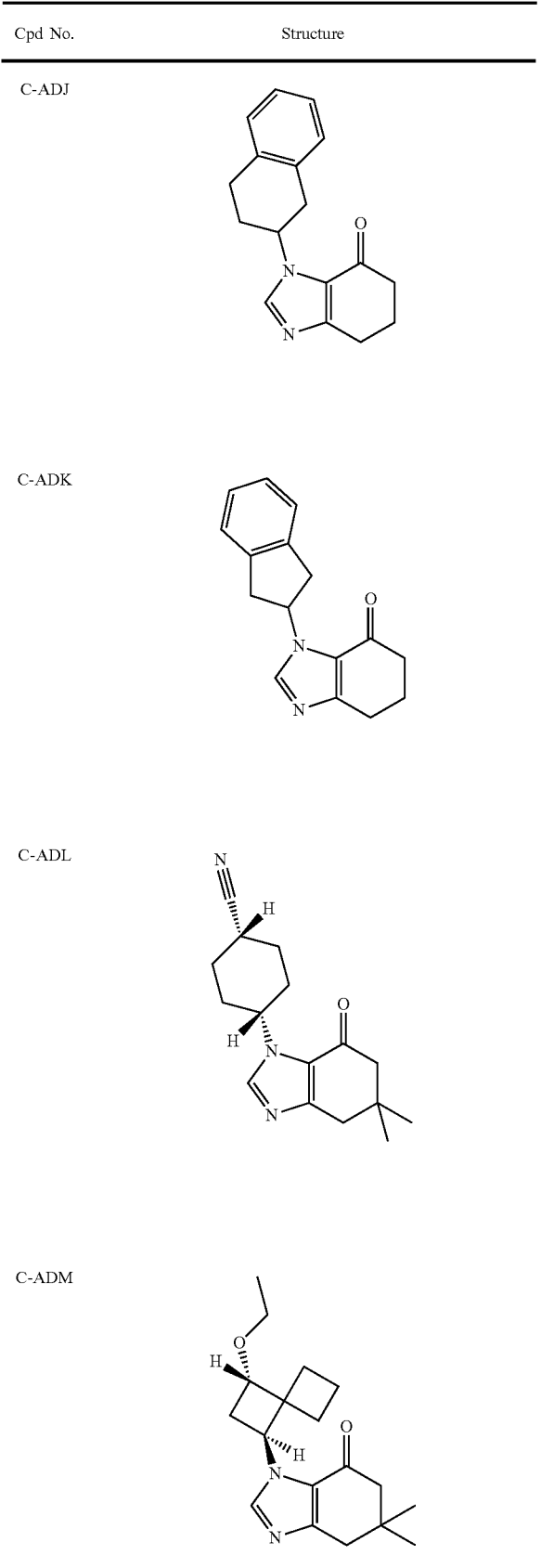
| Cpd No. | Structure |
|---|---|
| C-ADN | 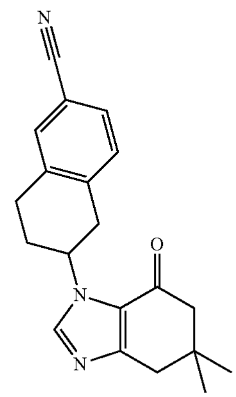 |
| C-ADO | 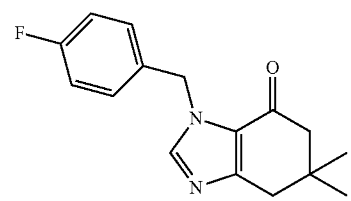 [SMILES: CC1(C)CC(=O)c2c(ncn2Cc2ccc(F)cc2)C1] |
| C-ADP | 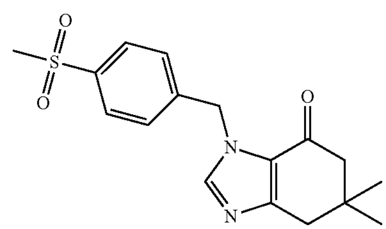 |
| C-ADS | 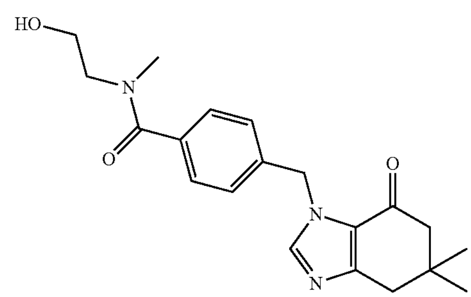 [SMILES: CN(CCO)C(=O)c1ccc(Cn2cnc3c2C(=O)CC(C)(C)C3)cc1] |
| C-ADT | 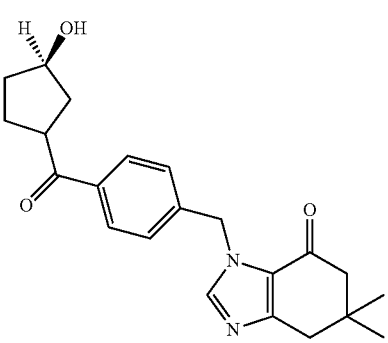 [SMILES: CC1(C)CC(=O)c2c(ncn2Cc2ccc(C(=O)C3CC[C@@H](O)C3)cc2)C1] |
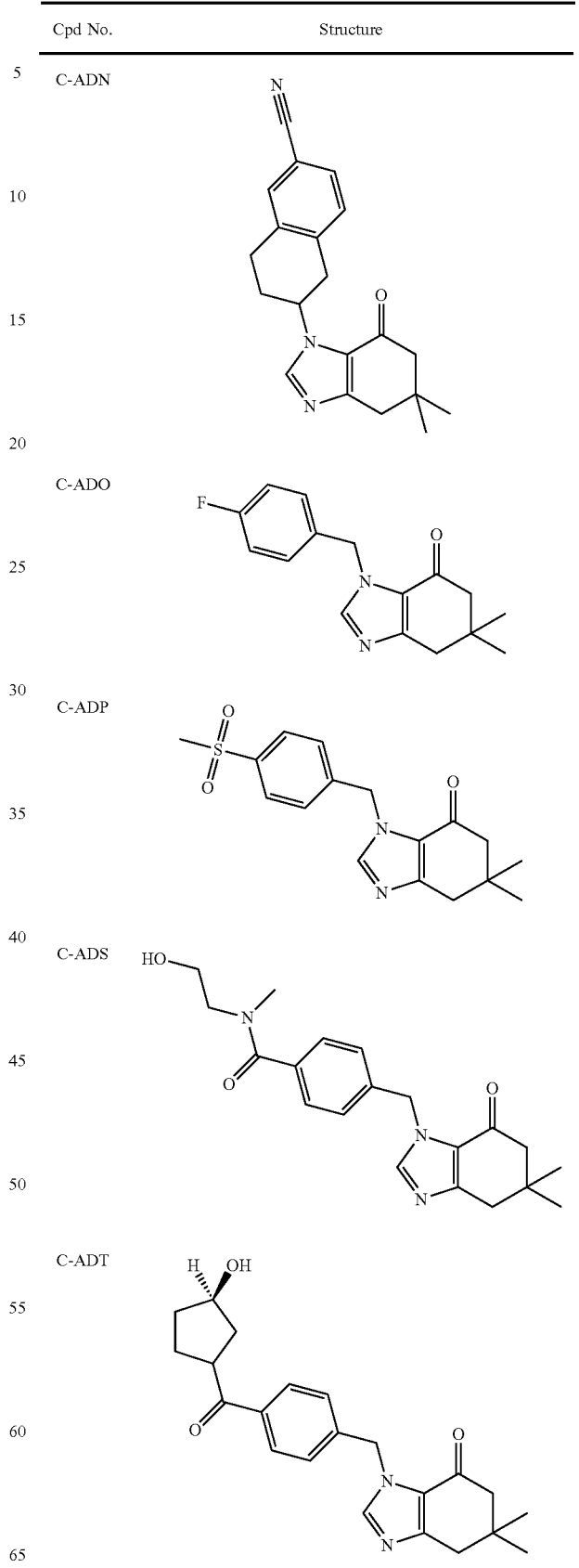

| Cpd No. | Structure |
|---|---|
| C-ADU | 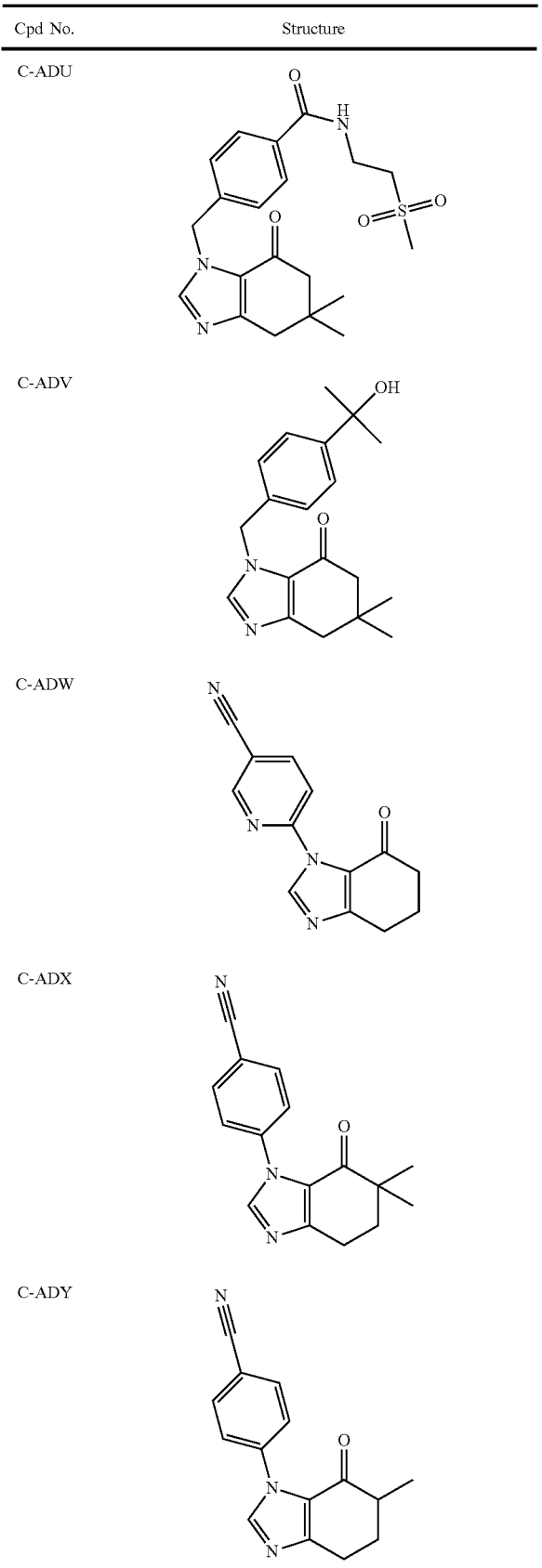 |
| C-ADV | |
| C-ADW | |
| C-ADX | |
| C-ADY | |
| Cpd No. | Structure |
|---|---|
| C-ADZ | 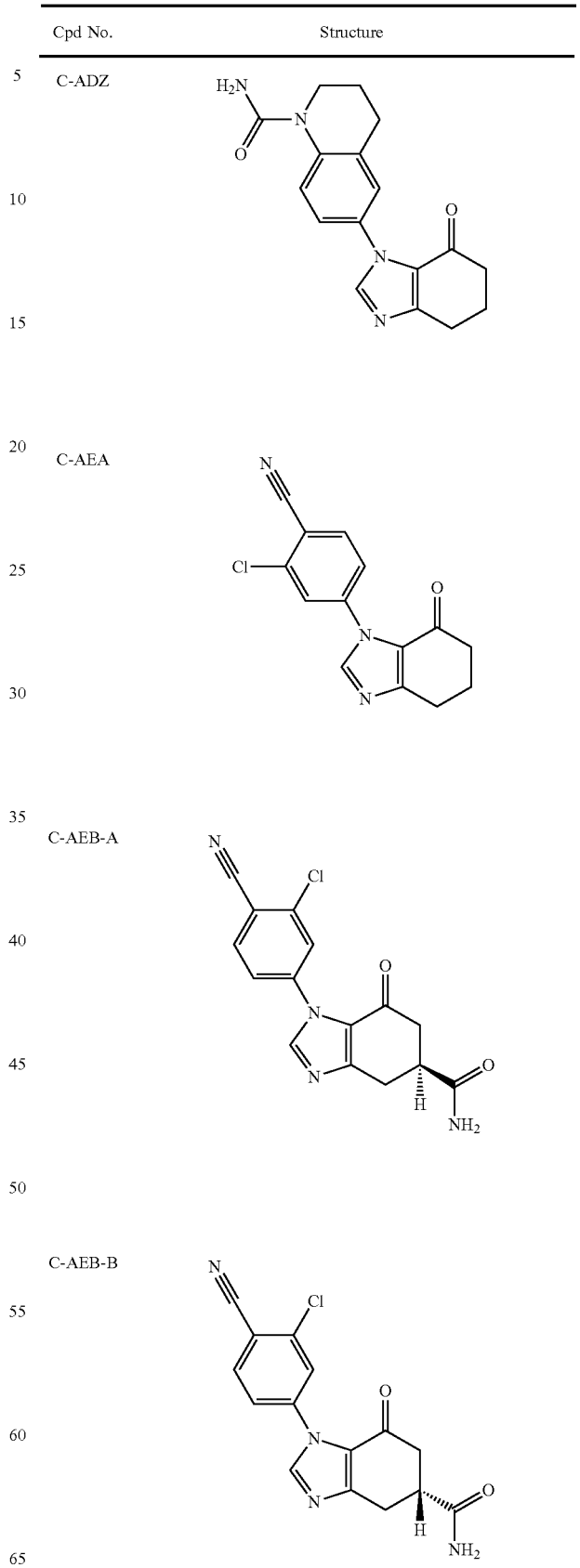 |
| C-AEA | |
| C-AEB-A | |
| C-AEB-B | |

| Cpd No. | Structure |
|---|---|
| C-AED | 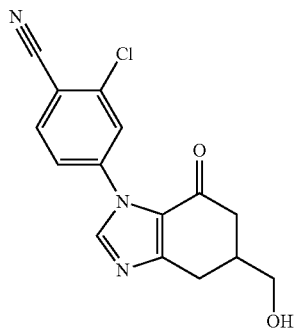 [SMILES: N#Cc1ccc(-n2cnc3c2C(=O)CC(CO)C3)cc1Cl] |
| C-AEE | 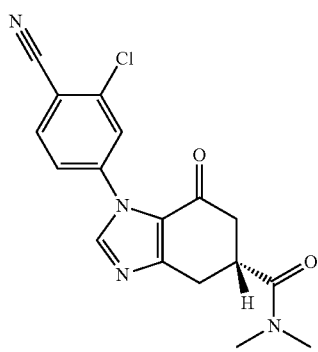 |
| C-AEF | 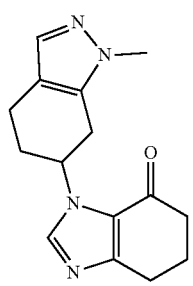 [SMILES: Cn1ncc2c1CC(n1cnc3c1C(=O)CCC3)CC2] |

| Cpd No. | Structure |
|---|---|
| C-AEG | 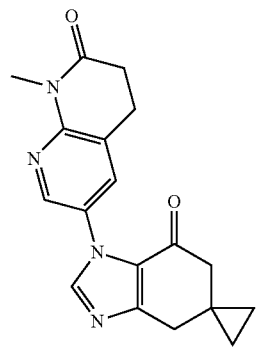 |
| C-AEH | 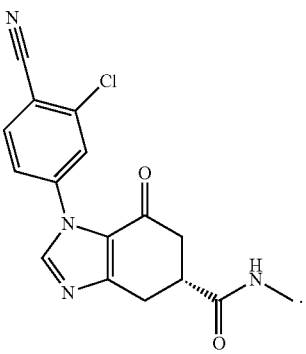 [SMILES: CNC(=O)[C@H]1CC(=O)c2c(ncn2-c2ccc(C#N)c(Cl)c2)C1] |

8. A pharmaceutical composition comprising a compound according to claim 1 and a pharmaceutically acceptable excipient or carrier.

9. A method of treating a disease or disorder that can be alleviated by inhibition of aldosterone synthase selected from the group consisting of diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism comprising administering a therapeutically effective amount of a compound according to claim 1 to a patient in need thereof.

10. The method according to claim 9, wherein the disease or disorder is selected from the group consisting of diabetic nephropathy, glomerulosclerosis, glomerulonephritis, IGA nephropathy, nephritic syndrome and focal segmental glomerulosclerosis (FSGS).

11. The method according to claim 10, wherein the disease is diabetic nephropathy.

* * * * *